(12) United States Patent
Kajihara et al.

(10) Patent No.: US 8,158,763 B2
(45) Date of Patent: *Apr. 17, 2012

(54) SUGAR CHAIN ASPARAGINE DERIVATIVES, SUGAR CHAIN ASPARAGINE, SUGAR CHAIN AND PROCESSES FOR PRODUCING THESE

(75) Inventors: Yasuhiro Kajihara, Yokohama (JP); Kazuaki Kakehi, Nara (JP); Kazuhiro Fukae, Tokushima (JP)

(73) Assignees: Yasuhiro Kajihara, Kanagawa (JP); Otsuka Chemical Co. Ltd., Osaka (JP)

( * ) Notice: Subject to any disclaimer, the term of this patent is extended or adjusted under 35 U.S.C. 154(b) by 817 days.

This patent is subject to a terminal disclaimer.

(21) Appl. No.: 11/976,527

(22) Filed: Oct. 25, 2007

(65) Prior Publication Data

US 2008/0214798 A1 Sep. 4, 2008

Related U.S. Application Data

(62) Division of application No. 10/540,503, filed as application No. PCT/JP03/16523 on Dec. 24, 2003, now Pat. No. 7,304,148.

(30) Foreign Application Priority Data

Dec. 24, 2002 (JP) .................................. 2002-373213
Jul. 28, 2003 (JP) .................................. 2003-202708

(51) Int. Cl.
C07H 1/00 (2006.01)
C07H 5/04 (2006.01)
C07H 5/06 (2006.01)
C08B 37/00 (2006.01)

(52) U.S. Cl. .......... 536/1.11; 536/18.7; 536/53; 536/55; 536/55.3; 536/124

(58) Field of Classification Search ........................ None
See application file for complete search history.

(56) References Cited

U.S. PATENT DOCUMENTS

| 5,627,290 A | 5/1997 | Iida et al. ..................... 549/419 |
| 5,908,766 A | 6/1999 | Yamamoto et al. ............. 435/97 |
| 7,135,566 B2 | 11/2006 | Kajihara et al. ........... 536/123.1 |
| 2004/0181054 A1 | 9/2004 | Kajihara et al. ......... 536/123.13 |

FOREIGN PATENT DOCUMENTS

| JP | 63-502716 | 10/1988 |
| JP | 6-510745 | 12/1994 |
| JP | 6-510746 | 12/1994 |
| JP | 8-9989 A | 1/1996 |
| JP | 2000-169503 A | 6/2000 |
| JP | 2002-45196 A | 2/2002 |
| WO | WO 87/05330 A1 | 9/1987 |
| WO | WO 92/22563 A1 | 12/1992 |
| WO | WO 92/22564 A1 | 12/1992 |

OTHER PUBLICATIONS

Kajiwara, Yasuhiro et al., "Asparagine ni Ketsugo shita 2bunki Fukugogata Tosa Yudotai no Gosei to NMR ni yoru Kozo Kaiseki (Chemoenzymatic synthesis of asparagine linked diantennary olgosaccharide analogues and its NMR analysis)", Dai 22 Kai (22nd), The Japanese Society of Carbohydrate Research, Nenkai Yoshishu (Abstracts of Annual meeting), 2001, p. 33.

The Japanese Biochemical Society, ed., "Shin Seikagaku Jikken Koza (Dai 3 Kan), Toshitsu I, To-Tanpakushitsu (Jo) (Biochemical Experimental Course (vol. 3), Glucide I, Glycoprotein 1)", Tokyo Kagaku Dojin, 1990, pp. 312-349.

MeinJohanns et al., "Novel sequential solid-phase synthesis of N-linked glycopeptides from natural sources", *J. Chem. Soc.*, Perkin Trans. 1, 1998, pp. 549-560.

Kajihara et al. "Efficient Chemical Synthesis of CMP-Neu5Ac and CMP-(Neu5Acα2→8Neu5Ac)" *J Org Chem* 60(17):5732-5735 (1995).

Fournet et al. "Primary Structure of an N-glycosidic Unit Derived from *Sophora japonica* Lectin" *Eur J Biochem* 166:321-324 (1987).

Leteux et al. "Biotinyl-$_L$-3-(2-naphthyl)-alanine Hydrazide Derivatives of N-glycans: Versatile Solid-Phase Probes for Carbohydrate-Recognition Studies" *Glycobiology* 8(3):227-236 (1998).

Pierce-Cretel et al. "Primary Structure of N-glycosidically Linked Asialoglycans of Secretory Immunoglobulins A from Human Milk" *Eur J Biochem* 139:337-349 (1984).

Burkart et al. "An Efficient Synthesis of CMP-3-fluoroneuraminic Acid" *Chem Commun* 16:1525-1526 (1999).

Inazu, et al. "Preparation of Fmoc-asparagine Derivatives Having Natural N-Linked Oligosaccharide, and Its Application to the Synthesis of Glycopeptides." Peptide Science, pp. 153-156, 1998.

Lin, et al. "Enzymatic Synthesis of a Sialyl Lewis X Dimer from Egg Yolk as an Inhibitor of E-Selectin." Bioorganic & Medicinal Chemistry, vol. 3, No. 12, pp. 1625-1630, 1995.

Unverzagt, et al al. "Building Blocks for Glycoproteins: Synthesis of the Ribonuclease B Fragment 21-25 containing an Undecasaccharide N-Glycan," Tetrahedron Letters, vol. 38, No. 32, pp. 5627-5630, 1997.

MeinJohanns, et al. "Novel sequential solid-phase synthesis of N-linked glycopeptides from natural sources," J. Chem. Soc, Perkin Trans. 1, 1998, pp. 549-560.

Haneda, Katsuji et al., "Transglycosylation of intact sialo complex-type oligosaccharides to the N-acetylglucosamine moieties of glycopeptides by *Mucor hiemalis* endo-β-N-acetylglucosaminidase," Carbohydrate Research, vol. 292, pp. 61-70, 1996.

Unverzagt, Carlo, "Building Blocks for Glycoproteins: Synthesis of the Ribonuclease B Fragment 21-25 containing an Undecasaccharide N-Glycan," Tetrahedron Letters, vol. 38, No. 32, pp. 5627-5630, 1997.

(Continued)

*Primary Examiner* — Layla Bland

(74) *Attorney, Agent, or Firm* — Myers Bigel Sibley & Sajovec, PA

(57) ABSTRACT

An asparagine-linked α2,3-oligosaccharide having undeca- to hepta-saccharides, an asparagine-linked α2,6-oligosaccharide having undeca- to hepta-saccharides and containing fluorine and an asparagine-linked oligosaccharide derivative containing at least one fucose in N-acetylglucosamine on the nonreducing terminal side of an asparagine-linked oligosaccharide wherein the asparagine has amino group protected with a lipophilic protective group, and a process for producing these compounds.

18 Claims, No Drawings

OTHER PUBLICATIONS

Unverzagt, Carlo, "Chemoenzymatic synthesis of a sialylated diantennary N-glycan linked to asparagine," *Carbohydrate Research*, vol. 305, pp. 423-431, 1998.

Lin, Chun-Hung et al., "Enzymatic Synthesis of a Sialyl Lewis X Dimer from Egg Yolk as an Inhibitor of E-Selectin," *Bioorganic & Medicinal Chemistry*, vol. 3, No. 12, pp. 1625-1630, 1995.

Inazu, Toshiyuki et al., "Preparation of Fmoc-asparagine Derivatives Having *N*-Linked Oligosaccharide, and Its Application to the Synthesis of Glycopeptides," *Peptide Science*, pp. 153-156, 1998.

Kajiwara, Yasuhiro et al., "Asparagine ni Ketsugo shita 2bunki Fukugogata Tosa Yudotai no Gosei to NMR ni yoru Kozo Kaiseki (Chemoenzymatic synthesis of asparagine linked diantennary olgosaccharide analogues and its NMR analysis)", Dai 22 Kai (22nd), The Japanese Society of Carbohydrate Research, Nenkai Yoshishu (Abstracts of Annual meeting), 2001, p. 33.

The Japanese Biochemical Society, ed., "Shin Seikagaku Jikken Koza (Dai 3 Kan), Toshitsu I, To-Tanpakushitsu (Jo) (Biochemical Experimental Course (vol. 3), Glucide 1, Glycoprotein 1)", Tokyo Kagaku Dojin, 1990, pp. 312-349.

SUGAR CHAIN ASPARAGINE DERIVATIVES, SUGAR CHAIN ASPARAGINE, SUGAR CHAIN AND PROCESSES FOR PRODUCING THESE

TECHNICAL FIELD

The present invention relates to asparagine-linked oligosaccharide derivatives, asparagine-linked oligosaccharides and oligosaccharides, and a process for preparing such compounds.

The present invention relates also to asparagine-linked oligosaccharide derivatives containing fucose and a process for preparing the derivative.

BACKGROUND ART

In recent years, molecules of oligosaccharides have attracted attention as third chain life molecules following nucleic acids (DNA) and proteins. The human body is a huge cell society comprising about 60 trillion cells, and the surfaces of all the cells are covered with oligosaccharide molecules. For example, ABO blood type are determined according to the difference of oligosaccharides over the surfaces of cells.

Oligosaccharides function in connection with the recognition of cells and interaction of cells and are key substances for the establishment of the cell society. Disturbances in the cell society lead, for example, to cancers, chronic diseases, infectious diseases and aging.

For example, it is known that when cells cancerate, changes occur in the structure of oligosaccharides. It is also known that *Vibrio cholerae*, influenza virus, etc. ingress into cells and cause infection by recognizing and attaching to a specific oligosaccharide.

Clarification of oligosaccharide functions leads to development of pharmaceuticals and foods based on novel principles, contributing to the prevention and therapy of diseases, and a wide variety of applications are expected of oligosaccharides.

Oligosaccharides are much more complex than DNA or proteins in structure because of the diversity of arrangements of monosaccharides, modes or sites of linkages, lengths of chains, modes of branches and overall structures of higher order. Accordingly, biological information derived from the structures thereof is more diversified than is the case with DNA and proteins. Although the importance of research on oligosaccharides has been recognized, the complexity and variety of structures thereof have delayed progress in the research on oligosaccharides unlike the studies on DNA and proteins.

Many of proteins present on the surfaces of cell membranes or in serum have oligosaccharides attached thereto as described above. The molecules wherein oligosaccharides are combined covalently with proteins are termed glycoproteins, which can be divided into two groups according to the difference in the mode of linkage between the oligosaccharide and the protein. Oligosaccharides of one type are asparagine-linked oligosaccharides (N-glycoside linkage type) wherein an amino group of the side chain of asparagine (Asn) is linked with the oligosaccharide. Oligosaccharides of the other type are mucin type oligosaccharides (O-glycosidic linkage type) wherein the oligosaccharide is linked with the alcohol of serine (Ser) or threonine (Thr). All the asparagine-linked oligosaccharides have a basic skeleton comprising five sugar moieties, and are divided into subgroups of high-mannose type, complex type and mixture type, according to the kind of the nonreducing terminal sugar moiety of the oligosaccharide linked. On the other hand, the mucin-liked oligosaccharides are divided into four groups according to the difference of the basic skeleton.

Although such oligosaccharides are important compounds, these compounds are insufficient in absolute amounts available. Methods of obtaining oligosaccharides include isolation of oligosaccharides only from glycoproteins which are present in the living body. However, it is difficult to cut off large quantities of oligosaccharides from glycoproteins. Further there are in the living body many oligosaccharides which closely resemble, and difficulty is encountered in obtaining a single oligosaccharide only in a large quantities. It is also difficult to obtain large quantities of oligosaccharides which are not present in the living body.

An object of the present invention is to provide a novel asparagine-linked oligosaccharide derivative containing at least one sialic acid or sialic acid derivative at a nonreducing terminal, and a process for preparing the same.

Another object of the invention is to provide a novel asparagine-linked oligosaccharide containing at least one sialic acid or sialic acid derivative at a nonreducing terminal, and a process for preparing the same.

Another object of the invention is to provide a novel oligosaccharide containing at least one sialic acid or sialic acid derivative at a nonreducing terminal, and a process for preparing the same.

An object of the present invention is to provide a novel asparagine-linked oligosaccharide derivative containing at least one fucose in N-acetylglucosamine on the nonreducing terminal side of an asparagine-linked oligosaccharide wherein the asparagine has amino group protected with a lipophilic (hydrophobic) protective group, and a process for preparing the derivative.

DISCLOSURE OF THE INVENTION

The present invention provides the following inventions.

1. An asparagine-linked α2,3-oligosaccharide derivative having undeca- to hepta-saccharides and represented by the formula (1) given below, and process thereof

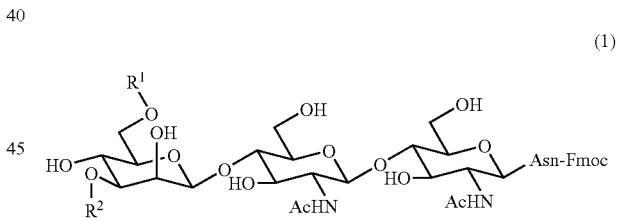

(1)

wherein $R^1$ and $R^2$ are each a hydrogen atom or one of the groups represented by the formulae (2) to (5) and may be the same or different, provided that one of $R^1$ and $R^2$ should always be the group of the formula (2).

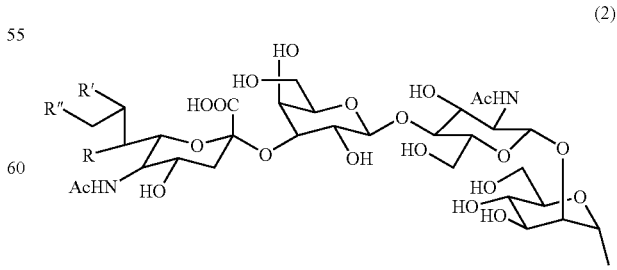

(2)

R, R' and R" are in the following combinations
 (a) R=F, R'=OH, R"=OH
 (b) R=OH, R'=F, R"=OH (c) R=OH, R'=OH, R"=F
(d) R=OH, R'=OH, R"=OH (3)

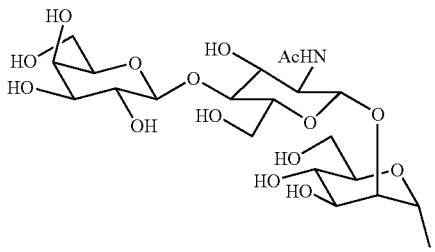

(4)

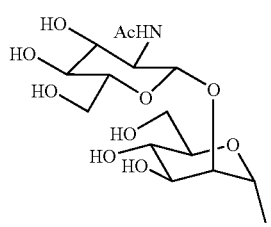

(5)

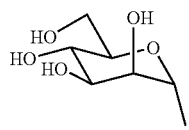

2. An asparagine-linked α2,6-oligosaccharide derivative having undeca- to hepta-saccharides, containing fluorine and represented by the formula (6) given below, and process thereof (6)

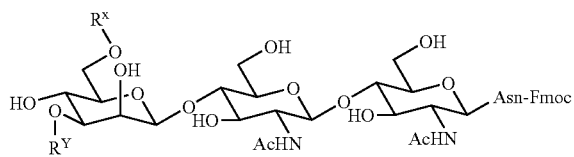

wherein $R^x$ and $R^y$ are each a hydrogen atom, a group represented by the formula (7) or one of the groups represented by the formulae (3) to (5), provided that one of $R^x$ and $R^y$ should always be a group of the formula (7).

(7)

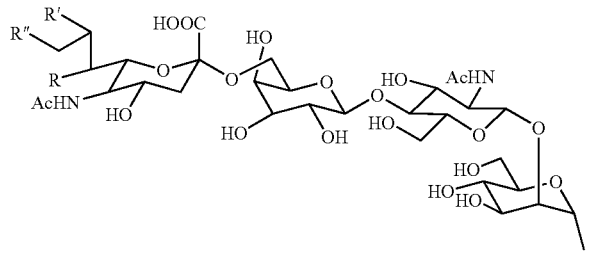

R, R' and R" are in the following combinations
(a) R=F, R'=OH, R"=OH
(b) R=OH, R'=F, R"=OH
(c) R=OH, R'=OH, R"=F 3. An asparagine-linked α2,3-oligosaccharide having undeca- to hepta-saccharides and represented by the formula (8) given below, and process thereof (8)

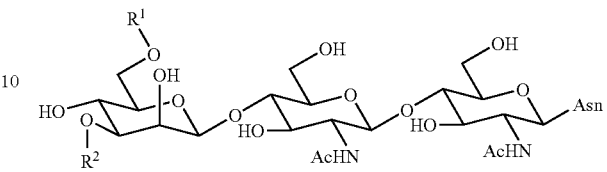

wherein $R^1$ and $R^2$ are as defined above.

4. An asparagine-linked α2,6-oligosaccharide having undeca- to hepta-saccharides, containing fluorine and represented by the formula (9) given below, and process thereof (9)

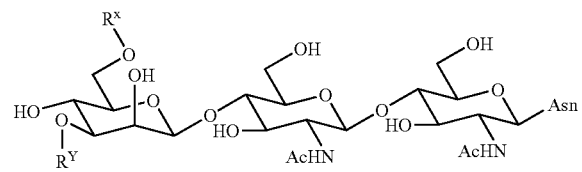

wherein $R^x$ and $R^y$ are as defined above.

5. An α2,3-oligosaccharide having undeca- to hepta-saccharides and represented by the formula (10) given below, and process thereof (10)

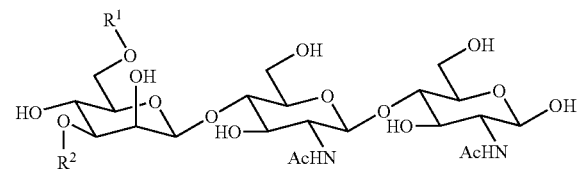

wherein $R^1$ and $R^2$ are as defined above.

6. An α2,6-oligosaccharide having undeca- to hepta-saccharides, containing fluorine and represented by the formula (11) given below, and process thereof (11)

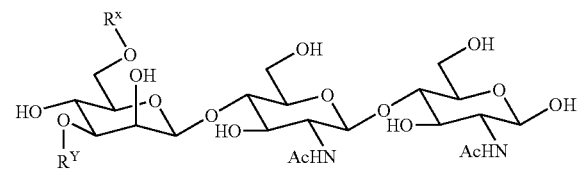

wherein $R^x$ and $R^y$ are as defined above.

7. An asparagine-linked (α2,3)(α2,6)-oligosaccharide derivative having undecasaccharides and represented by the formula (22) given below (22)

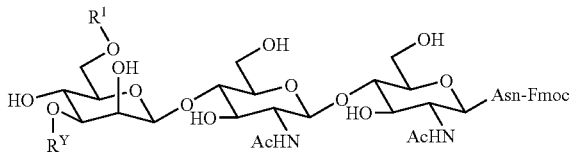

wherein $R^1$ is a group represented by the formula (2), $R^y$ is a group represented by the formula (7) below.

(7)

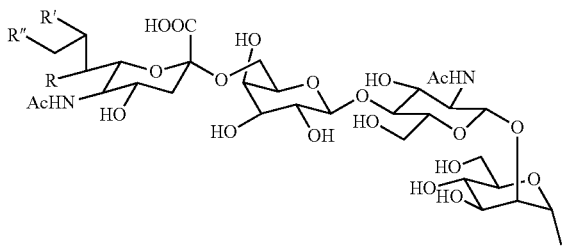

R, R' and R" are in the following combinations
 (a) R=F, R'=OH, R"=OH
 (b) R=OH, R'=F, R"=OH
 (c) R=OH, R'=OH, R"=F
 (d) R=OH, R'=OH, R"=OH 8. An asparagine-linked (α2,3)(α2,6)-oligosaccharide derivative having undecasaccharides and represented by the formula (23) given below (23)

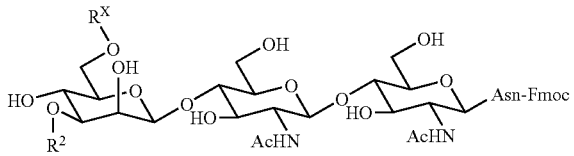

wherein $R^2$ is a group represented by the formula (2), $R^x$ is a group represented by the formula (7) below.

(7)

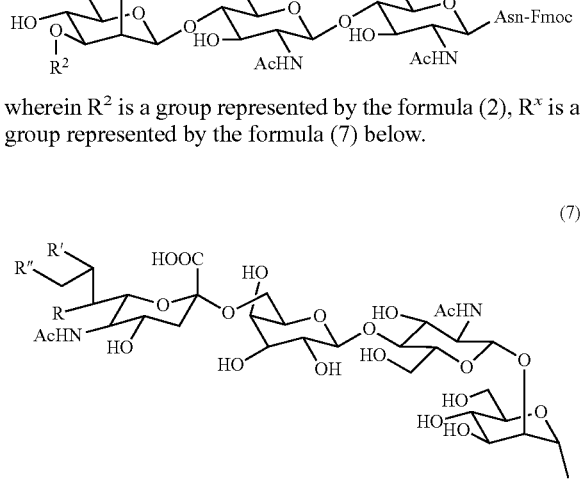

R, R' and R" are in the following combinations
 (a) R=F, R'=OH, R"=OH
 (b) R=OH, R'=F, R"=OH
 (c) R=OH, R'=OH, R"=F
 (d) R=OH, R'=OH, R"=OH The present invention relates to a novel asparagine-linked oligosaccharide derivative containing at least one fucose in N-acetylglucosamine on the nonreducing terminal side of an asparagine-linked oligosaccharide wherein the asparagine has amino group protected with a lipophilic-protective group, and a process for preparing the derivative.

The present inventor has already developed, as disclosed in Japanese Patent Application No. 2001-185685 (hereinafter referred to as the "prior application"), processes for preparing asparagine-linked oligosaccharides derivative, asparagine-linked oligosaccharides and oligosaccharides which processes are capable of producing various isolated asparagine-linked oligosaccharides derivative with greater ease and in larger scale than conventionally, and further novel asparagine-linked oligosaccharides derivative, asparagine-linked oligosaccharides and oligosaccharides, wherein oligosaccharides deficient in sugar moieties as desired are linked.

The processes of the prior application include:
(1) a process for preparing an asparagine-linked oligosaccharide derivative derived from an asparagine-linked oligosaccharide which process includes the steps of:
 (a) introducing a lipophilic protective group into an asparagine-linked oligosaccharide or at least two asparagine-linked oligosaccharides included in a mixture comprising the oligosaccharide or said at least two oligosaccharides to obtain an asparagine-linked oligosaccharide derivative mixture, and
 (b) hydrolyzing the asparagine-linked oligosaccharide derivative mixture or asparagine-linked oligosaccharides derivative included in this mixture and subjecting the resulting mixture to chromatography to separate off asparagine-linked oligosaccharides derivative,
(2) a process for preparing an asparagine-linked oligosaccharide derivative according to (1) which further includes the step (b') of hydrolyzing the asparagine-linked oligosaccharides derivative separated off by the step (b) with a glycosidase,
(3) a process for preparing an asparagine-linked oligosaccharide derivative according to (1) or (2) wherein the mixture comprising the oligosaccharide or said at least two oligosaccharides includes a compound of the formula (A) below and/or a compound corresponding to said compound wherein at least one sugar moiety is deficient,
(4) a process for preparing an asparagine-linked oligosaccharide derivative according to any one of (1) to (3) wherein the lipophilic protective group is a fluorenylmethoxycarbonyl (Fmoc) group,
(5) a process for preparing an asparagine-linked oligosaccharide derivative according to any one of (1) to (3) wherein the step (a) is the step of introducing Fmoc group into the asparagine-linked oligosaccharide or said at least two asparagine-linked oligosaccharides having a sialic moiety at a nonreducing terminal and included in the mixture, and introducing benzyl group into the sialic moiety to obtain the asparagine-linked oligosaccharide derivative mixture,
(6) A process for preparing an asparagine-linked oligosaccharide including the steps of:
 (a) introducing a lipophilic protective group into an asparagine-linked oligosaccharide or at least two asparagine-linked oligosaccharides included in a mixture comprising the oligosaccharide or said at least two oligosaccharides to obtain an asparagine-linked oligosaccharide derivative mixture,
 (b) hydrolyzing the asparagine-linked oligosaccharide derivative mixture or asparagine-linked oligosaccharides derivative included in this mixture and subjecting the resulting mixture to chromatography to separate off asparagine-linked oligosaccharides derivative, and (c) removing the protective group from the asparagine-linked oligosaccharides derivative separated off in the step (b) to obtain asparagine-linked oligosaccharides, (7) a process for preparing an asparagine-linked oligosaccharide according to (6) which further includes:

the step (b') of hydrolyzing the asparagine-linked oligosaccharides derivative separated off by the step (b) with a glycosidase, and/or the step (c') of hydrolyzing the asparagine-linked oligosaccharides obtained by the step (c) with a glycosidase, (8) a process for preparing an asparagine-linked oligosaccharide according to (6) or (7) wherein the mixture comprising the oligosaccharide or said at least two oligosaccharides includes a compound of the formula (A) below and/or a compound corresponding to said compound wherein at least one sugar moiety is deficient, (9) a process for preparing an asparagine-linked oligosaccharide according to any one of (6) to (8) wherein the lipophilic protective group is Fmoc group.

(10) a process for preparing an asparagine-linked oligosaccharide according to any one of (6) to (8) wherein the step (a) is the step of introducing Fmoc group into the asparagine-linked oligosaccharide or said at least two asparagine-linked oligosaccharides having a sialic moiety at a nonreducing terminal and included in the mixture, and introducing benzyl group into the sialic moiety to obtain the asparagine-linked oligosaccharide derivative mixture, etc.

of asparagine-linked oligosaccharides derivative, followed by separation of the mixture into individual asparagine-linked oligosaccharides derivative. The term an "asparagine-linked oligosaccharide" as used herein refers to an oligosaccharide having asparagine linked thereto. Further the term "oligosaccharides capable of linking to asparagine" refers to a group of oligosaccharides wherein N-acetylglucosamine present at a reducing terminal is attached by N-glucoside linkage to the acid amino group of asparagine (Asn) in the polypeptide of a protein and which has Man(β1-4)GlcNac (β1-4)GlcNac as the core structure. The term an "asparagine-linked oligosaccharide derivative" refers to an asparagine-linked oligosaccharide wherein a lipophilic protective group is attached to asparagine moiety. Further "AcHN" in the structural formulae of compounds refers to an acetamido group.

As described previously, oligosaccharides derived from naturally occurring glycoproteins are a mixture of oligosaccharides which are randomly deficient in the sugar moiety at the nonreducing terminal. The present inventors have unexpectedly found that the introduction of a lipophilic protective group into an oligosaccharide derived from a naturally occurring glycoprotein, preferably into asparagine-linked oligosaccharides included in a mixture thereof, makes it possible to readily separate a mixture of asparagine-linked oligosaccharides derivative having the protective group introduced therein into individual asparagine-linked oligosaccharides derivative by a known chromatographic procedure. Consequently, asparagine-linked oligosaccharides derivative having different structures can be prepared individually in (A)

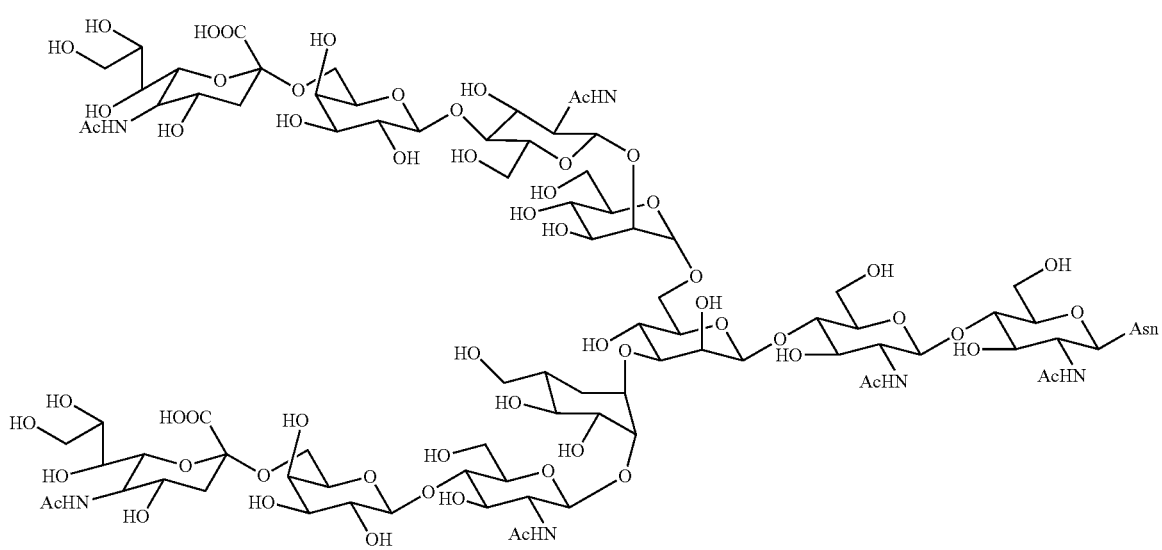

Since a detailed description is given in the prior application about the preparation of these asparagine-linked oligosaccharide derivatives and asparagine-linked oligosaccharides, reference will be made to the application. However, what is disclosed in the prior application will be described to some extent. The process of the prior application for preparing asparagine-linked oligosaccharides derivative is distinctly characterized in that a lipophilic protective group is introduced into (linked with) a asparagine-linked oligosaccharide derived from a naturally occurring glycoprotein, preferably asparagine-linked oligosaccharides included in a mixture of asparagine-linked oligosaccharides obtained from oligosaccharides capable of linking to asparagine, to obtain a mixture large quantities. For example, asparagine-linked oligosaccharides derivative which resemble in structure and which are conventionally difficult to separate can be separated from one another, and these compounds can be prepared easily in large quantities. Further a glycosidase can be caused to act on the resulting asparagine-linked oligosaccharides derivative and thereby prepare various asparagine-linked oligosaccharides derivative.

Thus, introducing a lipophilic protective group into asparagine-linked oligosaccharides provides derivatives and makes it possible to separate the asparagine-linked oligosaccharides derivative from one another. Presumably this is attributable to the fact that the introduction of the lipophilic protective group gives improved lipophilicity (hydrophobicity) to the whole asparagine-linked oligosaccharides derivative to ensure remarkably improved interaction between the oligosaccharide and the reverse-phase column to be used favorably, consequently separating the asparagine-linked oligosaccharides derivative from one another by reflecting the difference of structure between the oligosaccharides with high sensitivity.

Further by removing the protective group from the asparagine-linked oligosaccharides derivative obtained, various asparagine-linked oligosaccharides can be artificially prepared easily in large amounts according to the prior application.

However, the asparagine-linked oligosaccharide derivative, the asparagine-linked oligosaccharide and the oligosaccharide obtained by the invention of the above-mentioned prior application are all α2,6-bonded compounds.

Furthermore, the asparagine-linked oligosaccharide derivative, asparagine-linked oligosaccharide and oligosaccharide obtained by the invention of the above-mentioned prior application are all compounds wherein the oligosaccharide has no fucose linked thereto.

The present invention provides an asparagine-linked oligosaccharide derivative, an asparagine-linked oligosaccharide and an oligosaccharide which are α2,6-bonded compounds not disclosed in the above-mentioned prior application, and further provides an asparagine-linked oligosaccharide derivative, an asparagine-linked oligosaccharide and an oligosaccharide which are all novel and are α2,6-bonded compounds and which also contain fluorine.

The present invention further provides an asparagine-linked oligosaccharide derivative which is a fucose-linked compound not disclosed in the above-mentioned prior application.

The difference between α2,3-bonded compounds and α2,6-bonded compounds will be described below.

The α2,3-bonded compound and the α2,6-bonded compound represent modes of bonding between sialic acid and galactose. The former refers to a compound wherein the carbon at the 2-position of sialic acid and the carbon at the 3-position of galactose are linked by α-bonding. The latter refers to a compound wherein the carbon at the 2-position of sialic acid and the carbon at the 6-position of galactose are linked by α-bonding. Thus, the difference resides in the difference in the carbon-to-carbon bond between sialic acid and galactose.

This difference is involved, for example, in the receptor recognition of influenza viruses. Influenza viruses recognize oligosaccharides having sialic acid at the terminal as the receptor. However, the human influenza virus is different from the avian influenza virus in receptor specificity. The former specifically recognizes oligosaccharides wherein sialic acid is α2,6-bonded to galactose, whereas the latter specifically recognizes oligosaccharides wherein sialic acid is α2,3-bonded to galactose. It is known that the difference in the mode of bonding between sialic acid and galactose, and further difference in sialic acid, play a great role in restricting the host range of influenza viruses.

The present invention relates to asparagine-linked oligosaccharide derivatives, asparagine-linked oligosaccharides and oligosaccharides which are novel and not disclosed in the prior application, and a process for preparing such compounds.

According to the process of the invention, an asparagine-linked oligosaccharide (nonasaccharide-Asn-Fmoc) protected with a lipophilic protective group and serving as the starting material is reacted with sialic acid transferase to transfer sialic acid or a sialic acid derivative to the oligosaccharide, and the resulting asparagine-linked oligosaccharide protected with the lipophilic protective group is subjected to chromatography for separation to obtain an asparagine-linked disialooligosaccharide derivative protected with the lipophilic protective group and two kinds of asparagine-linked monosialooligosaccharide derivatives.

The asparagine-linked disialooligosaccharide derivative and two kinds of asparagine-linked monosialooligosaccharide derivatives obtained are then subjected to sugar hydrolysis to obtain asparagine-linked nona- to hepta-saccharide derivatives having sialic acid or a sialic acid derivative.

The asparagine-linked undeca- to hepta-saccharide derivative or asparagine-linked disialooligosaccharide (α2,6-undecasaccharide-Asn-Fmoc) obtained above are subjected to sugar hydrolysis as starting materials to obtain asparagine-linked deca- to hexa-saccharide derivatives, to which fucose is transferred using sugar transferase to obtain asparagine-linked trideca- to hepta-saccharide derivatives containing fucose.

The protecting group is not particularly limited, and there can be used, for instance, a carbonate-based or amide-based protecting group, such as Fmoc group, t-butyloxycarbonyl (Boc) group, benzyl group, allyl group, allyloxycarbonate group, or acetyl group. From the viewpoint that the resulting asparagine-linked oligosaccharide derivative can be immediately used in the synthesis of a desired glycopeptide, the above protecting group is preferably Fmoc group, Boc group or the like, more preferably Fmoc group. The Fmoc group is especially effective when there exists in the oligosaccharide a sugar, such as sialic acid, which is relative unstable under acidic conditions. The introduction of the protecting group may be carried out according to a known process (for instance, Protecting Groups in Organic Chemistry, John Wiley & Sons INC., New York 1991, ISBN 0-471-62301-6).

For instance, when Fmoc group is used, an appropriate amount of acetone is added to the mixture containing asparagine-linked oligosaccharides, 9-fluorenylmethyl-N-succinimidyl carbonate and sodium hydrogencarbonate are further added thereto and dissolved, and thereafter the resulting mixture is subjected to a binding reaction of Fmoc group to an asparagine moiety at 25.degree. C., whereby the Fmoc group can be introduced into the asparagine moiety of the above asparagine-linked oligosaccharide.

According to the procedures described above, a mixture of the asparagine-linked oligosaccharide derivatives into each of which a lipophilic protecting group is introduced is obtained.

The sialic acid to be used is one generally available commercially, or one prepared by chemical synthesis.

Examples of sialic acid derivatives usable are those generally available commercially, or those prepared by chemical synthesis. More specific examples of such derivatives are those wherein the hydroxyl group attached to the carbon atom at the 7-position, 8-position or 9-position of sialic acid is substituted with a hydrogen atom or halogen atom. Examples of halogen atoms are fluorine, chlorine, bromine, etc., among which fluorine is preferred.

Examples of sialic acid transferases usable are those generally available commercially, those naturally occurring and those prepared by genetic recombination. A suitable transferase can be selected in accordance with the kind of sialic acid or sialic acid derivative to be transferred. A more specific example is one derived from a rat recombinant which is an α2,3-transferase, and one derived from rat liver which is an α2,6-transferase. Alternatively, sialic acid or a sialic acid derivative may be transferred using sialydase to shift equilibrium as by pH adjustment.

The separation of each of asparagine-linked oligosaccharide derivatives by chromatography can be carried out by appropriately using known chromatographies, singly or in a combination of plural chromatographies.

For instance, the resulting mixture of asparagine-linked oligosaccharide derivatives is purified by a gel filtration column chromatography, and then purified by using HPLC. The column which can be used in HPLC is preferably a reverse phase column, for instance, ODS, phenyl-based, nitrile-based, or anion exchange-based column, and concretely, a monoQ column manufactured by Pharmacia, Iatro-beads column manufactured by Iatron can be utilized. The separation conditions and the like may be adjusted by referring to a known condition. According to the above procedures, each of the desired asparagine-linked oligosaccharide derivatives can be obtained from the mixture of asparagine-linked oligosaccharide derivatives.

In the case where the protective group is Fmoc group, asparagine-linked oligosaccharide derivatives of the formulae (12), (13), (17), (18), (22) and (23) can be obtained by the above procedures.

Furthermore, the asparagine-linked oligosaccharide derivative having a desired oligosaccharide structure can be efficiently obtained by hydrolyzing the asparagine-linked oligosaccharide derivatives separated in the above step. For instance, in the stage of separating the asparagine-linked oligosaccharide derivatives, the asparagine-linked oligosaccharide derivatives can be roughly separated by limiting the kinds of the asparagine-linked oligosaccharide derivatives contained in the mixture, and thereafter the asparagine-linked oligosaccharide derivatives are subjected to hydrolysis, for instance, hydrolysis with a glycosidase, whereby the asparagine-linked oligosaccharide derivatives having the desired oligosaccharide structures can be efficiently obtained. Here, the hydrolysis can be carried out in the same manner as described above. Especially, it is preferable that the hydrolysis is carried out with a glycosidase of which cleavage mode of the oligosaccharide moieties is clear, from the viewpoint of more efficiently obtaining the asparagine-linked oligosaccharide derivatives having the desired oligosaccharide structures.

For instance, the removal of the galactose moieties can be accomplished by dissolving the compounds to be hydrolysed in a buffer (for instance, phosphate buffer, acetate buffer, Good's buffer or the like), and carrying out cleavage reaction of the galactose moieties with a galactosidase in accordance with a known condition. The compounds to be hydrolysed may be individually isolated compounds or a mixture of these compounds. It is preferable that a commercially available known exo-type enzyme is utilized for the galactosidase used in this reaction. Also, the enzyme may be a newly isolated enzyme or an enzyme generated by genetic engineering, as long as the enzyme has a similar activity. Next, in the same manner as described above, the reaction solution obtained after the reaction (a mixture of asparagine-linked oligosaccharide derivatives of which sugar moieties are cleaved) may be subjected to chromatography to give each of asparagine-linked oligosaccharide derivatives. For instance, it is preferable that the separation is carried out by HPLC (ODS column, eluent being a 50 mM aqueous ammonium acetate:acetonitrile=82:18).

The removal of the N-acetylglucosamine moieties can be accomplished by dissolving the compounds to be hydrolysed in a buffer (for instance, phosphate buffer, acetate buffer, Good's buffer or the like), and carrying out cleavage reaction of the N-acetylglucosamine moieties with an N-acetylglucosaminidase in accordance with a known condition. Also, an N-acetylhexosaminidase can be used. The compounds to be hydrolysed may be individually isolated compounds or a mixture of these compounds. It is preferable that a commercially available known exo-type enzyme is utilized for each enzyme used in this reaction. Also, the enzyme may be a newly isolated enzyme or an enzyme generated by genetic engineering, as long as the enzyme has a similar activity. Next, in the same manner as described above, the reaction solution obtained after the reaction (a mixture of asparagine-linked oligosaccharide derivatives of which oligosaccharide moieties are cleaved) is subjected to chromatography to give each of asparagine-linked oligosaccharide derivatives. For instance, it is preferable that the separation is carried out by HPLC (ODS column, eluent being a 50 mM aqueous ammonium acetate:methanol=65:35 or a 50 mM aqueous ammonium acetate:acetonitrile=82:18).

The removal of the mannose moieties can be accomplished by dissolving the compounds to be hydrolysed in a buffer (for instance, phosphate buffer, acetate buffer, Good's buffer or the like), and carrying out cleavage reaction of the mannose moieties with a mannosidase under a known condition. The compounds to be hydrolysed may be individually isolated compounds or a mixture of these compounds. It is preferable that a commercially available known exo-type enzyme is utilized for the mannosidase used in this reaction. Also, the enzyme may be a newly isolated enzyme or an enzyme generated by genetic engineering, as long as the enzyme has a similar activity. Next, in the same manner as described above, the reaction solution obtained after the reaction (a mixture of asparagine-linked oligosaccharide derivatives of which oligosaccharide moieties are cleaved) is subjected to chromatography to give each of asparagine-linked oligosaccharide derivatives. For instance, it is preferable that the separation is carried out by HPLC (ODS column, eluent: there can be used, for instance, a mixed solution of a buffer such as an about 10 to about 200 mM ammonium acetate and a water-soluble organic solvent with lipophilicity such as acetonitrile, or ethanol, or methanol, or butanol, or propanol in appropriate amounts; when exemplified herein, it is preferable that the eluent is a 50 mM aqueous ammonium acetate:acetonitrile=82:18).

It is possible to prepare novel asparagine-linked oligosaccharide derivatives containing at least one fucose in N-acetylglucosamine on the nonreducing terminal side of an asparagine-linked oligosaccharide wherein the asparagine has amino group protected with a lipophilic protective group, by obtaining various asparagine-linked oligosaccharide derivatives in this way and thereafter causing the transfer of fucose.

The fucose to be used is one generally available commercially, or one prepared by chemical synthesis.

Examples of fucosyl transferases usable are those generally available commercially, those naturally occurring and those prepared by genetic recombination. A suitable fucos transferase can be selected in accordance with the kind of fucose to be transferred. A more specific example is Fucosyltransferase V (human recombinant, plasma-derived, serum-derived, milk-derived or liver-derived) which is an enzyme for transferring fucose to N-acetylglucosamine on the nonreducing terminal of asparagine-linked oligosaccharides. Alternatively, fucose can be transferred using fucosidase and shifting equilibrium as by pH adjustment.

The separation of each of asparagine-linked oligosaccharide derivatives by chromatography can be carried out by appropriately using known chromatographies, singly or in a combination of plural chromatographies.

For instance, the resulting mixture of asparagine-linked oligosaccharide derivatives is purified by a gel filtration column chromatography, and then purified by using HPLC. The column which can be used in HPLC is preferably a reverse phase column, for instance, ODS, phenyl-based, nitrile-based, or anion exchange-based column, and concretely, a monoQ column manufactured by Pharmacia, Iatro-beads column manufactured by Iatron can be utilized. The separation conditions and the like may be adjusted by referring to a known condition. According to the above procedures, each of the desired asparagine-linked oligosaccharide derivatives can be obtained from the mixture of asparagine-linked oligosaccharide derivatives.

As described above, each of the various asparagine-linked oligosaccharide derivatives of which branching structures at the terminals of the oligosaccharides are not uniform, can be obtained as individual isolated compounds by further hydrolyzing the derivatives with various glycosidases and the like to remove the sugar moieties at non-reducing terminals of the oligosaccharides after the obtainment of each of the asparagine-linked oligosaccharide derivatives. Moreover, even a larger number of the kinds of the asparagine-linked oligosaccharide derivatives can be prepared by changing the order or the kind of hydrolysis with various glycosidases.

According to a conventional process, enormous amounts of time and cost for obtaining the asparagine-linked oligosaccharide derivatives having very limited oligosaccharide structures are required even on an analytical scale. On the contrary, according to the present invention, about 1 gram of the asparagine-linked oligosaccharide derivatives having desired oligosaccharide structures can be prepared in an about 2-week period by using a conventional gel filtration column, HPLC column, and at least three kinds of glycosidases (for instance, galactosidase, mannosidase, and N-acetylglucosamidase) without necessitating any particular devices or reagents.

In accordance with the procedures described above, when the protecting group, for instance, is Fmoc group, there can be efficiently obtained a asparagine-linked oligosaccharide derivative of the formula: (14) to (16), (19) to (21) in individually isolated compounds or a mixture of these compounds.

Also, the present invention provides a process for preparing a asparagine-linked oligosaccharide capable of obtaining each of the various isolated asparagine-linked oligosaccharides in a large amount. The above process further comprises, subsequent to the step of preparing a asparagine-linked oligosaccharide derivative in accordance with the above process for preparing a asparagine-linked oligosaccharide derivative, a step of removing the protecting group from the resulting asparagine-linked oligosaccharide derivative.

The removal of the protecting group from the asparagine-linked oligosaccharide derivative can be carried out in accordance with a known process (for instance, see Protecting Groups in Organic Chemistry, John Wiley & Sons INC., New York 1991, ISBN 0-471-62301-6). For instance, when the protecting group is Fmoc group, the Fmoc group can be removed by adding morpholine to the asparagine-linked oligosaccharide derivative in N,N-dimethylformamide (DMF) to carry out the reaction. On the other hand, Boc group can be removed by a reaction with a weak acid. After the removal of the protecting group, a asparagine-linked oligosaccharide may be properly obtained by purifying a reaction mixture by a known process such as various chromatographies employing a gel filtration column, an ion exchange column or the like or a process of separation by HPLC as desired.

In accordance with the procedures described above, asparagine-linked oligosaccharides of the formula: (8) and (9) are obtained in individually isolated compounds or a mixture of these compounds.

Further, the present invention provides a process for preparing a oligosaccharide capable of obtaining the various isolated oligosaccharides in a large amount. The above process further comprises, subsequent to the step of preparing a asparagine-linked oligosaccharide in accordance with the above process for preparing a asparagine-linked oligosaccharide, a step of removing an asparagine moiety from the resulting asparagine-linked oligosaccharide.

The removal of the asparagine moiety from the asparagine-linked oligosaccharide can be carried out in accordance with a known process. For instance, the asparagine-linked oligosaccharide is reacted with anhydrous hydrazine and then acetylated to remove the asparagine moiety, whereby oligosaccharide can be obtained. Also, oligosaccharide can be also obtained by refluxing the asparagine-linked oligosaccharide with heating in a basic aqueous solution and thereafter acetylating the asparagine-linked oligosaccharide to remove the asparagine moiety. After the removal of the asparagine moiety, the oligosaccharide may be purified appropriately by a known process such as various chromatographies employing a gel filtration column, an ion exchange column or the like, and a separation process by HPLC as desired.

In accordance with the procedures described above, oligosaccharides of the formulas (10) and (11) are obtained in individually isolated compounds or a mixture of these compounds.

As described above, according to the present invention, the asparagine-linked oligosaccharide derivative, the asparagine-linked oligosaccharide and the oligosaccharide (hereinafter these three terms are collectively referred to as "oligosaccharide series" in some case) each having a desired oligosaccharide structure can be prepared at a low cost, efficiently and in a large amount.

The oligosaccharide series of the invention are very useful in the field of development of pharmaceuticals. For example, vaccines for cancers are an example of application to the development of drugs. It is known that cells developing cancer produce an oligosaccharide which is not found in the living body. It is also known that when chemically prepared and given to the human body as a vaccine, such an oligosaccharide inhibits the growth of cancer. If the desired oligosaccharide series can be produced according to the invention, it is possible to prepare a vaccine which is effective for treating cancer. The oligosaccharide series obtained by the invention can further be made into derivatives by attaching novel sugar moieties thereto through combinations of chemical reactions and reactions of sugar transferases for the preparation of novel vaccines.

BEST MODE OF CARRYING OUT THE INVENTION

The present invention will be described below with reference to Reference Examples and Examples, to which the invention is not limited.

Reference Example 1

Preparation of α2,6-Asparagine-Linked Disialooligosaccharide

In 100 ml of a tris-hydrochloric acid-calcium chloride buffer (TRIZMA BASE 0.05 mol/l, calcium chloride 0.01 mol/l, pH 7.5) was dissolved 2.6 g of an egg-derived crude SGP (sialyl glycopeptide). 58 mg (772 μmol) of sodium azide and 526 mg of Actinase-E (manufactured by Kaken Pharmaceutical Co., Ltd.) were added to this solution, and the mixture was allowed to stand at 37° C. After 65 hours, 263 mg of Actinase-E was added again, and the mixture was allowed to stand at 37° C. for additional 24 hours. This solution was freeze dried, and thereafter the residue was purified twice by gel filtration column chromatography (Sephadex G-25, 2.5 φ×1 m, eluent: water, flow rate: 1.0 ml/min), to give 1.3 g (555 μmol) of a desired α2,6-asparagine-linked disialooligosaccharide.

The physical data for the resulting α2,6-asparagine-linked disialooligosaccharide are as follows.

$^1$H-NMR (D$_2$O, 30° C.)

δ5.13 (s, 1H, Man4-H-1), 5.07 (d, 1H, J=9.5 Hz, GlcNAc1-H-1), 4.95 (s, 1H, Man4-H-1), 4.77 (s, 1H, Man3-H-1), 4.61 (d, 1H, J=7.6 Hz, GlcNAc2-H-1), 4.60 (d, 2H, J=7.6 Hz, GlcNAc5, 5-H-1), 4.44 (d, 2H, J=8.0 Hz, Gal6, 6-H-1), 4.25 (bd, 1H, Man3-H-2), 4.20 (bdd, 1H, Man4-H-2), 4.12 (bd, 1H, Man4-H-2), 2.94 (dd, 1H, J=4.5 Hz, 17.2 Hz, Asn-βCH), 2.85 (dd, 1H, J=7.0 Hz, 17.2 Hz, Asn-βCH), 2.67, 2.66 (dd, 2H, J=4.6 Hz, 12.4 Hz, NeuAc7,7-H-3$_{eq}$), 2.07 (s, 3H, Ac), 2.06 (s, 6H, Ac×2), 2.02 (s, 6H, Ac×2), 2.01 (s, 3H, Ac), 1.71 (dd, 2H, J=12.4 Hz, 12.4 Hz, NeuAc7, 7-H-3$_{ax}$.)

C. for 35 minutes, the solution was cooled on ice, and a saturated aqueous sodium hydrogencarbonate was added thereto to adjust its pH 7. The solution was freeze dried, and thereafter the residue was purified by gel filtration column chromatography (Sephadex G-25, 2.5 φ×1 m, eluent: water, flow rate: 1.0 ml/min), to give 534 mg of a mixture of α2,6-asparagine-linked disialooligosaccharide, two kinds of a 2,6-asparagine-linked monosialooligosaccharide and asparagine-linked asialooligosaccharide. These four components were proceeded to the next step without being isolated from each other.

The physical data for the resulting oligosaccharides mixture are as follows.

$^1$H-NMR (D$_2$O, 30%)

5.13 (s, Man4-H1), 5.12 (s, Man4-H1), 5.01 (d, GlcNAc1-H1), 4.94 (s, Man4'-H1), 4.93 (s, Man4'-H1), 4.82 (s, Man3-H1), 4.60 (d, GlcNAc2-H1), 4.58 (d, GlcNAc5,5'-H1), 4.47 (dd, Gal6,6'-H1), 4.44 (d, Gal6,6'-H1), 4.24 (d, Man3-H2), 4.19 (d, Man4'-H2), 4.11 (d, Man4-H2), 2.97 (bdd, AsN-βCH), 2.72 (dd, NeuAc7-H3eq, NeuAc7-H3eq), 2.64 (bdd, AsN-βCH), 2.15 (s×5, —Ac), 1.79 (dd, NeuAc7-H3ax, NeuAc7'-H3ax)

A 429-mg quantity of the obtained oligosaccharides mixture was dissolved in 16.3 ml of acetone and 11.2 ml of water.

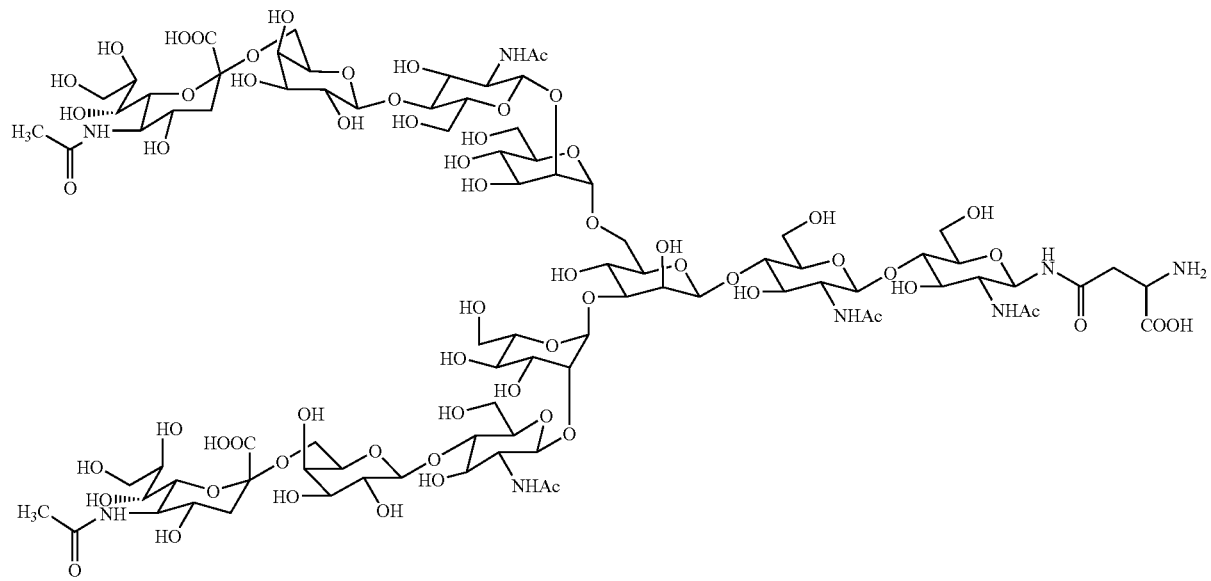

(A)

Reference Example 2

Preparation of Compounds 1, 2, 3 and 4

α2,6-Asparagine-linked disialooligosaccharide (609 mg, 261 μmol) obtained in Reference Example 1 was dissolved in 20.7 ml of water, and 13.8 ml of 0.1 N hydrochloric acid was added thereto. Immediately after heating this solution at 70°

To the solution were added 9-fluorenyl methyl-N-succinimidyl carbonate (155.7 mg, 461.7 μmol) and sodium hydrogencarbonate (80.4 mg, 957 μmol), and the mixture was stirred at room temperature for 2 hours. This solution was applied to an evaporator to remove acetone, and the remaining solution was purified by gel filtration column chromatography (Sephadex G-25, 2.5 φ×1 m, eluent: water, flow rate: 1.0 ml/min), to give 309 mg of a mixture of Compound 1, Compounds 2 and 3, and Compound 4. This mixture was purified by HPLC (ODS column, eluent: 50 mM aqueous ammonium acetate:methanol=65:35, 2.0 φ×25 cm, flow rate: 3 ml/min). As a result, Compound 1 was eluted after 51 minutes, a mixture of Compounds 2 and 3 was eluted after 67 minutes, and Compound 4 was eluted after 93 minutes. Each of the fractions were collected and freeze dried, and thereafter desalted by gel filtration column chromatography (Sephadex G-25, 2.5 φ×30 cm, eluent: water, flow rate: 1.0 ml/min), thereby giving 150 mg of a desired mixture of Compounds 2 and 3.

The physical data for the resulting Compound 1 are as follows.

$^1$H-NMR (D$_2$O, 30° C.)

7.99 (2H, d, Fmoc), 7.79 (2H, d, Fmoc), 7.55 (4H, m, Fmoc), 5.15 (1H, s, Man4-H1), 5.06 (1H, d, GlcNAc1-H1), 4.95 (1H, s, Man4'-H1), 4.82 (1H, s, Man3-H1), 4.69 (1H, d, GlcNAc2-H1), 4.67 (2H, d, GlcNAc5,5'-H1), 4.53 (2H, d, Gal6,6'-H1), 4.34 (1H, d, Man3-H2), 4.27 (1H, d, Man4'-H2), 4.19 (1H, d, Man4-H2), 3.03 (1H, bdd, AsN-βCH), 3.00 (1H, bdd, AsN-βCH), 2.76 (2H, dd, NeuAc7,7'-H3eq), 2.15 (18H, s×6, —Ac), 1.79 (2H, dd, NeuAc7,7'-H3ax); HRMS Calcd for C$_{103}$H$_{154}$N$_8$NaO$_{66}$[M+Na+] 2581.8838, found, 2581.8821

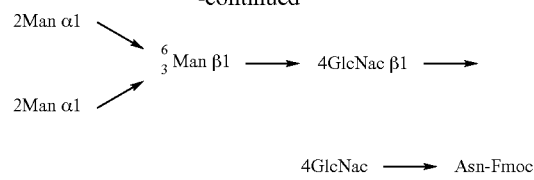

The physical data for the resulting mixture of Compounds 2 and 3 are as follows.

$^1$H-NMR (D$_2$O, 30° C.)

7.99 (d, Fmoc), 7.79 (d, Fmoc), 7.55 (m, Fmoc), 5.14 (s, Man4-H1), 5.12 (s, Man4-H), 5.00 (d, GlcNAc1-H1), 4.94 (s, Man4'-H1), 4.93 (s, Man4'-H1), 4.82 (s, Man3-H1), 4.60 (d, GlcNAc2-H1), 4.58 (d, GlcNAc5,5'-H1), 4.46 (dd, Gal6,6'-H1), 4.44 (d, Gal6,6'-H1), 4.24 (d, Man3-H2), 4.19 (d, Man4'-H2), 4.11 (d, Man4-H2), 2.97 (bdd, AsN-βCH), 2.72 (dd, NeuAc7-H3eq, NeuAc7-H3eq), 2.64 (bdd, AsN-βCH), 2.15 (s×5, —Ac), 1.79 (dd, NeuAc7-H3ax, NeuAc7'-H3ax)

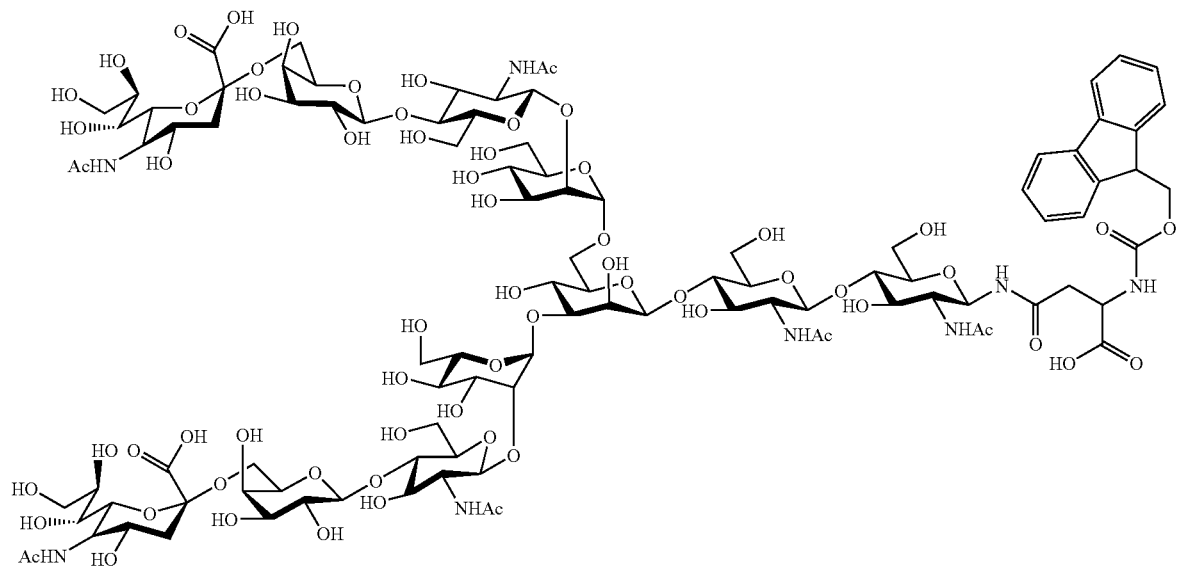

(1)

The structure of the above oligosaccharide is shown below. NeuAc: sialic acid, Gal: D-galactose, GlcNAc: N-acetylglucosamine, Man: D-mannose, Asn: asparagine (1-a)

NeuAc α2 ⟶ 6Gal β1 ⟶ 4GlcNac β1 ⟶

NeuAc α2 ⟶ 6Gal β1 ⟶ 4GlcNac β1 ⟶

The physical data for the resulting Compound 4 are as follows.

$^1$H-NMR(D$_2$O, 30° C.)

7.99 (2H, d, Fmoc), 7.79 (2H, d, Fmoc), 7.55 (4H, m, Fmoc), 5.12 (1H, s, Man4-H1), 5.06 (1H, d, GlcNAc1-H1), 4.93 (1H, s, Man4'-H1), 4.82 (1H, s, Man3-H1), 4.69 (1H, d, GlcNAc2-H1), 4.67 (2H, d, GlcNAc5,5'-H1), 4.53 (2H, d, Gal6,6'-H1), 4.34 (1H, d, Man3-H2), 4.27 (1H, d, Man4'-H2), 4.19 (1H, d, Man4-H2), 3.03 (1H, bdd, AsN-βCH), 3.00 (1H, bdd, AsN-βCH), 2.15 (12H, s×4, —Ac); HRMS Calcd for C$_{81}$H$_{120}$N$_6$NaO$_{50}$[M+Na+] 1999.6930, found, 1999.6939

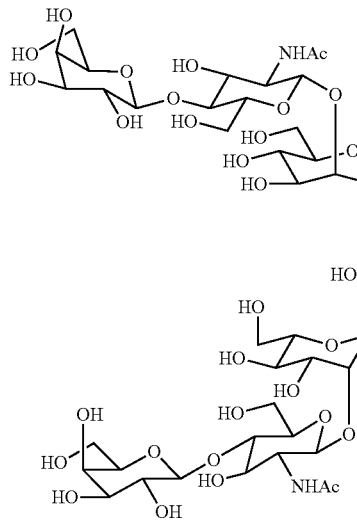
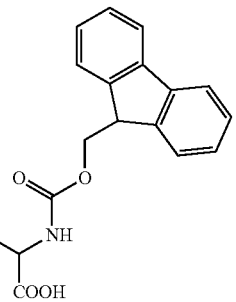

(4)

Table 2 gives the structure of Compound 4 as simplified.

Reference Example 3

Preparation and Isolation of Compounds 2 and 3

The mixture of Compounds 2 and 3 obtained in Reference Example 2 (5.0 mg, 2.2 μmol) were dissolved in 220 μL of water, and 100 μL of a 22 mM aqueous cesium carbonate was added thereto to adjust its pH 7.0. This solution was freeze dried. Four-hundred and thirty microliters of N,N-dimethylformamide was added to the solid obtained after drying, and further 20 μL of a 6.6 μmol benzyl bromide/N,N-dimethylformamide solution was added thereto. This solution was stirred under argon atmosphere. After 48 hours, the disappearance of the starting material was confirmed by TLC (eluent: 1M $NH_4OAc$:isopropanol=1:2), and thereafter 4.4 mL of diethyl ether was added to the solution to allow the compound to precipitate therefrom. The precipitated oligosaccharides were filtered, and the residual oligosaccharide was dissolved in water and freeze dried. The residue after the lyophilization was purified by fractional HPLC (YMC Packed Column D-ODS-5 S-5 120A ODS No. 2020178, 20×250 mm, eluent: 50 mM aqueous ammonium acetate acetonitrile=78:22, flow rate: 4 mL/min), and Compound 3 was eluted after 88 minutes and Compound 2 was eluted after 91 minutes. The fractions were collected, and further desalted on an ODS column (Cosmosil 75C18-OPN, 15×100 mm, eluted first with 50 mL of $H_2O$ and then with 25% acetonitrile), to give a benzyl derivative of Compound 2 in an amount of 1.6 mg and a benzyl derivative of Compound 3 in an amount of 1.8 mg.

A benzyl compound of Compound 2 (decasaccharide, 13.6 mg, 5.8 mmoles) was dissolved in 1.4 ml of NaOH aq. (pH=12) with ice cooling. The solution was stirred for about 8 hours while monitoring the reaction by HPLC. On completion of progress of the reaction, the reaction mixture was adjusted to a PH of 7.0 with 40 mM of HCl. The mixture resulting from neutralization was filtered by a membrane filter, followed by concentration, and fractionation and purification by JPLC (YMC-pack ODS-AM, SH-343-5AM, 20×250 mm, AN/25 mM $AcONH_4$ buffer=20/80, 7.0 ml/min., wave length: 274 nm). The fraction obtained was concentrated and passed through an ODS column (Cosmoseal $75C_{18}$—OPN, product of NACALAI TESQUE, INC.) for a desalting treatment, followed by concentration and freeze-drying to obtain the desired product, i.e., Compound 2 (6.2 mg, 47.4%). The compound obtained had the following physical data. Table 1 shows the structure of Compound 2 as simplified.

$^1$H NMR (400 MHz, $D_2O$, 30° C., HOD=4.81)

δ 8.00 (d, 2H, J=7.2, Fmoc), 7.79 (d, 2H, J=7.2, Fmoc), 7.59 (dd, 2H, J=7.2, Fmoc), 7.53 (dd, 2H, J=7.2, Fmoc), 5.22 (s, 1H, Man4-H1), 5.09 (d, 1H, J=9.8, GlcNAc1-H1), 5.01 (s, 1H, Man4'-H-1), 4.85 (s, 1H), 4.58-4.75 (m, 5H), 4.57 (dd, 2H, J=8.0), 4.38-4.48 (m, 2H), 4.33 (s, 1H), 4.28 (bs, 1H, Man4-H2), 4.19 (bs, 1H), 2.64-2.85 (m, 3H, Asn-βCH×2, NeuAc7-H3eq), 2.16, 2.13, 2.12 (eachs, 12H, Ac×4), 1.98 (s, 3H, Ac), 1.80 (dd, 1H, Ja=12.0, Jb=12.0, NeuAc7-H3ax).

A benzyl compound of Compound 3 (decasaccharide, 5.0 mg, 2.1 mmoles) was dissolved in 2.0 ml of NaOH aq. (pH=12) with ice cooling. The solution was stirred for about 5 hours while monitoring the reaction by HPLC. On completion of progress of the reaction, the reaction mixture was adjusted to PH 7.0 with 40 mM of HCl. The neutralized mixture was filtered with a membrane filter, followed by concentration, and fractionation and purification by JPLC (YMC-pack ODS-AM, SH-343-5AM, 20×250 mm, AN/25 mM $AcONH_4$ buffer=20/80, 7.0 ml/min., wave length: 274 nm). The fraction obtained was concentrated and passed through an ODS column (Cosmosil $75C_{18}$—OPN, product of NACALAI TESQUE, INC.) for a desalting treatment, followed by concentration and freeze-drying to obtain the desired product, i.e., Compound 3 (2.5 mg, 52.0%) The compound obtained had the following physical data. Table 1 shows the structure of Compound 3 as simplified.

$^1$H NMR (400 MHz, $D_2O$, 30%, HOD=4.81)

δ 8.01 (d, 2H, J=7.6, Fmoc), 7.80 (d, 2H, J=7.6, Fmoc), 7.59 (dd, 2H, J=7.6, Fmoc), 7.52 (dd, 2H, J=7.6, Fmoc), 5.21 (s, 1H, Man4-H1), 5.09 (d, 1H, J=9.5, GlcNAc1-H1), 5.03 (s, 1H, Man4'-H-1), 4.58-4.71 (m, 5H), 4.54 (t, 2H, J=7.5), 4.40-4.50 (b, 2H), 4.34 (s, 1H), 4.28 (bs, 1H, Man4-H2), 4.19 (bs, 1H), 2.70-2.85 (m, 2H, Asn-βCH, NeuAc7-H3eq), 2.55-2.70 (m, 1H, Asn-βCH), 2.16, 2.15, 2.13, 2.11 (eachs, 12H, Ac×4), 1.98 (s, 3H, Ac), 1.80 (dd, 1H, Ja=12.4, Jb=12.4, NeuAc7-H3ax).

Reference Example 4

Preparation of Compounds 5 and 6

The mixture (224 mg, 97 μmol) of Compounds 2 and 3 obtained in Reference Example 2 and 24 mg of bovine serum albumin were dissolved in 22 ml of HEPES buffer (50 mM, pH 6.0), and *Diplococcus pneumoniae*-derived β-galactosidase (1.35 U) was added thereto. This solution was allowed to stand at 37° C. for 15 hours, and thereafter freeze dried. The residue was purified by HPLC (ODS column, 2.0 φ×25 cm, eluent: 50 mM aqueous ammonium acetate:acetonitrile=85: 15, flow rate: 3 ml/min), and Compound 5 was eluted after 129 minutes, and Compound 6 was eluted after 134 minutes. Each of the fractions was collected and freeze dried. Subsequently, the fraction was desalted by HPLC (ODS column, 2.0 φ×25 cm, eluent:water for a first 15 minutes, and applied to a gradient of water:acetonitrile of from 10:0 to 85:15 (volume ratio) for a period of from 16 to 30 minutes, and then to a gradient of water:acetonitrile from 85:15 to 80:20 for a period of from 31 to 45 minutes; flow rate: 3.0 ml/min), to give a desired Compound 5 in an amount of 81 mg and Compound 6 in an amount of 75 mg. The physical data for the resulting compound 5 are as follows.

$^1$H-NMR (D$_2$O, 30° C.)

7.99 (2H, d, Fmoc), 7.79 (2H, d, Fmoc), 7.55 (4H, m, Fmoc), 5.15 (1H, S, Man4-H1), 5.06 (1H, d, GlcNAc1-H1), 4.95 (1H, s, Man4'-H1), 4.82 (1H, s, Man3-H1), 4.69 (1H, d, GlcNAc2-H1), 4.67 (2H, d, GlcNAc5,5'-H1), 4.53 (1H, d, Gal6'-H1), 4.34 (1H, d, Man3-H2), 4.27 (1H, d, Man4'-H2), 4.19 (1H, d, Man4-H2), 2.97 (1H, bdd, AsN-βCH), 2.76 (1H, dd, NeuAc7'-H3eq), 2.61 (1H, bdd, AsN-βCH), 2.15 (15H, s×5, —Ac), 1.79 (1H, dd, NeuAc7'-H3ax); HRMS Calcd for C$_{86}$H$_{127}$N$_7$NaO$_{53}$[M+Na+] 2128.7356, found, 2128.7363

The physical data for the resulting Compound 6 are as follows.

$^1$H-NMR (D$_2$O, 30° C.)

7.99 (2H, d, Fmoc), 7.79 (2H, d, Fmoc), 7.55 (4H, m, Fmoc), 5.15 (1H, S, Man4-H1), 5.06 (1H, d, GlcNAc1-H1), 4.95 (1H, s, Man4'-H1), 4.82 (1H, s, Man3-H1), 4.69 (1H, d, GlcNAc2-H1), 4.67 (2H, d, GlcNAc5,5'-H1), 4.53 (1H, d, Gal6-H1), 4.34 (1H, d, Man3-H2), 4.27 (1H, d, Man4'-H2), 4.19 (1H, d, Man4-H2), 2.97 (1H, bdd, AsN-βCH), 2.76 (1H, dd, NeuAc7-H3eq), 2.60 (1H, bdd, AsN-βCH), 2.15 (15H, s×5, —Ac), 1.79 (1H, dd, NeuAc7-H3ax); HRMS Calcd for C$_{86}$H$_{125}$N$_7$Na$_3$O$_{53}$[M+Na+] 2172.6995, found, 2172.7084

Reference Example 5

Preparation of Compounds 7 and 8

A mixture (90 mg, 47.3 μmol) of Compounds 5 and 6 obtained in Reference Example 4 was dissolved in 8.1 ml of HEPES buffer (50 mM, pH 6.0) together with 8 mg of bovine serum albumin without separating the compounds from each other, and 2.88 U of a bovine kidney-derived β-glucosaminidase (manufactured by Sigma-Aldrich Corporation, from bovine kidney) was added thereto. This solution was allowed to stand at 37° C. for 18 hours, and thereafter freeze dried. The residue was purified by HPLC (ODS column, 2.0 φ×25 cm, eluent: 50 mM aqueous ammonium acetate:methanol=65:35, flow rate: 3 ml/min), and Compound 7 was eluted after 117 minutes, and Compound 8 was eluted after 127 minutes. Each of the fractions was collected and freeze dried. Subsequently, the fraction was desalted by HPLC (ODS column, 2.0 φ×25 cm, eluent: water for a first 15 minutes, and applied to a gradient of water:acetonitrile of from 10:0 to 85:15 for a period of from 16 to 30 minutes, and then to a gradient of water:acetonitrile of from 85:15 to 80:20 for a period of from 31 to 45 minutes; flow rate: 3.0 ml/min), to give a desired Compound 7 in an amount of 40 mg and Compound 8 in an amount of 37 mg. The physical data for the resulting Compound 7 are as follows.

$^1$H-NMR (D$_2$O, 30° C.)

8.01 (2H, d, Fmoc), 7.80 (2H, d, Fmoc), 7.56 (4H, m, Fmoc), 5.22 (1H, s, Man4-H1), 5.08 (1H, d, GlcNAc1-H1), 4.94 (1H, s, Man4'-H1), 4.84 (1H, s, Man3-H1), 4.69 (1H, d, GlcNAc2-H1), 4.67 (1H, d, GlcNAc5-H1), 4.55 (1H, d, Gal6-H1), 4.33 (1H, dd, Man3-H2), 4.20 (1H, dd, Man4-H2), 4.15 (1H, dd, Man4'-H2), 2.97 (1H, bdd, AsN-βCH), 2.76 (2H, dd, NeuAc7,7'-H3eq), 2.62 (1H, bdd, AsN-βCH), 2.15 (12H, s×4, —Ac), 1.79 (2H, dd, NeuAc7,7'-H3ax); HRMS Calcd for C$_{78}$H$_{114}$N$_6$NaO$_{48}$[M+Na+] 1925.6562, found, 1925.6539

The physical data for the resulting Compound 8 are as follows.

$^1$H-NMR (D$_2$O, 30° C.)

7.99 (2H, d, Fmoc), 7.79 (2H, d, Fmoc), 7.55 (4H, m, Fmoc), 5.15 (1H, S, Man4-H1), 5.06 (1H, d, GlcNAc1-H1), 4.95 (1H, s, Man4'-H1), 4.82 (1H, s, Man3-H1), 4.69 (1H, d, GlcNAc2-H1), 4.67 (2H, d, GlcNAc5,5'-H1), 4.53 (2H, d, Gal6,6'-H1), 4.34 (1H, d, Man3-H2), 4.27 (1H, d, Man4'-H2), 2.97 (1H, bdd, AsN-βCH2), 2.76 (1H, dd, NeuAc7'-H3eq), 2.61 (1H, bdd, AsN-βCH2), 2.15 (12H, s×4, —Ac), 1.79 (1H, dd, NeuAc7'-H3ax); HRMS Calcd for C$_{78}$H$_{114}$N$_6$NaO$_{48}$[M+Na+] 1925.6562, found, 1925.6533

Reference Example 6

Preparation of Compound 9

Compound 7 (30 mg, 473 μmol) obtained in Reference Example 5 and 3 mg of bovine serum albumin were dissolved in 6 ml of HEPES buffer (50 mM, pH 6.0), and 10 U of Jack Beans-derived α-mannosidase was added thereto. This solution was allowed to stand at 37° C. for 21 hours, and then freeze dried. Subsequently, the residue was purified by HPLC (ODS column, 2.0 φ×25 cm, eluent:water for a first 15 minutes, and applied to a gradient of water:acetonitrile of from 10:0 to 85:15 for a period of from 16 to 30 minutes, and then to a gradient of water:acetonitrile of from 85:15 to 80:20 for a period of from 31 to 45 minutes; flow rate: 3.0 ml/min), to give 20 mg of a desired Compound 9. The physical data for the resulting Compound 9 are as follows.

$^1$H-NMR (D$_2$O, 30° C.)

8.01 (2H, d, Fmoc), 7.80 (2H, d, Fmoc), 7.56 (4H, m, Fmoc), 5.00 (1H, d, GlcNAc1-H1), 4.95 (1H, s, Man4'-H1), 4.84 (1H, s, Man3-H1), 4.67 (1H, d, GlcNAc2-H1), 4.56 (1H, d, GlcNAc5-H1), 4.44 (1H, d, Gal6-H1), 4.11 (1H, dd, Man4'-H2), 4.07 (1H, dd, Man3-H2), 2.97 (1H, bdd, AsN-βCH), 2.76 (1H, dd, NeuAc7'-H3eq), 2.62 (1H, bdd, AsN-βCH), 2.15 (12H, s×4, —Ac), 1.79 (2H, dd, NeuAc7'-H3ax); HRMS Calcd for C$_{72}$H$_{104}$N$_6$NaO$_{43}$[M+Na+] 1763.6034, found, 1763.6074

Reference Example 7

Preparation of Compound 10

Compound 8 (40 mg, 630 μmol) obtained in Reference Example 5 and 5 g of bovine serum albumin were dissolved in 7.8 ml of HEPES buffer (50 mM, pH 6.0), and 38 U of a Jack Beans-derived α-mannosidase was added thereto. This solution was allowed to stand at 37° C. for 63 hours, and then freeze dried. Subsequently, the residue was purified by HPLC (ODS column, 2.0 φ×25 cm, eluent: water for a first 15 minutes, and applied to a gradient of water:acetonitrile of from 10:0 to 85:15 for a period of from 16 to 30 minutes, and then to a gradient of water:acetonitrile of from 85:15 to 80:20 for a period of from 31 to 45 minutes; flow rate: 3.0 ml/min, to give 30 mg of a desired Compound 10. The physical data for the resulting Compound 10 are as follows.

$^1$H-NMR (D$_2$O, 30%)

8.01 (2H, d, Fmoc), 7.80 (2H, d, Fmoc), 7.56 (4H, m, Fmoc), 5.23 (1H, s, Man4-H1), 5.08 (1H, d, GlcNAc1-H1), 4.53 (1H, d, Gal6-H1), 4.32 (1H, dd, Man3-H2), 4.28 (1H, dd, Man4-H2), 2.81 (1H, bdd, AsN-βCH), 2.76 (1H, dd, NeuAc7-H3eq), 2.59 (1H, bdd, AsN-βCH), 2.13 (12H, s×4, —Ac), 1.80 (1H, dd, NeuAc7H3ax); HRMS Calcd for C$_{72}$H$_{104}$N$_6$NaO$_{43}$[M+Na+] 1763.6034, found, 1763.6041

Reference Example 8

Preparation of Compound 11

Compound 5 (28 mg, 21.3 μmol) and 1.0 mg of bovine serum albumin were dissolved in HEPES buffer (50 mM, pH 5.0, 454 μL), and neuraminidase (manufactured by Sigma-Aldrich Corporation, from *Viblio Cholerae*, 198 mU) was added thereto. This solution was allowed to stand at 37° C. for 20 hours, and thereafter the termination of the reaction was confirmed by HPLC analysis. The reaction solution was purified by HPLC (YMC Packed Column D-ODS-5 S-5 120A ODS No. 2020178, 20×250 mm, eluent: 50 mM aqueous ammonium acetate:acetonitrile=80:20, flow rate: 4 mL/min). Further, the residue was desalted on ODS column (Cosmosil 75C18-OPN, 15×100 mm, eluted first with 50 mL of H$_2$O and then with 25% acetonitrile), to give a desired Compound 11 (17 mg, yield: 70%). The physical data for the resulting compound are as follows. Table 2 shows the structure of Compound 11 as simplified.

$^1$H-NMR (30° C.)

δ7.91 (d, 2H, J=7.5 Hz, Fmoc), 7.71 (d, 2H, J=7.5 Hz, Fmoc), 7.51 (dd, 2H, J=7.5 Hz, Fmoc), 7.43 (dd, 2H, J=7.5 Hz, Fmoc), 5.12 (s, 1H, Man4-H1), 4.99 (d, 1H, J=9.5 Hz, GlcNAc1-H-1), 4.92 (s, 1H, Man4'-H-1), 4.76 (s, 1H, Man3-H-1), 4.58 (d, 1H, J=8.0 Hz, GlcNAc2-H-1), 4.55 (d, 1H, J=8.4 Hz, GlcNAc5'-H-1), 4.47 (d, 1H, J=7.8 Hz, Gal6'-H-1), 4.34 (t, 1H, Fmoc), 4.24 (bd, 1H, J=1.9 Hz, Man3-H-2), 4.18 (bdd, 1H, J=1.4 Hz, 3.3 Hz, Man4-H-2), 4.11 (bdd, 1H, J=1.4 Hz, 3.5 Hz, Man4'-H-2), 2.72 (bdd, 1H, J=3.0 Hz, 15.7 Hz, AsN-βCH), 2.52 (bdd, 1H, J=8.7 Hz, 15.7 Hz, AsN-βCH), 2.06, 2.05, 2.04, 1.89 (each s, each 3H, Ac); HRMS Calcd for C$_{75}$H$_{110}$N$_6$NaO$_{45}$[M+Na+] 1837.6402, found 1837.6471

Reference Example 9

Preparation of Compound 12

Compound 6 (20 mg, 9.4 μmol) and 1.6 mg of bovine serum albumin were dissolved in HEPES buffer (50 mM, pH 5.0, 323 μL), and neuraminidase (manufactured by Sigma-Aldrich Corp., from *Viblio Cholerae*, 141 mU) was added thereto. This solution was allowed to stand at 37° C. for 18 hours, and thereafter the termination of the reaction was confirmed by HPLC analysis. Subsequently, the reaction solution was purified by HPLC (YMC Packed Column D-ODS-5 S-5 120A ODS No. 2020178, 20×250 mm, eluent: 50 mM aqueous ammonium acetate:acetonitrile=80:20, flow rate: 4 mL/min). Further, the residue was desalted on an ODS column (Cosmosil 75C18-OPN, 15×100 mm, eluted first with 50 mL of H$_2$O and then with 25% acetonitrile), to give a desired Compound 12 (13 mg, yield: 76%). The structure of the resulting compound was confirmed from the finding that its $^1$H-NMR was identical to that of the standard compound. Table 2 shows the structure of Compound 12 as simplified.

Reference Example 10

Preparation of Compound 13

Compound 7 (45 mg, 24 μmol) and 1.7 mg of bovine serum albumin were dissolved in HEPES buffer (50 mM, pH 5.0, 820 μL), and neuraminidase (manufactured by Sigma-Aldrich Corp., from *Viblio Cholerae*, 134 mU) was added thereto. This solution was allowed to stand at 37° C. for 14 hours, and thereafter the termination of the reaction was confirmed by HPLC analysis. Subsequently, the reaction solution was purified by HPLC (YMC Packed Column D-ODS-5 S-5 120A ODS No. 2020178, 20×250 mm, eluent: 50 mM aqueous ammonium acetate:acetonitrile=80:20, flow rate: 4 mL/min). Further, the residue was desalted on an ODS column (Cosmosil 75C18-OPN, 15×100 mm, eluted first with 50 mL of H$_2$O and then with 25% acetonitrile), to give a desired Compound 13 (28 mg, yield: 74%). The physical data for the resulting compound are as follows. Table 2 shows the structure of Compound 13 as simplified.

$^1$H-NMR (30° C.)

δ7.92 (d, 2H, J=7.5 Hz, Fmoc), 7.71 (d, 2H, J=7.5 Hz, Fmoc), 7.51 (dd, 2H, J=7.5 Hz, Fmoc), 7.44 (dd, 2H, J=7.5 Hz, Fmoc), 5.10 (s, 1H, Man4-H-1), 4.99 (d, 1H, J=9.5 Hz, GlcNAc1-H-1), 4.92 (s, 1H, Man4'-H-1), 4.76 (s, 1H, Man3-H-1), 4.58 (d, 2H, GlcNAc2,5'-H-1), 4.47 (d, 1H, J=8.0 Hz, Gal6'-H-1), 4.35 (t, 1H, Fmoc), 4.24 (bd, 1H, J=1.9 Hz, Man3-H-2), 4.11 (bs, 1H, Man4'-H-2), 4.07 (bs, 1H, Man4-H-2), 2.72 (bd, 1H, J=15.5 Hz, AsN-βCH), 2.52 (bdd, 1H, J=8.7 Hz, 15.5 Hz, AsN-βCH), 2.06, 2.04, 1.89 (each s, each 3H, Ac); HRMS Calcd for C$_{67}$H$_{97}$N$_5$NaO$_{40}$[M+Na+ 1634.5608, found, 1634.5564

Reference Example 11

Preparation of Compound 14

Compound 8 (47 mg, 25 μmol) and 1.9 mg of bovine serum albumin were dissolved in HEPES buffer (50 mM, pH 5.0, 840 μL), and neuraminidase (manufactured by Sigma-Aldrich Corp., from *Viblio Cholerae*, 369 mU) was added thereto. This solution was allowed to stand at 37° C. for 37 hours, and thereafter the termination of the reaction was confirmed by HPLC analysis. The reaction solution was freeze dried, and the freeze dried product was subsequently purified by HPLC (YMC Packed Column D-ODS-5 S-5 120A ODS No. 2020178, 20×250 mm, eluent: 50 mM aqueous ammonium acetate:acetonitrile=80:20, flow rate: 4 mL/min). Further, the residue was desalted on an ODS column (Cosmosil 75C18-OPN, 15×100 mm, eluted first with 50 mL of H$_2$O and then with 25% acetonitrile), to give a desired Compound 14 (26 mg, yield: 65%). The physical data for the resulting compound are as follows. Table 2 shows the structure of Compound 14 as simplified.

$^1$H-NMR (30° C.)

δ7.92 (d, 2H, J=7.5 Hz, Fmoc), 7.71 (d, 2H, J=7.5 Hz, Fmoc), 7.51 (dd, 2H, J=7.5 Hz, Fmoc), 7.43 (dd, 2H, J=7.5 Hz, Fmoc), 5.12 (s, 1H, Man4-H1), 4.99 (d, 1H, J=9.4 Hz, GlcNAc1-H1), 4.91 (s, 1H, Man4'-H1), 4.77 (s, 1H, Man3-H-1), 4.57 (bd, 2H, GlcNAc2,5'-H-1), 4.46 (d, 1H, J=7.5 Hz, Gal6'-H-1), 4.34 (t, 3H, Fmoc), 4.24 (bs, 1H, Man4'-H-2), 4.19 (bs, 1H, Man4-H-2), 2.72 (bd, 1H, J=15.5 Hz, AsN-βCH), 2.52 (bdd, 1H, J=9.2 Hz, 15.5 Hz, AsN-βCH), 2.06, 2.05, 1.89 (each s, each 3H, Ac); HRMS Calcd for $C_{67}H_{97}N_5NaO_{40}[M+Na+]$ 1634.5608, found, 1634.5644

Reference Example 12

Preparation of Compound 15

Compound 9 (32 mg, 18.4 μmol) and 2.5 mg of bovine serum albumin were dissolved in HEPES buffer (50 mM, pH 5.0, 713 μL), and neuraminidase (manufactured by Sigma-Aldrich Corp., from *Viblio Cholerae*, 134 mU) was added thereto. This solution was allowed to stand at 37° C. for 17 hours, and thereafter the termination of the reaction was confirmed by HPLC analysis. Subsequently, the reaction solution was purified by HPLC (YMC Packed Column D-ODS-5 S-5 120A ODS No. 2020178, 20×250 mm, eluent: 50 mM aqueous ammonium acetate:acetonitrile=80:20, flow rate: 4 mL/min). Further, the residue was desalted on an ODS column (Cosmosil 75C18-OPN, 15×100 mm, eluted first with 50 mL of $H_2O$ and then with 25% acetonitrile), to give a desired Compound 15 (13 mg, yield: 52%). The physical data for the resulting compound are as follows. Table 2 shows the structure of Compound 15 as simplified.

$^1$H-NMR (30° C.)

δ7.92 (d, 2H, J=7.5 Hz, Fmoc), 7.71 (d, 2H, J=7.5 Hz, Fmoc), 7.51 (dd, 2H, J=7.5 Hz, Fmoc), 7.44 (dd, 2H, J=7.5 Hz, Fmoc), 5.00 (d, 1H, J=9.9 Hz, GlcNAc1-H-1), 4.92 (s, 1H, Man4'-H-1), 4.75 (s, 1H, Man3-H-1), 4.58 (d, 2H, J=7.5 Hz, GlcNAc2,5'-H-1), 4.47 (d, 1H, J=7.8 Hz, Gal6'-H-1), 4.34 (t, 1H, Fmoc), 4.10 (bd, 1H, Man3-H-2), 4.07 (bs, 1H, Man4'-H-2), 2.72 (bdd, 1H, J=15.5 Hz, AsN-βCH), 2.52 (bdd, 1H, J=9.2 Hz, 15.5 Hz, AsN-βCH), 2.07, 2.05, 1.89 (each s, each 3H, Ac); MS (Fab), Calcd for $C_{61}H_{88}N_5O_{35}[M+H+]$1450.5, found, 1450.3

Reference Example 13

Preparation of Compound 16

Compound 10 (28 mg, 16 μmol) and 1.7 mg of bovine serum albumin were dissolved in HEPES buffer (50 mM, pH 5.0, 624 μL), and neuraminidase (manufactured by Sigma-Aldrich Corp., from *Viblio Cholerae*, 117 mU) was added thereto. This solution was allowed to stand at 37° C. for 17 hours, and thereafter the termination of the reaction was confirmed by HPLC analysis. Subsequently, the reaction solution was purified by HPLC (YMC Packed Column D-ODS-5 S-5 120A ODS No. 2020178, 20×250 mm, eluent: 50 mM aqueous ammonium acetate:acetonitrile=80:20, flow rate: 4 mL/min). Further, the residue was desalted on an ODS column (Cosmosil 75C18-OPN, 15×100 mm, eluted first with 50 mL of $H_2O$ and then with 25% acetonitrile), to give a desired Compound 16 (14.6 mg, yield: 68%). The physical data for the resulting compound are as follows. Table 2 shows the structure of Compound 16 as simplified.

$^1$H-NMR (30° C.)

δ7.92 (d, 2H, J=7.5 Hz, Fmoc), 7.71 (d, 2H, J=7.5 Hz, Fmoc), 7.50 (dd, 2H, J=7.5 Hz, Fmoc), 7.43 (dd, 2H, J=7.5 Hz, Fmoc), 5.12 (s, 1H, Man4-H-1), 4.99 (d, 1H, J=9.5 Hz, GlcNAc1-H-1), 4.77 (s, 1H, Man3-H-1), 4.57 (d, 2H, J=7.2 Hz, GlcNAc2-H-1), 4.46 (d, 1H, J=7.8 Hz, Gal6-H-1), 4.34 (G Fmoc), 4.22 (bd, 1H, J=2.7 Hz, Man3-H-2), 4.19 (b, 1H, Man4-H-2), 2.72 (bdd, 1H, J=15.5 Hz, AsN-βCH), 2.52 (bdd, 1H, J=9.8 Hz, 15.5 Hz, AsN-βCH), 2.05 (s, 6H, Ac×2), 1.89 (s, 3H, Ac); MS (Fab), Calcd for $C_{61}H_{88}N_5O_{35}[M+H+]$ 1450.5, found, 1450.3

Reference Example 14

Preparation of 5-acetamide-3,5,7-trideoxy-7-fluoro-D-glycero-β-D-galacto-2-nonulopyranosidonic acid 25, 7-fluorosialic acid

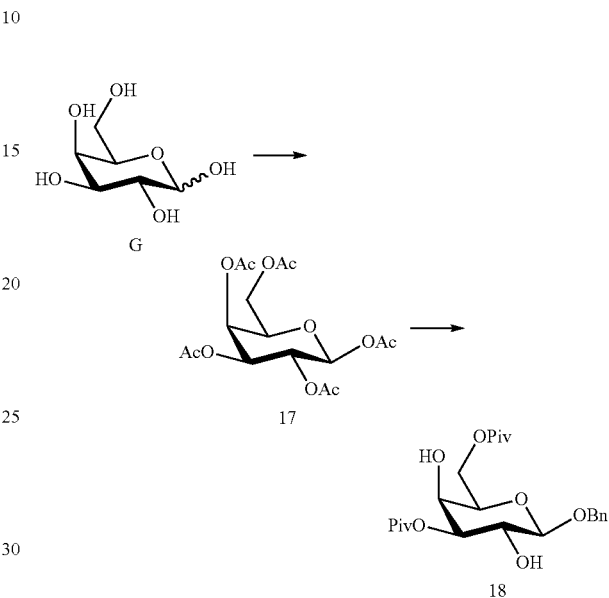

(1) Preparation of Compound 17

Sodium acetate (5 g, 69 mmols) was dissolved in acetic anhydride (60 ml), the solution was heated, and D-galactose (G) (10 g, 55 mmols) was thereafter added in small portions to the solution. The mixture was refluxed with heating for 2 hours, and the completion of reaction was thereafter recognized by TLC (toluene:ethyl acetate=5:1). The reaction mixture was returned to room temperature and then poured into 300 cc of ice water. The resulting precipitate was collected by filtration. The precipitate was dissolved in ethanol (14 ml) for recrystallization, giving 9.0 g of Compound 17 (41% in yield).

(2) Preparation of Compound 18

Compound 17 (4.3 g, 11 mmols) was dissolved in methylene chloride (120 ml), and the solution was thereafter cooled to −20° C. under an argon stream. Subsequently, tin tetrachloride (3.1 g, 12 mmols) was added to the solution, the mixture was stirred for 20 minutes, benzyl alcohol (2.3 g, 22 mmols) was then added to the mixture, and the reaction temperature was returned to room temperature. After the completion of reaction was recognized by TLC (hexane:ethyl acetate=1:1), the reaction mixture was poured into a saturated aqueous solution of sodium hydrogencarbonate, followed by extraction with methylene chloride. The methylene chloride layer was dried over anhydrous magnesium sulfate, then filtered and concentrated in a vacuum. The residue was dried in a desiccator, thereafter dissolved in distilled methanol (80 ml), sodium methoxide (431 mg, 5.5 mmols) was added to the solution, and the mixture was stirred under an argon stream. After the completion of reaction was recognized by TLC (ethyl acetate:methanol:water=10:5:1), the reaction mixture was neutralized with a cation-exchange resin IR-120(+) to terminate the reaction. The resin was filtered off for removal, and the filtrate was concentrated in a vacuum. The residue was dried in a desiccator, thereafter dissolved in pyridine (44 ml), and the reaction mixture was cooled to 0° C. Trimethylacetyl chloride (4.6 g, 38.5 mmols) was added to the reaction mixture, and the mixture was returned to room temperature and stirred under an argon stream for 1 hour. After the completion of reaction was recognized by TLC (hexane:ethyl acetate=2:1), the reaction mixture was cooled to 0° C., and methanol was thereafter added to the mixture to terminate the reaction. The reaction mixture was concentrated as it was in a vacuum, the residue was then dissolved in ethyl acetate, the solution was washed with a saturated aqueous solution of sodium chloride and water, and dried over anhydrous magnesium sulfate to evaporate off the ethyl acetate. After the magnesium sulfate was removed by filtration, the filtrate was concentrated in a vacuum. The residue was purified by silica gel column chromatography (eluent: hexane:ethyl acetate=2:1), giving Compound 18 (2.8 g, yield 58%).

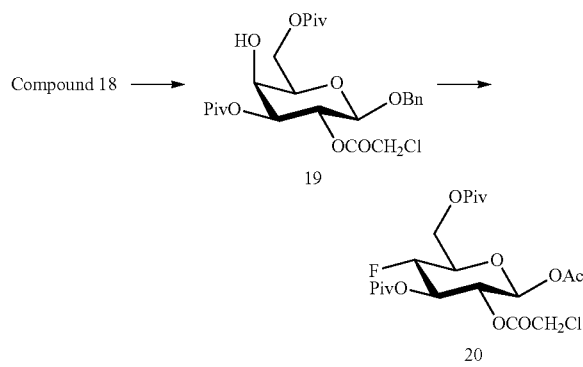

(3) Preparation of Compound 19

Compound 18 (200 mg, 0.455 mmols) was dissolved in dichloromethane (7.8 ml) and pyridine (1.3 ml), chloroacetic anhydride (155 mg, 0.91 mmol) was added to the solution, and the mixture was reacted with stirring at −15° C. under an argon stream for 15 minutes. After the completion of reaction was recognized, the chloroacetic anhydride was quenched with methanol (5 ml), and the reaction mixture was azeotropically boiled with toluene three times for concentration in vacuum. The residue was extracted with ethyl acetate, and the extract was washed with a saturated aqueous solution of sodium chloride. The organic layer was dried over anhydrous magnesium sulfate, followed by filtration and concentration. The residue was purified by silica gel column chromatography (ethyl acetate:hexane=1:4), giving Compound 19 (172 mg, yield 73.5%).

$^1$H-NMR (400 MHz, CDCl$_3$)

δ7.37-7.29 (m, 5H, Ph), 5.39 (dd, 1H, $J_{1,\,2}$=8.0 Hz, $J_{2,\,3}$=10.4 Hz, H-2) 4.89 (dd, 1H, $J_{3,\,4}$=3.4 Hz, H-3), 4.89, 4.62 (2d, 2H, J=12.5 Hz, OCH$_2$Ph), 4.53 (d, 1H, H-1), 4.37 (dd, 1H, $J_{6a,\,6b}$=11.5 Hz, $J_{6a,\,5}$=6.0 Hz, H-6a), 4.32 (dd, 1H, $J_{6b,\,5}$=6.6 Hz, H-6b), 4.00 (m, 1H, H-4), 3.92 (s, 2H, COCH$_2$Cl), 3.75 (dd, 1H, H-5), 1.23, 1.19 [2s, 18H, COC(CH$_3$)$_3$]

$^{13}$C-NMR (400 MHz, CDCl$_3$)

δ 178.33, 177.57, 165.92, (C=O), 136.66, 128.48, 128.07, 127.89 (Ph), 99.16 (C-1), 72.82 (C-3), 72.35 (C-5), 70.92 (C-2), 70.49 (OCH$_2$Ph), 67.29 (C-4), 62.30 (C-6), 40.40 (COCH$_2$Cl), 38.95, 38.80 [COC(CH$_3$)$_3$], 27.14, 26.98 [COC(CH$_3$)$_3$]

$^1$H-NMR and $^{13}$C-NMR were measured using Bruker's AVANCE 400 (mentioned as 400 MHz). When the solvent was deuteriochloroform, trimethylsilane was used as internal standard. When other deuteriated solvents were used, the peak of the solvent was used as a reference. Chemical shifts were indicated by δ (ppm), and the coupling constants by J (Hz). Used for silica gel chromatography were Merck Silicagel 60, 70-230 mesh or 230-400 mesh, and spherical silica gel which was Silica Gel 60 (Spherical), product of Kanto Chemical Co., Ltd. Used for detecting reactions (for TLC) was DC-Platten Kieselgel 60 F254 (Artl, 05715), product of E. Merk. The columns used for high performance chromatography (HPLC) were Cosmosil 5C$_{18}$-AR Packed Column [φ4.6×150 mm], product of NACALAI TESQUE, INC. The spectrophotofluorometer used was FP-210 Spectrofluorometer, product of JASCO.

(4) Preparation of Compound 20

Compound 19 (300 mg, 0.583 mmol) was dissolved in dichloromethane (5.8 ml), and diethylaminosulfatrifluoride (DAST) was added to the solution with stirring under an argon stream at −15° C. The mixture was returned to room temperature 10 minutes after the addition of DAST and reacted for 1 hour. Disappearance of the material was confirmed by TLC, the DAST was quenched with methanol (3 ml), and the reaction mixture was concentrated in a vacuum. The residue was purified by silica gel chromatography (ethyl acetate:hexane=1:6), giving Compound 20 (211 mg, yield 70%).

$^1$H-NMR (400 MHz, CDCl$_3$)

δ 7.37-7.27 (m, 5H, Ph), 5.31 (ddd, 1H, $J_{3,\,F}$=14.3 Hz, $J_{3,\,4}$=9.69 Hz, $J_{2,\,3}$=9.63 Hz, H-3), 5.04 (dd, 1H, $J_{1,\,2}$=7.93 Hz, H-2), 4.86 (d, 1H, J=12.2 Hz, OCH$_2$Ph), 4.60 (d, 1H, H-1), 4.59 (d, 1H, OCH$_2$Ph), 4.44 (ddd, 1H, $J_{4,\,5}$=9.04 Hz, $J_{4,\,F}$=50.6 Hz, H-4), 4.43 (ddd, 1H, $J_{6a,\,6b}$=12.1 Hz, $J_{6a,\,5}$=2.41 Hz, $J_{6a,\,F}$=2.23 Hz, H-6a), 4.24 (ddd, 1H, $J_{6b,\,5}$=5.67 Hz, $J_{6b,\,F}$=1.28 Hz, H-6b), 3.93 (s, 2H, OCOCH$_2$Cl), 3.75 (m, 1H, H-5), 1.25, 1.18 [2s, 18H, OCOC(CH$_3$)$_3$]

$^{13}$C-NMR (400 MHz, CDCl$_3$)

δ177.94, 117.43, 165.88 (C=O), 136.34, 128.55, 138.23, 127.92 (Ph), 98.68 (C-1), 87.35 (d, $J_{4,\,F}$=188.62 Hz, C-4), 72.65 (d, $J_{2,\,F}$=7.96 Hz, C-2), 72.05 (d, $J_{3,\,F}$=20.02 Hz, C-3), 71.49 (d, $J_{5,\,F}$=23.09 Hz, C-5), 70.80 (OCH$_2$Ph), 62.12 (C-6), 40.30 (OCOCH$_2$Cl), 38.87 [OCOC(CH$_3$)$_3$], 27.17, 26.92 [OCOC(CH$_3$)$_3$]

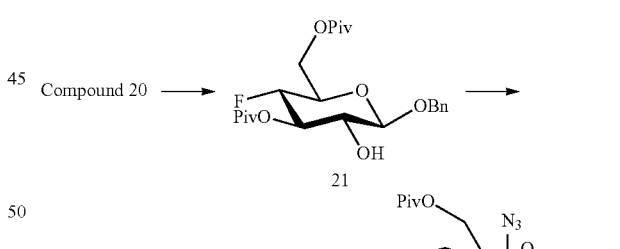

(5) Preparation of Compound 21

Compound 20 (625 mg, 1.21 mmols) was dissolved in methanol (24.2 ml), and sodium methoxide (13.1 mg, 0.6 mmol) was added to the solution with stirring under an argon stream at −15° C. Disappearance of the material was confirmed by TLC 30 minutes later, and the reaction mixture was neutralized (pH 6-7) with a cation-exchange resin IR-120(+). After the resin was filtered off, the filtrate was concentrated in a vacuum. The residue was purified by silica gel chromatography (ethyl acetate:hexane=1:4), giving Compound 21 (395 mg, yield 74%).

$^1$H-NMR (400 MHz, CDCl$_3$)

δ 7.38-7.29 (m, 5H, Ph), 5.18 (ddd, 1H, $J_{3,F}$=14.8 Hz, $J_{3,4}$=9.51 Hz, $J_{2,3}$=8.99 Hz, H-3), 4.90 (d, 1H, J=11.7, OCH$_2$Ph), 4.63 (d, 1H, OCH$_2$Ph), 4.47 (ddd, 1H, $J_{5,6a}$=2.43 Hz, $J_{6a,F}$=2.2 Hz, H-6a), 4.47 (d, 1H, $J_{1,2}$=7.7 Hz, H-1), 4.38 (ddd, 1H, $J_{4,5}$=8.96 Hz, $J_{3,4}$=9.67 Hz, $J_{4,F}$=50.8 Hz, H-4), 4.23 (ddd, 1H, $J_{6a,6b}$=12.0 Hz, $J_{6b,5}$=6.05 Hz, $J_{6b,F}$=1.26 Hz, H-6b), 3.75 (m, 1H, H-5), 3.54 (m, 1H, $J_{2,OH}$=2.70 Hz, H-2), 1.27, 1.26 [2s, 18H, OCOC(CH$_3$)$_3$]

$^{13}$C-NMR (400 MHz, CDCl$_3$)

δ 178.17, 177.94 (C=O), 136.54, 128.54, 128.17, 128.12 (Ph), 101.31 (C-1), 87.45 (d, $J_{4,F}$=187.39 Hz, C-4), 74.17 (d, $J_{3,F}$=18.88 Hz, C-3), 72.45 (d, $J_{2,F}$=7.56 Hz, C-2), 71.45 (d, $J_{5,F}$=23.26 Hz, C-5), 71.09 (OCH$_2$Ph), 62.44 (C-6), 38.90, 38.85 [OCOC(CH$_3$)$_3$], 27.14, 26.99 [OCOC(CH$_3$)$_3$]

(6) Preparation of Compound 22

To a solution of pyridine (22.2 μl, 0.274 mmol) in dichloromethane (370 μl) was added dropwise trifluoromethanesulfonic anhydride (46 μl, 0.274 mmol) at 0° C., and 15 minutes later, a solution of Compound 21 in dichloromethane (1 ml) was added dropwise to the mixture at 0° C. Disappearance of the material was confirmed by TLC, and the reaction mixture was diluted with dichloromethane. The organic layer was washed with a saturated aqueous solution of sodium hydrogencarbonate, saturated sodium chloride aqueous solution and water, dried over anhydrous magnesium sulfate and thereafter concentrated. The residue was further dried by a vacuum pump, and then dissolved in benzene (1 ml). Sodium azide (13 mg, 0.206 mmol) and tetraammonium chloride (57 mg, 0.206 mmol) were added to the solution under an argon stream at room temperature, and the mixture was reacted at 40° C. The disappearance of the material was confirmed by TLC, and the reaction mixture was thereafter concentrated in a vacuum. The residue was subjected to extraction with ethyl acetate, and the extract was washed with a saturated sodium chloride aqueous solution and water, dried over anhydrous magnesium sulfate and thereafter concentrated. The residue was purified by silica gel column chromatography (ethyl acetate:hexane=1:4), affording Compound 22 (30.4 mg, yield 95%).

$^1$H-NMR (400 MHz, CDCl$_3$)

δ 7.39-7.32 (m, 5H, Ph), 4.99 (ddd, 1H, $J_{3,F}$=13.18 Hz, $J_{3,4}$=9.27 Hz, $J_{2,3}$=3.87 Hz, H-3), 4.93 (d, 1H, J=12.07 Hz, OCH$_2$Ph), 4.67 (d, 1H, $J_{1,2}$=1.18 Hz, H-1), 4.63 (d, 1H, OCH$_2$Ph), 4.51 (ddd, 1H, $J_{6a,6b}$=11.95 Hz, $J_{6a,5}$=2.54 Hz, $J_{6a,F}$=2.08 Hz, H-6a), 4.23 (ddd, 1H, $J_{6b,5}$=6.14 Hz, $J_{6b,F}$=1.14 Hz, H-6b), 4.08 (m, 1H, H-2), 3.64 (m, 1H, H-5), 1.26 [2s, 18H, OCOC(CH$_3$)$_3$]

$^{13}$C-NMR (400 MHz, CDCl$_3$)

δ 178.01, 177.68 (C=O), 136.06, 128.63, 128.31, 128.14 (Ph), 97.25 (C-1), 85.51 (d, $J_{4,F}$=183.97 Hz, C-4), 72.01 (d, $J_{5,F}$=23.89, C-5), 71.73 (d, $J_{3,F}$=18.98, C-3), 70.57 (OCH$_2$Ph), 62.42 (C-2, C-6), 39.08, 38.90 [OCOC(CH$_3$)$_3$], 27.18, 26.95 [OCOC(CH$_3$)$_3$]

(7) Preparation of Compound 23

Compound 22 (180 mg, 0.387 mmol) was dissolved in methanol (8 ml), sodium methoxide (922 mg, 9.67 mmols) was added to the solution, and the mixture was reacted with stirring at 40° C. TLC revealed 4.5 hours later that the reaction mixture collected into a spot, and the mixture was neutralized with a cation-exchange resin IR-120(+), followed by filtration and concentration. The residue was purified by silica gel column chromatography (ethyl acetate:hexane=1:1), giving Compound 23 (105.3 mg, yield 91.6%).

$^1$H-NMR (400 MHz, CDCl$_3$)

δ 7.40-7.31 (m, 5H, Ph), 4.96 (d, 1H, J=12.13 Hz, OCH$_2$Ph), 4.71 (d, 1H, $J_{1,2}$=1.33 Hz, H-1), 4.69 (d, 1H, OCH$_2$Ph), 4.49 (ddd, 1H, $J_{4,F}$=51.06 Hz, $J_{4,5}$=9.19 Hz, $J_{3,4}$=9.20 Hz, H-4), 4.02 (m, 1H, H-2), 3.93 (dddd, 1H, $J_{6a,6b}$=12.19 Hz, $J_{6a,5}$=2.31 Hz, $J_{6a,F}$=2.32 Hz, $J_{6a,OH}$=6.20 Hz, H-6a), 3.89-3.77 (m, 2H, H-3, H-6b), 3.39 (m, 1H, H-5)

$^{13}$C-NMR (400 MHz, CDCl$_3$)

δ 136.39, 128.62, 128.24, 127.83 (Ph), 98.63 (C-1), 88.19 (d, $J_{4,F}$=178.91 Hz, C-4), 73.95 (d, $J_{5,F}$=25.48 Hz, C-5), 71.18 (OCH$_2$Ph), 71.16 (d, $J_{3,F}$=19.69 Hz, C-3), 64.48 (d, $J_{2,F}$=8.42 Hz, C-2), 61.39 (C-6)

(8) Preparation of Compound 24

Compound 23 (105 mg, 0.353 mmol) was dissolved in methanol (7 ml), acetic anhydride (333 μl, 3.53 mols) was added to the solution, a catalytic amount of 10% Pd/C was thereafter added to the mixture, and the resulting mixture was stirred at room temperature after replacing the atmosphere in the reactor with hydrogen. TLC indicated disappearance of the material 2 hours later, followed by filtration with activated carbon and concentration. The residue was purified by silica gel column chromatography (ethyl acetate:methanol=5:1), giving Compound 24 (57 mg, yield 72%).

$^1$H-NMR (400 MHz, D$_2$O)

δ 5.23 (dd, 1H, $J_{1,2}$=2.69 Hz, $J_{1,F}$=1.44 Hz, H-1-α), 4.65 (ddd, 1H, $J_{4,F}$=50.94 Hz, $J_{3,4}$=9.06 Hz, $J_{4,5}$=9.58 Hz, H-4-α), 4.47 (m, 1H, H-2-α), 4.43 (ddd, 1H, $J_{3,F}$=14.28 Hz, $J_{2,3}$=4.9 Hz, H-3-α), 4.16 (m, 1H, H-5-α), 3.95 (m, 2H, H-6a-α, H-6b-α), 2.14 (s, 3H, NHCOCH$_3$-α)

$^{13}$C-NMR (400 MHz, D$_2$O)

δ 175.27 (C=O-α), 93.46 (C-1-α), 88.30 (d, $J_{4,F}$=177.00 Hz, C-4-α), 69.91 (d, $J_{5,F}$=24.41 Hz, C-5-α), 67.60 (d, $J_{3,F}$=18.74 Hz, C-3-α), 60.36 (C-6), 54.12 (d, $J_{2,F}$=8.68 Hz, C-2-α), 22.31 (NHCOCH$_3$-α)

Compound 24 ⟶ 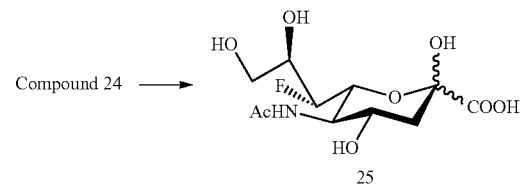

25

(9) Preparation of Compound 25

Compound 24 (50 mg, 0.224 mmol), sodium piruvate (123 mg, 1.12 mmols) and bovine serum albumin (5 mg) were dissolved in a sodium phosphate buffer solution (100 mM, pH 7.5, 3.4 ml), and aldolase sialate was thereafter added to the solution to start a reaction at room temperature. The reaction mixture was freeze-dried 24 hours later. The product was dissolved in a small amount of water and applied to an anion-exchange resin column (AG 1-X8, 200-400 mesh, formate form). After passing 300 ml of water through the column, the desired product was eluted with 1M formic acid, and the eluate was concentrated under the decompression. The resi- Compound 22 ⟶ 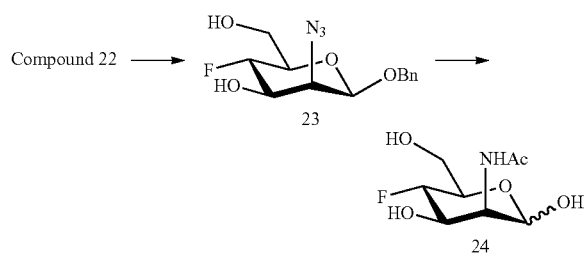

due was purified with a gel filtration column (Sephadex G-15, water), giving Compound 25 (40 mg, yield 58.9%).

$^1$H-NMR (400 MHz, D$_2$O)

δ 4.61 (dd, 1H, $J_{7,8}$=8.97 Hz, $J_{7,F}$=45.56 Hz, H-7), 4.18 (dd, 1H, $J_{5,6}$=10.63 Hz, $J_{6,F}$=29.86 Hz, H-6), 4.15 (m, 1H, H-4), 4.07 (m, 1H, H-8), 4.02 (dd, 1H, $J_{4,5}$=10.10 Hz, H-5), 3.90 (ddd, 1H, $J_{9a9b}$=120.18 Hz, $J_{9a,8}$=2.77 Hz, $J_{9a,F}$=2.86 Hz, H-9a), 3.76 (ddd, 1H, $J_{9b,8}$=5.33 Hz, $J_{9b,F}$=2.06 Hz, H-9b), 2.40 (dd, 1H, $J_{3eq,3ax}$=13.00, $J_{3eq,4}$=4.88 Hz, H-3eq), 2.15 (s, 3H, OCOC$\underline{H}_3$), 2.00 (dd, 1H, $J_{3ax,4}$=11.70 Hz, H-3ax)

$^{13}$C-NMR (400 MHz, D$_2$O)

δ 175.17, 173.68 (C=O), 96.01 (C-1), 89.12 (d, $J_{7,F}$=179.23 Hz, C-7), 69.67 (d, $J_{6,F}$=17.41 Hz, C-6), 68.31 (d, $J_{8,F}$=26.50 Hz, C-8), 67.26 (C-4), 62.70 (C-6), 52.17 (C-5), 39.19 (C-3), 22.61 (NHCOC$\underline{H}_3$)

Reference Example 15

Preparation of 5-Acetamido-3,5,8-trideoxy-8-fluoro-D-glycero-β-D-galacto-2-nonulopyranosidonic acid (8-fluorosialic acid, 27)

5-Acetamido-3,5,8-trideoxy-8-fluoro-D-glycero-β-D-galacto-2-nonulopyranosidonic acid (27) was prepared from Sialic acid (26) according to the scheme given below.

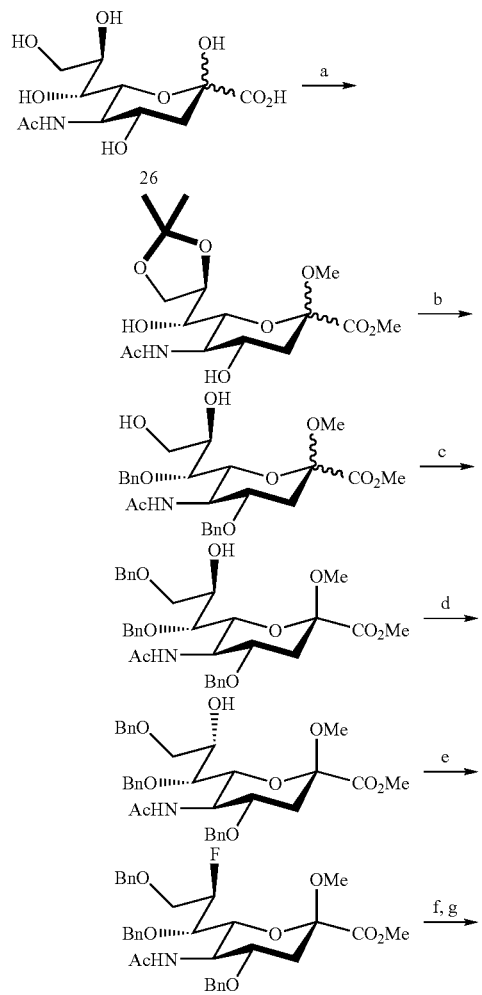

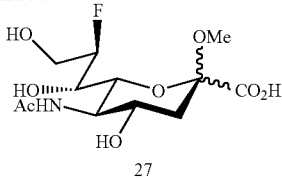

NMR data of 8-fluorosialic acid are shown below.

$^1$H-NMR (400 MHz, D$_2$O),

δ 4.69 (dddd, 1H, $J_{8,F}$=48.7 Hz, $J_{8,9a}$=5.0 Hz, $J_{8,9b}$=3.5 Hz, H-8), 4.03 (ddd, 1H, $J_{4,5}$=10.0 Hz, $J_{3ax,4}$=11.1 Hz, $J_{3eq,4}$=4.7 Hz, H-4), 3.95 (dd, 1H, $J_{4,5}$=10.0 Hz, $J_{5,6}$=9.9 Hz, H-5), 3.94 (ddd, 1H, $J_{6,7}$=~0 Hz, $J_{7,8}$=6.8 Hz, $J_{7,F}$=14.0 Hz, H-7), 3.88 (ddd, 1H, $J_{9a9b}$=13.3 Hz, $J_{9a,8}$=3.5 Hz, $J_{9b,F}$=28.0 Hz, H-9b), 3.86 (dd, 1H, $J_{5,6}$=9.9 Hz, $J_{6,7}$=~0 Hz, H-6), 3.72 (ddd, 1H, $J_{9a,9b}$=5.33 Hz, $J_{9a,8}$=5.0 Hz, $J_{9a,F}$=30.6 Hz, H-9a), 2.28 (dd, 1H, $J_{3eq,3ax}$=13.00, $J_{3eq,4}$=4.6 Hz, H-3eq), 2.05 (s, 3H, Ac), 1.87 (dd, 1H, $J_{3ax,4}$=11.1 Hz, $J_{3eq,3ax}$=13.00, H-3ax)

Reference Example 16

Preparation of 5-Acetamido-3,5,9-trideoxy-9-fluoro-D-glycero-β-D-galacto-2-nonulopyranosidonic acid (9-fluorosialic acid, 28)

5-Acetamido-3,5,9-trideoxy-9-fluoro-D-glycero-β-D-galacto-2-nonulopyranosidonic acid (28) was prepared from sialic acid (26) according to the scheme given below.

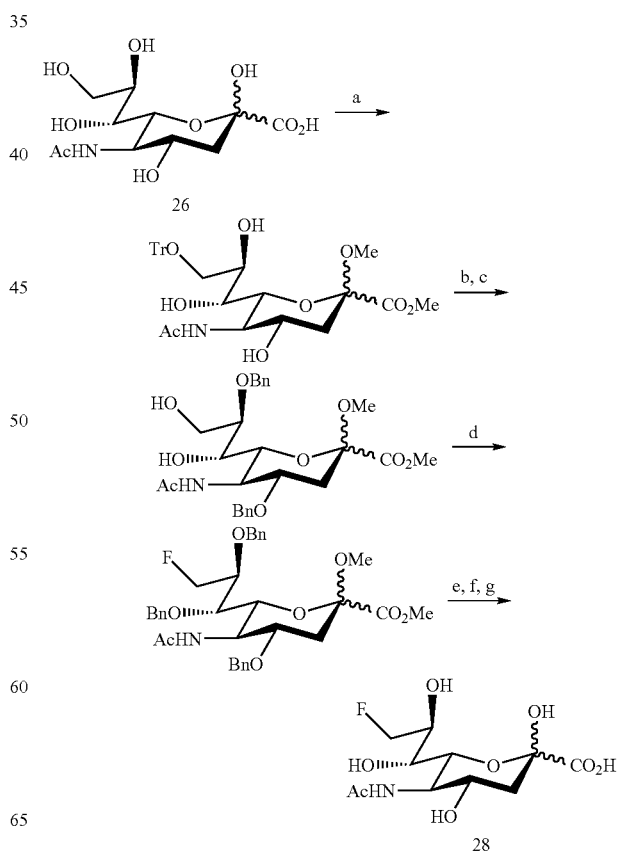

Reference Example 17

Preparation of CMP-sialic acid

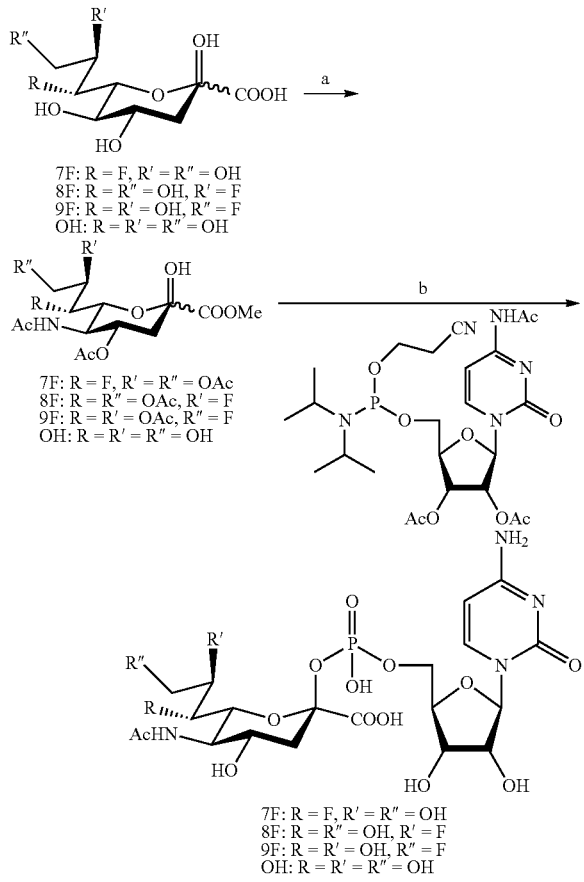

(a) (1) Dowex 50-X8, MeOH, (2) Ac$_2$O, 60% HClO$_4$;
(b) (1) 1H-Tetrazole, CH$_3$CN, (2) t-BuOOH, CH$_3$CN, (3) DBU, CH$_3$CN, (4) NaOMe, MeOH, H$_2$O Sialic acid (0.074 mmoles) was dissolved in distilled methanol (3 ml), Dowex-50W-X8 (65 mg) was added to the solution with stirring at room temperature under an argon stream, and the mixture was reacted for 3 hours. After confirming the completion of reaction, the reaction mixture was filtered and concentrated in a vacuum. The residue was dissolved in acetic anhydride (200 μl), a solution (22 μl) of acetic anhydride and 60% perchloric acid (15:1) was added to the solution with stirring at 120° C., and the mixture was reacted at 10° C. for 40 minutes. After confirming the completion of reaction, the reaction mixture was diluted with ethyl acetate, the dilution was washed with saturated aqueous solution of sodium bicarbonate. The organic layer was dried over anhydrous magnesium sulfate, filtered and then concentrated in a vacuum, affording a residue containing sialic acid (29) having protected carboxyl. The residue and CMP-5'-phosphoamidite derivative (30) (0.23 mmole) were azeotropically boiled with benzene three times, the residue was dissolved in distilled acetonitrile (100 μl) each time, and the resulting solutions were mixed together. To the resulting solution was added 1H-tetrazole (17 mg, 0.23 mmole) with stirring in ice water under an argon stream. The mixture was returned to room temperature 5 minutes later, followed by a further reaction for 10 minutes. After the completion of reaction was recognized, the reaction mixture was diluted with ethyl acetate and washed with a saturated aqueous solution of sodium bicarbonate and saturated aqueous solution of sodium chloride. The organic layer was dried over anhydrous magnesium sulfate, followed by filtration and concentration at a temperature of up to 30° C. and further by azeotropic boiling with toluene twice to remove water. Distilled acetonitrile (400 μl) was added to the residue, and 2.5M t-BuOOH toluene solution (290 μl) was added dropwise to the mixture with ice cooling under an argon stream. The mixture was returned to room temperature 5 minutes later, followed by stirring for 20 minutes. After completion of reaction was recognized, dimethyl sulfide (53 μl) was added dropwise to the mixture, and the t-BuOOH was quenched. DBU (18 μl) was thereafter added dropwise to the mixture, followed by stirring at room temperature for 20 minutes. After the completion of reaction was recognized, methanol (0.67 ml), water (1.35 ml) and sodium methoxide (360 mg) were added to the reaction mixture, followed by reaction at room temperature for 16 hours. After the completion of reaction was recognized, the reaction mixture was subjected to extraction with water, and the extract was washed with dichloromethane. The aqueous layer was concentrated in a vacuum to about 8 ml at a temperature of up to 25° C. The resulting aqueous solution was purified by gel column chromatography (eluent: 20 mM ammonia water, flow rate: 0.3 ml/min), giving CMP-sialic acid.

Reference Example 18

Preparation of CMP-7"-deoxy-7"-fluoro-sialic acid

CMP-7"-deoxy-7"-fluoro-sialic acid was prepared in the same manner as in Reference Example 7 with the exception of using Compound (25) in place of sialic acid. NMR data is given below.

$^1$H-NMR (400 MHz, 50 mM ND$_4$DCO$_3$ in D$_2$O),
δ8.04 (d, 1H, J$_{5,6}$=7.6 Hz, H-6), 6.20 (d, 1H, J$_{6,5}$=7.6 Hz, H-5), 6.06 (d, 1H, J$_{1',2'}$=4.5 Hz, H-1'), 4.54 (dd, 1H, J$_{7'',8''}$=9.5 Hz, J$_{7'',F}$=45.9 Hz, H-7"), 4.42~4.20 (m, 7H, H-2', H-3', H-4', H-5'a, H-5'b, H-6", H-8"), 4.16 (ddd, 1H, J$_{4'',3''eq}$=4.7 Hz, J$_{4'',3''ax}$=11.3 Hz, J$_{4,5}$=10.3 Hz, H-4"), 4.03 (dd, 1H, J$_{5'',4''}$=J$_{5'',6''}$=10.3 Hz, H-5"), 3.91 (ddd, 1H, J$_{9''a,9''b}$=12.2 Hz, J$_{9''a,8''}$=2.8 Hz, J$_{9''a,F}$=2.8 Hz, H-9"a), 3.75 (ddd, 1H, J$_{9''a,9''b}$=12.2 Hz, J$_{9''b,8''}$=5.4 Hz, J$_{9''b,F}$=2.1 Hz, H-9"b), 2.61 (dd, 1H, J$_{3''eq,4''}$=4.7 Hz, J$_{gem}$=13.3 Hz, H-3"eq), 2.14 (s, 3H, Ac), 1.76 (ddd, 1H, J$_{3''ax,4''}$=11.5 Hz, J$_{gem}$=13.3 Hz, J$_{3''ax,F}$=5.6 Hz, H-3"ax),

Reference Example 19

Preparation of CMP-8"-deoxy-8"-fluoro-sialic acid

CMP-8"-deoxy-8"-fluoro-sialic acid was prepared in the same manner as in Reference Example 7 with the exception of using Compound (27) in place of sialic acid. NMR data is given below.

$^1$H-NMR (400 MHz, 50 mM ND$_4$DCO$_3$ in D$_2$O),
δ 8.08 (d, 1H, J$_{5,6}$=7.6 Hz, H-6), 6.20 (d, 1H, J$_{6,5}$=7.6 Hz, H-5), 6.09 (d, 1H, J$_{1',2'}$=4.1 Hz, H-1'), 4.90 (m, 1H, H-8"), 4.42 (dd, 1H, J$_{3',2'}$=J$_{3',4'}$=4.9 Hz, H-3'), 4.39 (dd, 1H, J$_{2',1'}$=4.1 Hz, J$_{2',3'}$=4.9 Hz, H-2'), 4.31-4.28 (m, 3H, H-4', H-5'a, H-5'b), 4.15 (ddd, 1H, J$_{4'',3''eq}$=4.4 Hz, J$_{4'',3''ax}$=11.5 Hz, J$_{4,5}$=10.5 Hz, H-4"), 4.10-3.90 (m, 5H, H-5", H-6", H-7", H-9"a, H-9"b), 2.60 (dd, 1H, J$_{3''eq,4''}$=4.4 Hz, J$_{gem}$=13.1 Hz, H-3"eq), 2.13 (s, 3H, Ac), 1.77 (ddd, 1H, J$_{3''ax,4''}$=11.5 Hz, J$_{gem}$=13.1 Hz, J$_{3''ax,F}$=4.5 Hz, H-3"ax),

Reference Example 20

Preparation of CMP-9"-deoxy-9"-fluoro-sialic acid

CMP-9"-deoxy-9"-fluoro-sialic acid was prepared in the same manner as in Reference Example 7 with the exception of using Compound (28) in place of sialic acid.

Example 1

Preparation of Asparagine-Linked disialo α2,3-oligosaccharide (C1-1) Wherein the Amino Group of the Asparagine is Protected with Fmoc Group and Two Kinds of Asparagine-Linked monosilo α2,3-oligosaccharides (C1-2 and C1-3) Wherein the Amino Group of the Asparagine is Protected with Fmoc Group Using sialic acid transferase, CMP-sialic acid was transferred to the asparagine-linked asialooligosaccharide which was obtained in Reference Example 3 and wherein the amino group of the asparagine was protected with Fmoc group.

The sialic acid transferase used was α2,3-transferase which was commercially available and derived from a rat recombinant.

The asialononasaccharide (20 mg, 10.1 μmoles) obtained in Reference Example 3 was dissolved in 50 mM of cacodylic acid buffer (6.0 in pH, 5 ml), and bovine serum albumin (BSA, 5 mg) was then added to the solution. To the mixture were added CMP-sialic acid (26 mg, 40.4 μmoles) and alkanline phosphatase (5 μl, 125 units), and the resulting mixture was stirred uniformly. Finally, α2,3-sialyltransferase (product of CALBIOCHEM, 100 μl) was added to the mixture, and the resulting mixture was allowed to stand at 37° C. for 48 hours. The reaction was terminated upon the starting material reducing to the desired quantity while monitoring the reaction by HPLC, and the reaction mixture was filtered with a membrane filter. The filtrate was concentrated to reduce the quantity thereof and thereafter purified by HPLC (YMC-Pack R&D ODS, D-ODS-5-A, 20×250 mm, AN/25 mM AcONH$_4$ buffer=18/82, 7.5 ml/min., wave length: 274 nm). The eluates obtained were disialoundecasaccharide compound (C1-1) in 25 minutes, and monosialodecasaccharide compounds (C1-2) and (C1-3) in 30 minutes and 34 minutes, respectively. The fractions were collected, desalted and freeze-dried individually, giving Compounds 1, 2 and 3 in respective amounts of 0.7 mg (2.7%), 1.9 mg (8.3%) and 3.5 mg (15.3%). The NMR data as to the compounds is given below.

Compound (C1-1)

$^1$H NMR (400 MHz, D$_2$O, 30° C., HOD=4.81)

δ 7.90 (d, 2H, Fmoc), 7.69 (d, 2H, Fmoc), 7.49 (dd, 2H, Fmoc), 7.42 (dd, 2H, Fmoc), 5.10 (s, 1H, Man4-H1), 4.97 (d, 1H, GlcNAc1-H1), 4.91 (s, 1H, Man4'-H-1), 4.50-4.60 (m, 4H), 4.34 (1H, Fmoc), 4.24 (bs, 1H, Man3-H2), 4.18 (bs, 1H, Man4-H2), 4.10 (m, 2H), 2.74 (m, 3H, Asn-βCH, NeuAc7, 7'-H3eq), 2.40-2.60 (m, 1H, Asn-βCH), 2.05, 2.03, 2.02 (each s, Ac), 1.77 (dd, 2H, NeuAc7,7'-H3ax).

Compound (C1-2)

$^1$H NMR (400 MHz, D$_2$O, 30° C., HOD=4.81)

δ 7.90 (d, 2H, Fmoc), 7.69 (d, 2H, Fmoc), 7.49 (dd, 2H, Fmoc), 7.42 (dd, 2H, Fmoc), 5.10 (s, 1H, Man4-H1), 4.97 (d, 1H, GlcNAc1-H1), 4.90 (s, 1H, Man4'-H-1), 4.47-4.60 (m), 4.43 (d, 1H), 4.32 (1H, Fmoc), 4.22 (bs, 2H), 4.17 (bs, 1H, Man4-H2), 4.06-4.13 (m, 2H), 2.72 (m, 2H, Asn-βCH, NeuAc7-H3eq), 2.50-2.60 (m, 1H, Asn-βCH), 2.05, 2.03, 2.01 (each s, Ac), 1.77 (dd, 1H, NeuAc7-H3ax).

Compound (C1-3)

$^1$H NMR (400 MHz, D$_2$O, 30° C., HOD=4.81)

δ 7.90 (d, 2H, Fmoc), 7.69 (d, 2H, Fmoc), 7.49 (dd, 2H, Fmoc), 7.42 (dd, 2H, Fmoc), 5.10 (s, 1H, Man4-H1), 4.97 (d, 1H, GlcNAc1-H1), 4.90 (s, 1H, Man4'-H-1), 4.50-4.60 (m), 4.45 (d, 1H), 4.33 (1H, Fmoc), 4.22 (m, 2H), 4.17 (bs, 1H, Man4-H2), 4.09 (m, 2H), 2.74 (m, 2H, Asn-βCH, NeuAc7-H3eq), 2.45-2.60 (m, 1H, Asn-βCH), 2.05, 2.03, 2.02, 2.00 (each s, Ac), 1.77 (dd, 1H, NeuAc7-H3ax)

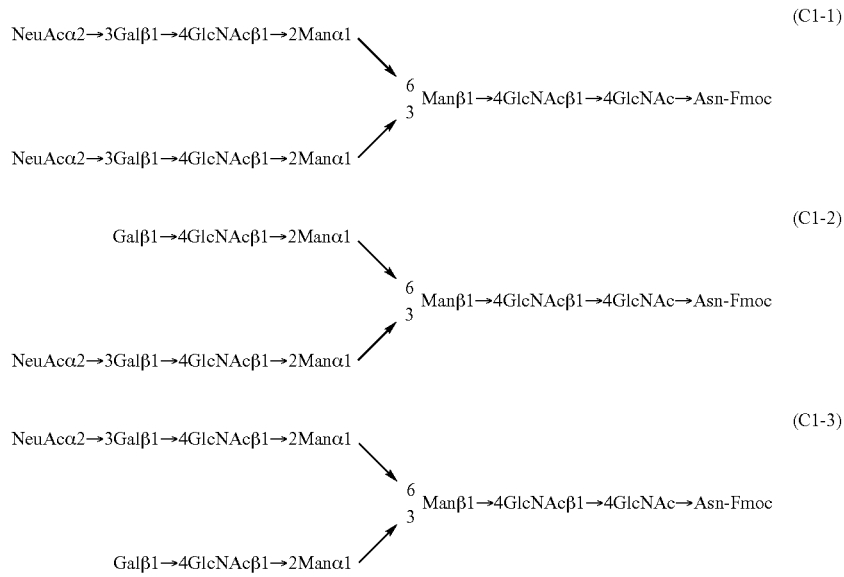

Example 2

Compound (C1-2) (2 mg, 0.88 μmole) obtained in Example 1 and 1 mg of bovine serum albumin were dissolved in 100 μl of HEPES buffer solution (50 mM, pH 5.0), and β-galactosidase (product of Seikagaku Corp., from Jack Beans, 5 μl, 100 mU) was added to the solution. The resulting solution was allowed to stand at 37° C. for 15 hours, and thereafter filtered with a membrane filter. The filtrate was purified by HPLC [ODS column, 2.0 (diam.)×25 cm; eluent: 50 mM aqueous solution of ammonium acetate:acetonitrile=82:18; flow rate 7.5 ml/min], followed by concentration of the solvent and freeze-drying. The residue was dissolved in 200 μl of water and desalted by ODS-column chromatography (Cosmosil 75$C_{18}$-opn, washing with water first, subsequent elution with 25% aqueous solution of acetonitrile), giving 0.5 μg of the desired Compound (C2). The NMR data is given below.

$^1$H NMR (400 MHz, $D_2O$, 30° C., HOD=4.81)

δ 7.90 (d, 2H, Fmoc), 7.69 (d, 2H, Fmoc), 7.49 (dd, 2H, Fmoc), 7.42 (dd, 2H, Fmoc), 5.10 (s, 1H, Man4-H1), 4.98 (d, 1H, GlcNAc1-H1), 4.90 (s, 1H, Man4'-H-1), 4.50-4.60 (m), 4.33 (1H, Fmoc), 4.22 (m, 2H), 4.17 (bs, 1H, Man4-H2), 4.10 (m, 2H), 2.74 (m, 2H, Asn-βCH, NeuAc7-H3eq), 2.45-2.60 (m, 1H, Asn-βCH), 2.05, 2.03, 2.01 (each s, Ac), 1.78 (dd, 1H, NeuAc7-H3ax)

(C2)

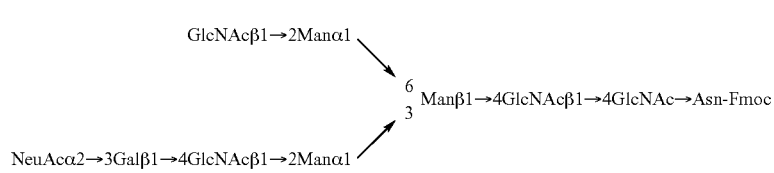

Example 3

Compound (C2) (1.8 mg, 0.86 μmole) obtained in Example 2 and 1 mg of bovine serum albumin were dissolved in 90 μl of HEPES buffer solution (50 mM, pH 5.0), and 4 μl (250 mU) of N-acetyl-β-glucosamidase (product of Sigma-Aldrich Corp., from Jack Beans) was added to the solution. The resulting solution was allowed to stand at 37° C. for 24 hours, and thereafter filtered with a membrane filter. The filtrate was purified by HPLC [ODS column, 2.0 (diam.)×25 cm; eluent: 50 mM aqueous solution of ammonium acetate:acetonitrile=82:18; flow rate 7.5 ml/min], followed by concentration of the solvent and freeze-drying. The residue was dissolved in 200 μl of water and desalted by ODS-column chromatography (Cosmosil 75$C_{18}$-opn, washing with water first, subsequent elution with 25% aqueous solution of acetonitrile), giving 0.9 μg of the desired Compound (C3).

$^1$H NMR (400 MHz, $D_2O$, 30° C., HOD=4.81)

δ 8.01 (d, 2H, J=7.6, Fmoc), 7.80 (d, 2H, J=7.6, Fmoc), 7.60 (dd, 2H, J=7.6, Fmoc), 7.53 (dd, 2H, J=7.6, Fmoc), 5.21 (s, 1H, Man4-H1), 5.09 (d, 1H, J=8.8, GlcNAc1-H1), 5.00 (s, 1H, Man4'-H-1), 4.87 (s, 1H), 4.60-4.78 (m, 5H), 4.40-4.50 (bm, 2H), 4.34 (s, 1H), 4.28 (bs, 1H, Man4-H2), 4.20 (dd, 1H, Ja=3.0, Jb=9.9), 2.80-2.95 (m, 2H, Asn-βCH, NeuAc7-H3eq), 2.65-2.75 (m, 1H, Asn-βCH), 2.16, 2.14, 2.12 (eachs, Ac×3), 1.98 (s, 3H, Ac), 1.89 (dd, 1H, Ja=12.1, Jb=11.9, NeuAc7-H3ax).

(C3)

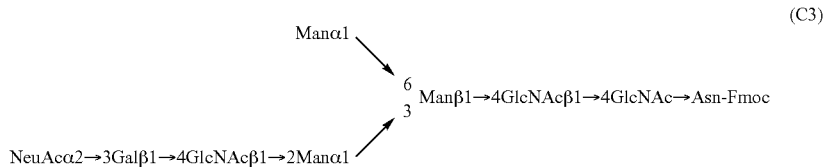

Example 4

Compound (C3) (0.8 mg, 0.42 μmole) obtained in Example 3 and 1 mg of bovine serum albumin were dissolved in 50 μl of HEPES buffer solution (50 mM, pH 5.0), and 30 μl (2.9 U) of α-mannosidase (product of Sigma-Aldrich Corp., from Jack Beans) was added to the solution. The resulting solution was allowed to stand at 37° C. for 63 hours, and thereafter filtered with a membrane filter. The filtrate was purified by HPLC [ODS column, 2.0 (diam.)×25 cm; eluent: 50 mM aqueous solution of ammonium acetate:acetonitrile=80:20; flow rate 7.5 ml/min], followed by concentration of the solvent and freeze-drying. The residue was dissolved in 200 μl of water and desalted by ODS-column chromatography (Cosmosil 75$C_{18}$-opn, washing with water first, subsequent elution with 25% aqueous solution of acetonitrile), giving 0.6 μg of the desired Compound (C4).

$^1$H NMR (400 MHz, $D_2O$, 30° C., HOD=4.81)

δ 8.00 (d, 2H, J=7.2, Fmoc), 7.79 (d, 2H, J=7.2, Fmoc), 7.59 (dd, 2H, J=7.2, Fmoc), 7.52 (dd, 2H, J=7.2, Fmoc), 5.21 (s, 1H, Man4-H1), 5.09 (d, 1H, J=10.0, GlcNAc1-H1), 4.60-4.75 (m), 4.40-4.50 (m, 2H), 4.32 (bd, 1H, J=2.3), 4.28 (bs, 1H), 4.22 (bdd, 1H, Ja=9.7, Jb=2.8, Man4-H2), 2.80-2.95 (m, 2H, Asn-βCH, NeuAc7-H3eq), 2.60-2.75 (m, 1H, Asn-βCH), 2.14, 2.14, 2.12 (eachs, Ac×3), 1.98 (s, 3H, Ac), 1.88 (dd, 1H, Ja=12.1, Jb=12.0, NeuAc7-H3ax).

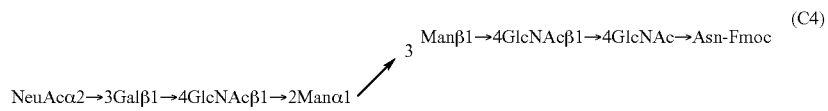

(C4)

Example 5

Compound (C1-3) (1 mg, 0.44 μmole) obtained in Example 1 and 1 mg of bovine serum albumin were dissolved in 50 μl of HEPES buffer solution (50 mM, pH 5.0), and β-galactosidase (product of Seikagaku Corp., from Jack Beans, 5 μl, 100 mU) was added to the solution. The resulting solution was allowed to stand at 37° C. for 15 hours, and thereafter filtered with a membrane filter. The filtrate was purified by HPLC [ODS column, 2.0 (diam.)×25 cm; eluent: 50 mM aqueous solution of ammonium acetate:acetonitrile=82:18; flow rate 7.5 ml/min], followed by concentration of the solvent and freeze-drying. The residue was dissolved in 200 μl of water and desalted by ODS-column chromatography (Cosmosil 75C$_{18}$-opn, washing with water first, subsequent elution with 25% aqueous solution of acetonitrile), giving 0.3 μg of the desired Compound (C5).

$^1$H NMR (400 MHz, D$_2$O, 30%, HOD=4.81)

δ 8.01 (d, 2H, J=7.2, Fmoc), 7.81 (d, 2H, J=7.2, Fmoc), 7.60 (dd, 2H, J=7.2, Fmoc), 7.53 (dd, 2H, J=7.2, Fmoc), 5.21 (s, 1H, Man4-H1), 5.09 (d, 1H, J=9.6, GlcNAc1-H1), 5.02 (s, 1H, Man4'-H-1), 4.55-4.70 (m), 4.44 (1H, Fmoc), 4.30-4.38 (bm, 2H), 4.28 (bd, 1H, Man4-H2), 4.17-4.25 (m, 2H), 2.78-2.95 (m, 2H, Asn-βCH, NeuAc7-H3eq), 2.55-2.70 (m, 1H, Asn-βCH), 2.16, 2.15, 2.14, 2.12 (eachs, 12H, Ac×4), 1.98 (s, 3H, Ac), 1.89 (dd, 1H, Ja=12.2, Jb=12.0, NeuAc7-H3ax).

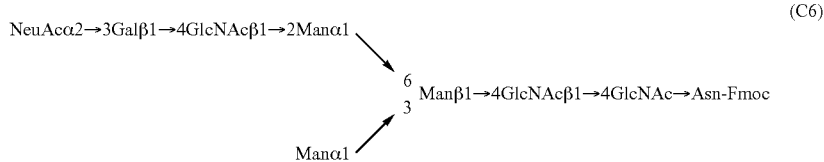

(C5)

Example 6

Compound (C5) (1.0 mg, 0.48 μmole) obtained in Example 5 and 1 mg of bovine serum albumin were dissolved in 50 μl of HEPES buffer solution (50 mM, pH 5.0), and 4 μl (250 mU) of N-acetyl-β-glucosamidase (product of Sigma-Aldrich Corp., from Jack Beans) was added to the solution. The resulting solution was allowed to stand at 37° C. for 22 hours, and thereafter filtered with a membrane filter. The filtrate was purified by HPLC [ODS column, 2.0 (diam.)×25 cm; eluent: 50 mM aqueous solution of ammonium acetate:acetonitrile=82:18; flow rate 7.5 ml/min], followed by concentration of the solvent and freeze-drying. The residue was dissolved in 200 μl of water and desalted by ODS-column chromatography (Cosmosil 75C$_{18}$-opn, washing with water first, subsequent elution with 25% aqueous solution of acetonitrile), giving 0.6 μg of the desired Compound (C6).

$^1$H NMR (400 MHz, D$_2$O, 30%, HOD=4.81)

δ 8.01 (d, 2H, J=7.6, Fmoc), 7.80 (d, 2H, J=7.6, Fmoc), 7.60 (dd, 2H, J=7.6, Fmoc), 7.53 (dd, 2H, J=7.6, Fmoc), 5.19 (s, 1H, Man4-H1), 5.09 (d, 1H, J=9.2, GlcNAc1-H1), 5.02 (s, 1H, Man4'-H-1), 4.85 (s, 1H), 4.58-4.75 (m, 5H), 4.38-4.48 (m, 2H, Fmoc), 4.40 (bd, J=2.4, 1H), 4.18-4.25 (m, 2H), 4.15 (m, 1H), 2.80-2.95 (m, 2H, Asn-βCH, NeuAc7-H3eq), 2.65-2.75 (m, 1H, Asn-βCH), 2.16, 2.13, 2.12 (eachs, 9H, Ac×3), 1.98 (s, 3H, Ac), 1.89 (dd, 1H, Ja=12.2, Jb=12.0, NeuAc7-H3ax).

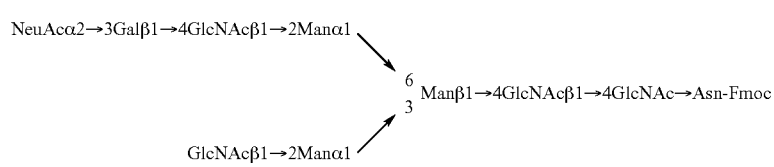

(C6)

Example 7

Compound (C6) (1.0 mg, 0.53 μmole) obtained in Example 6 and 1 mg of bovine serum albumin were dissolved in 50 μl of HEPES buffer solution (50 mM, pH 5.0), and 10 μl (0.9 U) of α-mannosidase (product of Sigma-Aldrich Corp., from Jack Beans) was added to the solution. The resulting solution was allowed to stand at 37° C. for 20 hours, and thereafter filtered with a membrane filter. The filtrate was purified by HPLC [ODS column, 2.0 (diam.)×25 cm; eluent: 50 mM aqueous solution of ammonium acetate:acetonitrile=80:20; flow rate 7.5 ml/min], followed by concentration of the solvent and freeze-drying. The residue was dissolved in 200 μl of water and desalted by ODS-column chromatography (Cosmosil 75C$_{18}$-opn, washing with water first, subsequent elution with 25% aqueous solution of acetonitrile), giving 0.5 μg of the desired Compound (C7).

$^1$H NMR (400 MHz, D$_2$O, 30° C., HOD=4.81)

δ 8.01 (d, 2H, J=7.6, Fmoc), 7.81 (d, 2H, J=7.6, Fmoc), 7.60 (dd, 2H, J=7.2, Fmoc), 7.53 (dd, 2H, J=7.6, Fmoc), 5.09 (d, 1H, J=9.2, GlcNAc1-H1), 5.01 (s, 1H, Man4'-H-1), 4.84 (s, 1H), 4.55-4.70 (m, 5H), 4.44 (t, 1H, J=6.0, Fmoc), 4.30-4.38 (bs, 1H), 4.15-4.25 (m, 2H), 4.17 (s, 1H), 2.80-2.95 (m, 2H, Asn-βCH, NeuAc7-H3eq), 2.55-2.70 (m, 1H, Asn-βCH), 2.16, 2.13, 2.12 (eachs, Ac×3), 1.98 (s, 3H, Ac) 1.89 (dd, 1H, Ja=12.2, Jb=12.3, NeuAc7-H3ax).

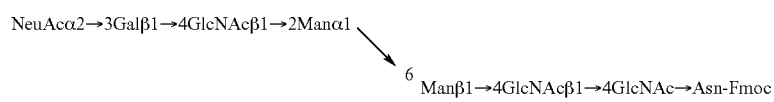

(C7)

Example 7A

Preparation of Asparagine-Linked disialo(α2,6)(α2,3)oligosaccharide Wherein the Amino Group of the Asparagine was Protected with Fmoc Group Using sialic acid transferase, CMP-sialic acid was transferred to the asparagine-linked asialooligosaccharide (Compound 2) which was obtained in Reference Example 3 and wherein the amino group of the asparagine was protected with Fmoc group.

The sialic acid transferase used was α2,3-transferase which was commercially available and derived from a rat recombinant.

Compound 2 (1.7 mg, 0.75 µl mole) obtained in Reference Example 3 was dissolved in 50 mM of cacodylic acid buffer (5.0 in pH, 85 µl), and bovine serum albumin (BSA, 1 mg) was then added to the solution. To the mixture were added CMP-sialic acid (4.8 mg, 7.5 µmoles) and alkanline phosphatase (1 µl, 75 units), and the resulting mixture was stirred uniformly. Finally, α2,3-sialyltransferase (product of CALBIOCHEM, 75 µl, 34 mU) was added to the mixture, and the resulting mixture was allowed to stand at 37° C. for 3.5 hours. The reaction was terminated upon the disappearance of the starting material while monitoring the reaction by HPLC, and the reaction mixture was filtered with a membrane filter. The filtrate was concentrated to reduce the quantity thereof and thereafter purified by HPLC fractionating column (YMC-Pack R&D ODS, D-ODS-5-A, 20×250 mm, AN/25 mM AcONH$_4$ buffer=18/82, 7.5 ml/min., wave length: 274 nm). Compound (C7A) was obtained as an eluate 25 minutes later. The fraction was collected, desalted and freeze-dried, giving 1.3 mg (67.8%) of Compound (C7A). The NMR data is given below.

$^1$H NMR (400 MHz, D$_2$O, 30° C., HOD=4.81)

δ 8.00 (d, 2H, J=7.2, Fmoc), 7.79 (d, 2H, J=7.2, Fmoc), 7.60 (dd, 2H, J=7.2, Fmoc), 7.52 (dd, 2H, J=7.2, Fmoc), 5.21 (s, 1H, Man4-H1), 5.09 (d, 1H, J=8.8, GlcNAc1-H1), 5.03 (s, 1H, Man4'-H-1), 4.86 (s, 1H), 4.58-4.72 (m, 5H), 4.54 (d, 1H, J=8.0), 4.38-4.48 (m, 2H), 4.34 (bs, 1H), 4.28 (bs, 1H), 4.15-4.25 (m, 2H), 2.80-2.86 (dd, 1H, Ja=4.4, Jb=12.4, NeuAc7-H3eq), 2.73-2.83 (m, dd, 3H, Ja=4.4, Jb=12.4, Asn-βCH, NeuAc7-H3eq), 2.60-2.72 (m, 1H, Asn-βCH), 2.16, 2.15, 2.14, 2.12 (each s, Ac×5), 1.98 (s, 3H, Ac), 1.89 (dd, 1H, Ja=12.4, Jb=12.0, NeuAc7-H3ax), 1.81 (dd, 1H, Ja=12.4, Jb=12.0, NeuAc7-H3ax).

Example 7B

Preparation of Asparagine-Linked disialo (α2,3)(α2,6)oligosaccharide Wherein the Amino Group of the Asparagine was Protected with Fmoc Group Using sialic acid transferase, CMP-sialic acid was transferred to the asparagine-linked asialooligosaccharide (Compound 3) which was obtained in Reference Example 3 and wherein the amino group of the asparagine was protected with Fmoc group.

The sialic acid transferase used was α2,3-transferase which was commercially available and derived from a rat recombinant.

Compound 3 (1.2 mg, 0.53 µmole) obtained in Reference Example 3 was dissolved in 50 mM of cacodylic acid buffer (5.0 in pH, 60 µl), and bovine serum albumin (BSA, 1 mg) was then added to the solution. To the mixture were added CMP-sialic acid (3.4 mg, 5.3 µmoles) and alkanline phosphatase (1 µl, 75 units), and the resulting mixture was stirred uniformly. Finally, α2,3-sialyltransferase (product of CALBIOCHEM, 52.9 µl, 24 mU) was added to the mixture, and the resulting mixture was allowed to stand at 37° C. for 3 hours. The reaction was terminated upon the disappearance of the starting material while monitoring the reaction by HPLC, and the reaction mixture was filtered with a membrane filter. The filtrate was concentrated to reduce the quantity thereof and thereafter purified by HPLC fractionating column (YMC-Pack R&D ODS, D-ODS-5-A, 20×250 mm, AN/25 mM AcONH$_4$ buffer=18/82, 7.5 ml/min., wave length: 274 nm). Compound (C7B) was obtained as an eluate 23 minutes later. The fraction was collected, desalted and freeze-dried, giving 1.1 mg (81.2%) of Compound (C7B). The NMR data is given below.

$^1$H NMR (400 MHz, D$_2$O, 30° C., HOD=4.81)

δ 8.00 (d, 2H, J=7.6, Fmoc), 7.79 (d, 2H, J=7.6, Fmoc), 7.59 (dd, 2H, J=7.6, Fmoc), 7.51 (dd, 2H, J=7.6, Fmoc), 5.21 (s, 1H, Man4-H1), 5.08 (d, 1H, J=10.0, GlcNAc1-H1), 5.00 (s, 1H, Man4'-H-1), 4.84 (s, 1H), 4.60-4.72 (m, 5H), 4.52 (d, 1H, J=7.6), 4.35-4.45 (m, 2H), 4.33 (bs, 1H), 4.27 (bs, 1H), 4.15-4.25 (m, 2H), 2.80-2.86 (dd, 1H, Ja=4.8, Jb=12.4, NeuAc7-H3eq), 2.73-2.83 (bs, dd, 3H, Ja=4.8, Jb=12.4, Asn-βCH, NeuAc7-H3eq), 2.60-2.72 (m, 1H, Asn-βCH), 2.15, 2.12, 2.10 (each s, Ac×5), 1.97 (s, 3H, Ac), 1.88 (dd, 1H, Ja=12.4, Jb=12.4, NeuAc7-H3ax), 1.80 (dd, 1H, Ja=12.4, Jb=12.4, NeuAc7-H3ax).

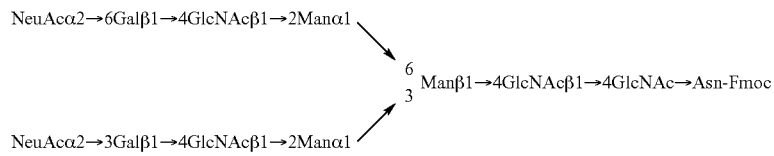

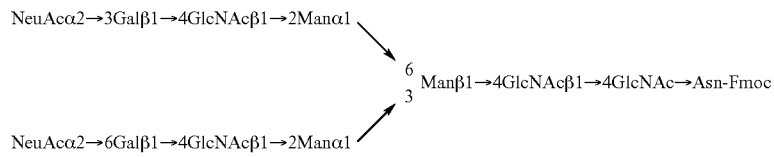

Example 8

Preparation of Asparagine-Linked di7"-deoxy-7"-fluoro-sialo($\alpha$2,3)oligosaccharide Wherein the Amino Group of the Asparagine was Protected with Fmoc Group (C8-1), and Two Kinds of Asparagine-Linked mono7"-deoxy-7"-fluoro-sialo($\alpha$2,3)oligosaccharide Wherein the Amino Group of the Asparagine was Protected with Fmoc Group (C8-2 and C8-3)

Asparagine-linked di7"-deoxy-7"-fluoro-sialo($\alpha$2,3)oligosaccharide wherein the amino group of the asparagine was protected with Fmoc group, and two kinds of asparagine-linked mono7"-deoxy-7"-fluoro-sialo($\alpha$2,3)oligosaccharide wherein the amino group of the asparagine was protected with Fmoc group shown below were obtained in the same manner as in Example 1 except of using CMP-7"-deoxy-7"-fluoro-sialic acid obtained in Reference Example 8

(C8-1)

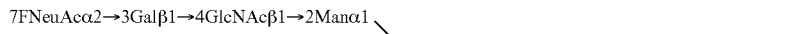

(C8-2)

(C8-3)

Example 9

Compound (C9) was obtained in the same manner as in Example 2 except of using Compound (C8-2) obtained in Example 8 in place of Compound (C1-2) in Example 2.

(C9)

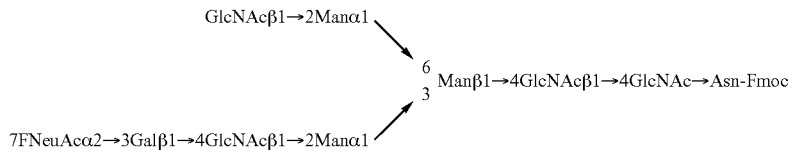

Example 10

Compound (C10) was obtained in the same manner as in Example 3 except of using Compound (C9) obtained in Example 9 in place of Compound (C2) in Example 3.

(C10)

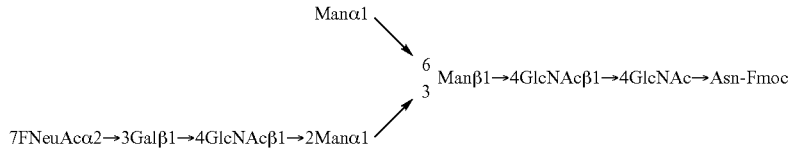

Example 11

Compound (C11) was obtained in the same manner as in Example 4 except of using Compound (C10) obtained in Example 10 in place of Compound (C3) in Example 4.

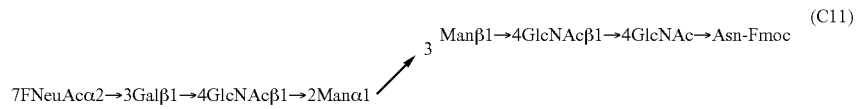
(C11)

Example 12

Compound (C12) was obtained in the same manner as in Example 5 except of using Compound (C8-3) obtained in Example 8 in place of Compound (C1-3) in Example 5.

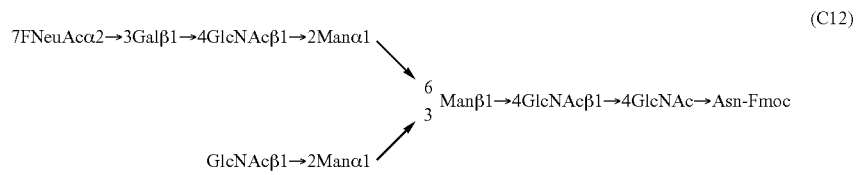
(C12)

Example 13

Compound (C13) was obtained in the same manner as in Example 6 except of using Compound (C12) obtained in Example 12 in place of Compound (C5) in Example 6.

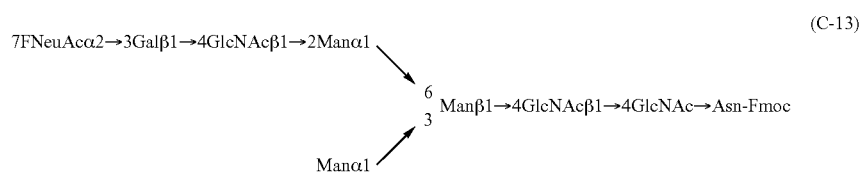
(C-13)

Example 14

Compound (C14) was obtained in the same manner as in Example 7 except of using Compound (C13) obtained in Example 13 in place of Compound (C6) in Example 7.

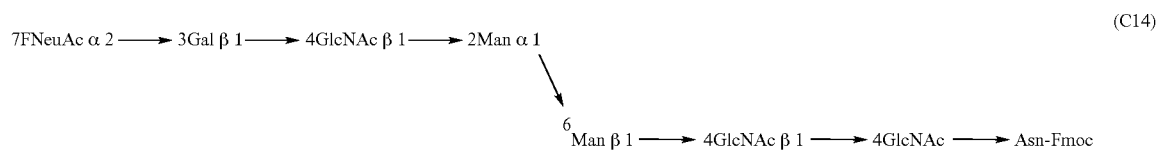
(C14)

Example 15

Preparation of Asparagine-Linked di8"-deoxy-8"-fluoro-sialo(α2,3)oligosaccharide Wherein the Amino Group of the Asparagine was Protected with Fmoc Group (C15-1), and Two Kinds of Asparagine-Linked mono8"-deoxy-8"-fluoro-sialo(α2,3)oligosaccharide Wherein the Amino Group of the Asparagine was Protected with Fmoc Group (C15-2 and C15-3)

Asparagine-linked di8"-deoxy-8"-fluoro-sialo(α2,3)oligosaccharide wherein the amino group of the asparagine was protected with Fmoc group, and two kinds of asparagine-linked mono8"-deoxy-8"-fluoro-sialo(α2,3)oligosaccharide wherein the amino group of the asparagine was protected with Fmoc group shown below were obtained in the same manner as in Example 1 except of using CMP-8"-deoxy-8"-fluoro-sialic acid obtained in Reference Example 9.

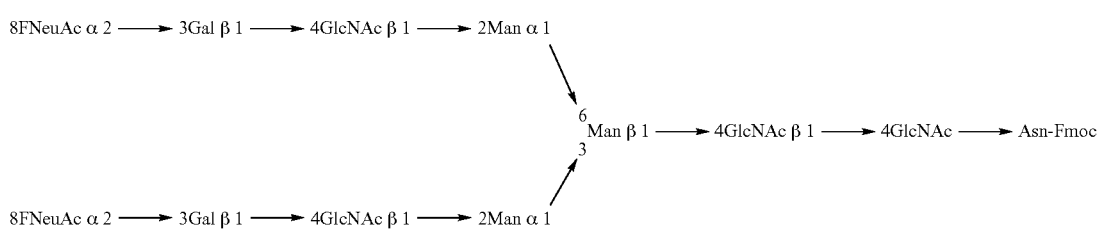
(C15-1)

The above asparagine-linked oligosaccharide corresponds to Compound (1) wherein $R^1=R^2$=formula (2), R=OH, R'=F and R"=OH.

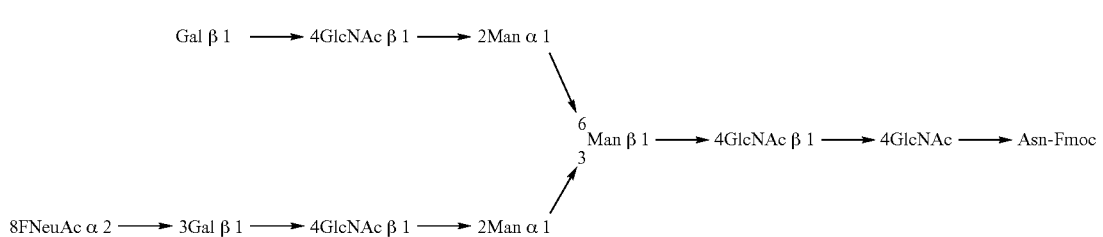
(C15-2)

The above asparagine-linked oligosaccharide corresponds to Compound (1) wherein $R^1$=formula (3), $R^2$=formula (2), R=OH, R'=F and R"=OH.

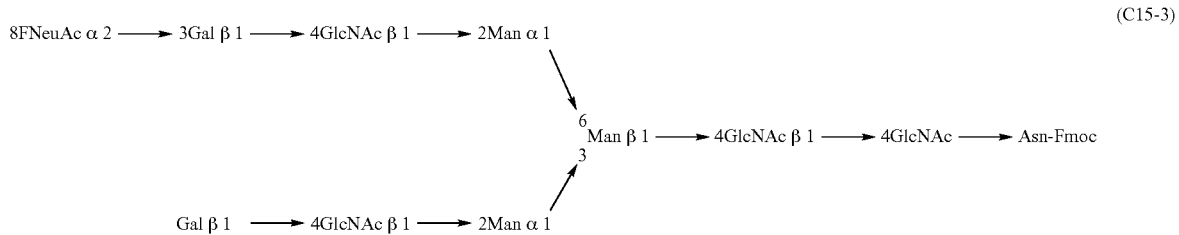
(C15-3)

The above asparagine-linked oligosaccharide corresponds to Compound (1) wherein $R^1$=formula (2), R=OH, R'=F, R"=OH and $R^2$=formula (3).

Example 16

Hydrolysis of Compound of Example 15 Using Galactosidase

Compound (C16) was obtained in the same manner as in Example 2 except of using Compound (C15-2) obtained in Example 15 in place of Compound (C1-2) in Example 2.

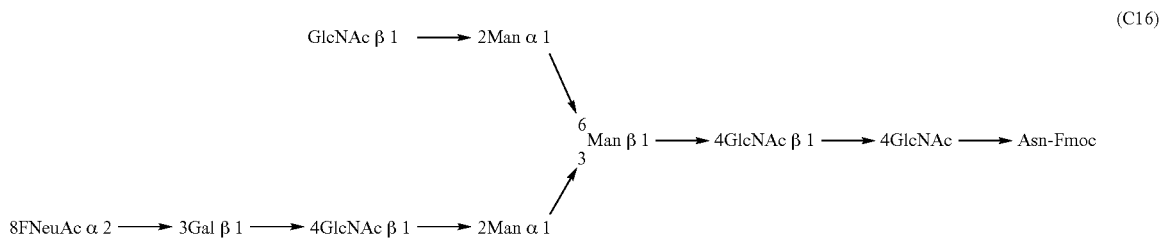
(C16)

The above asparagine-linked oligosaccharide corresponds to Compound (1) wherein R$^1$=formula (4), R$^2$=formula (2), R=OH, R'=F and R"=OH.

Example 17

Hydrolysis of Compound of Example 16 Using N-Acetylglucosaminidase

Compound (C17) was obtained in the same manner as in Example 3 except of using Compound (C16) obtained in Example 16 in place of Compound (C2) in Example 3.

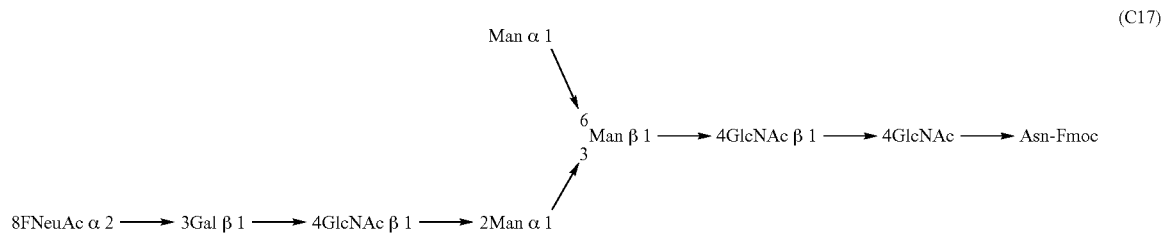

(C17)

The above asparagine-linked oligosaccharide corresponds to Compound (1) wherein R$^1$=formula (5), R$^2$=formula (2), R=OH, R'=F and R"=OH.

Example 18

Hydrolysis of Compound of Example 17 Using Mannosidase

Compound (C18) was obtained in the same manner as in Example 4 except of using Compound (C17) obtained in Example 17 in place of Compound (C3) in Example 4.

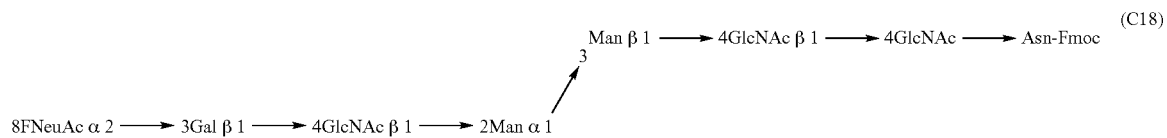

(C18)

The above asparagine-linked oligosaccharide corresponds to Compound (1) wherein R$^1$=H, R$^2$=formula (2), R=OH, R'=F and R"=OH.

Example 19

Hydrolysis of Compound of Example 15 Using Galactosidase

Compound (C19) was obtained in the same manner as in Example 5 except of using Compound (C15-3) obtained in Example 15 in place of Compound (C1-3) in Example 5.

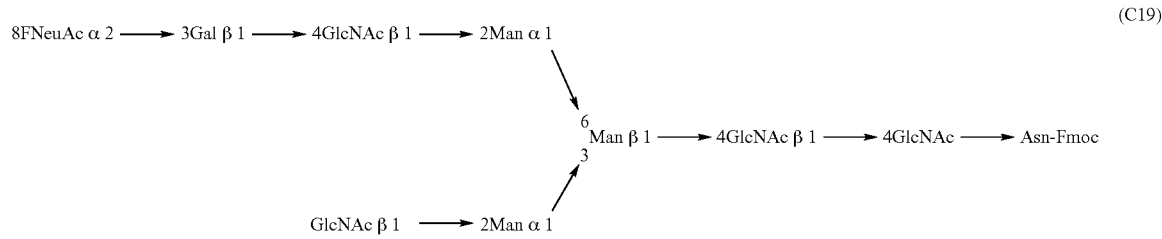

(C19)

The above asparagine-linked oligosaccharide corresponds to Compound (1) wherein $R^1$=formula (2), R=OH, R'=F, R''=OH and $R^2$=formula (4).

Example 20

Hydrolysis of Compound of Example 19 Using N-Acetylglucosaminidase

Compound (C20) was obtained in the same manner as in Example 6 except of using Compound (C19) obtained in Example 19 in place of Compound (C5) in Example 6.

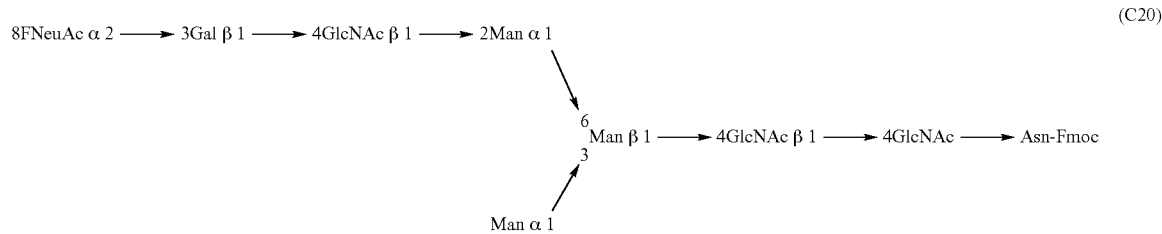

The above asparagine-linked oligosaccharide corresponds to Compound (1) wherein $R^1$=formula (2), R=OH, R'=F, R''=OH and $R^2$=formula (5).

Example 21

Hydrolysis of Compound of Example 20 Using Mannosidase

Compound (C21) was obtained in the same manner as in Example 7 except of using Compound (C20) obtained in Example 20 in place of Compound (C6) in Example 7.

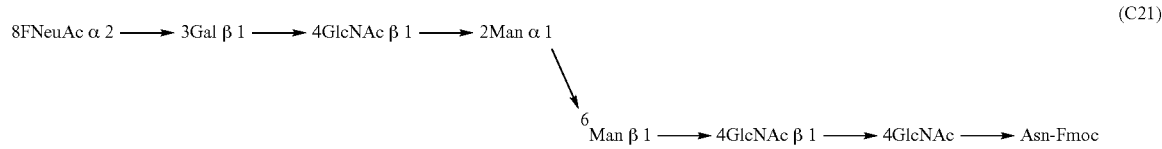

The above asparagine-linked oligosaccharide corresponds to Compound (1) wherein $R^1$=formula (2), R=OH, R'=F, R''=OH and $R^2$=H.

Example 22

Preparation of Asparagine-Linked di9''-deoxy-9''-fluoro-sialo(α2,3)oligosaccharide Wherein the Amino Group of the Asparagine was Protected with Fmoc Group (C22-1), and Two Kinds of Asparagine-Linked mono9''-deoxy-9''-fluoro-sialo(α2,3)oligosaccharide Wherein the Amino Group of the Asparagine was Protected with Fmoc Group (C22-2 and C22-3)

Asparagine-linked di9''-deoxy-9''-fluoro-sialo(α2,3)oligosaccharide wherein the amino group of the asparagine was protected with Fmoc group, and two kinds of asparagine-linked mono9''-deoxy-9''-fluoro-sialo(α2,3)oligosaccharide wherein the amino group of the asparagine was protected with Fmoc group shown below were obtained in the same manner as in Example 1 except of using CMP-9''-deoxy-9''-fluoro-sialic acid obtained in Reference Example 10.

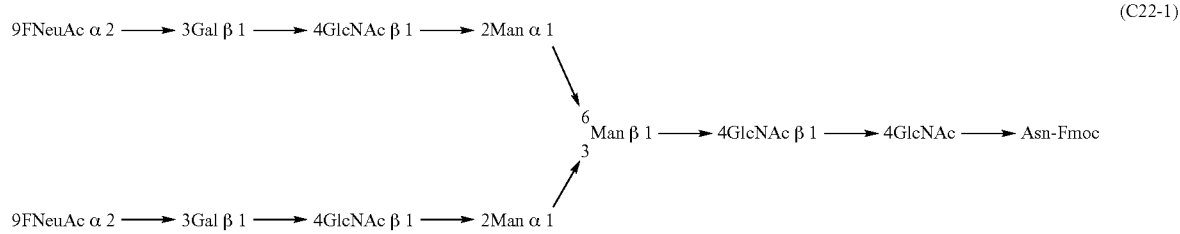

-continued (C22-2)
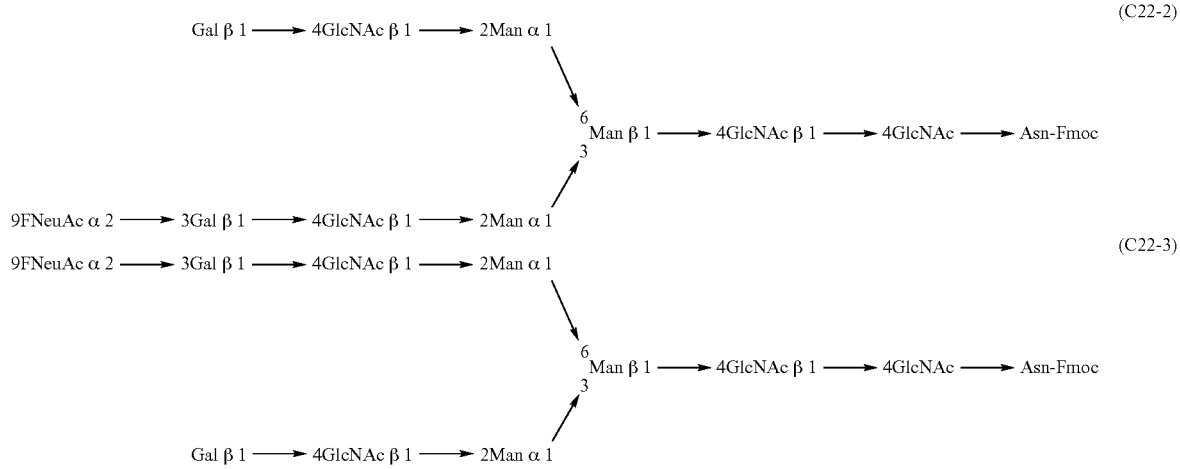

The above asparagine-linked oligosaccharide (C22-1) corresponds to Compound (1) wherein $R^1=R^2=$formula (2), R=OH, R'=OH and R"=F.

The above asparagine-linked oligosaccharide (C22-2) corresponds to Compound (1) wherein $R^1=$formula (3), $R^2=$formula (2), R=OH, R'=OH and R"=F.

The above asparagine-linked oligosaccharide (C22-3) corresponds to Compound (1) wherein $R^1=$formula (2), R=OH, R'=OH, R"=F and $R^2=$formula (3).

Example 23

Hydrolysis of Compound of Example 22 Using Galactosidase

Compound (C23) was obtained in the same manner as in Example 2 except of using Compound (C22-2) obtained in Example 22 in place of Compound (C1-2) in Example 2.

Compound (C23) is an asparagine-linked oligosaccharide corresponding to Compound (1) wherein $R^1=$formula (4), $R^2=$formula (2), R=OH, R'=OH and R"=F.

(C23)
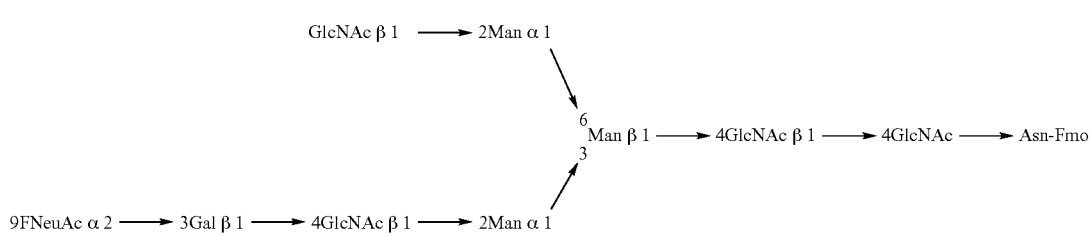

Example 24

Hydrolysis of Compound of Example 23 Using N-Acetylglucosaminidase

Compound (C24) was obtained in the same manner as in Example 3 except of using Compound (C23) obtained in Example 23 in place of Compound (C2) in Example 3.

Compound (C24) is an asparagine-linked oligosaccharide corresponding to Compound (1) wherein $R^1=$formula (5), $R^2=$formula (2), R=OH, R'=OH and R"=F.

(C24)
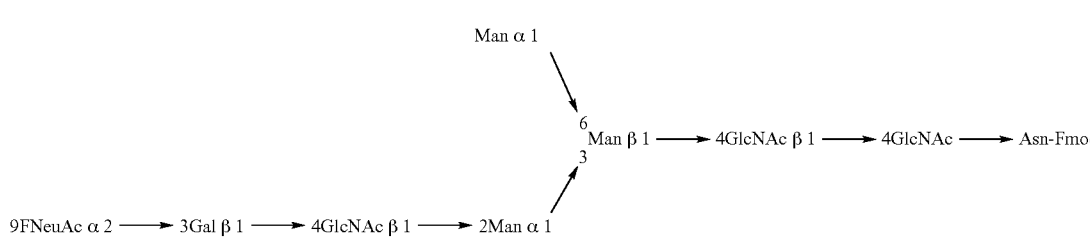

Example 25

Hydrolysis of Compound of Example 24 Using Mannosidase

Compound (C25) was obtained in the same manner as in Example 4 except of using Compound (C24) obtained in Example 24 in place of Compound (C3) in Example 4.

Compound (C25) is an asparagine-linked oligosaccharide corresponding to Compound (1) wherein $R^1$=H, $R^2$=formula (2), R=OH, R'=OH and R''=F.

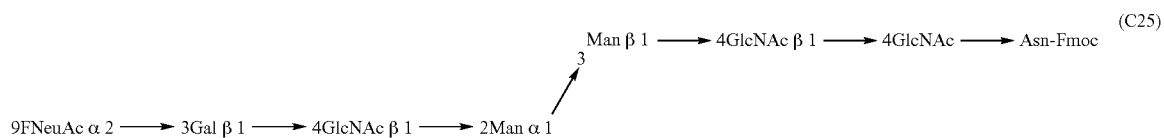
(C25)

Example 26

Hydrolysis of Compound of Example 22 Using Galactosidase

Compound (C26) was obtained in the same manner as in Example 5 except of using Compound (C22-3) obtained in Example 22 in place of Compound (C1-3) in Example 5.

Compound (C26) is an asparagine-linked oligosaccharide corresponding to Compound (1) wherein $R^1$=formula (2), R=OH, R'=OH R''=F and $R^2$=formula (4).

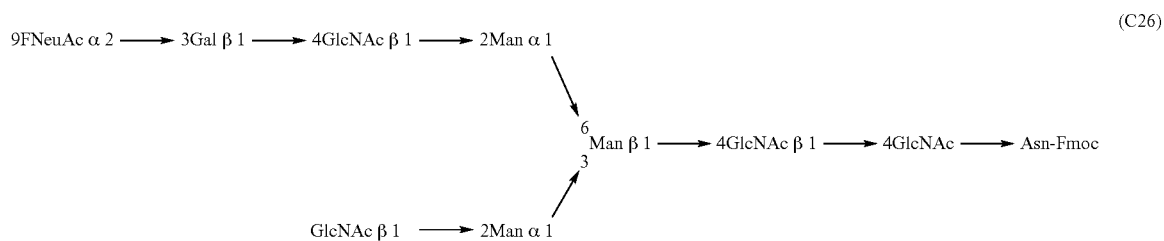
(C26)

Example 27

Hydrolysis of Compound of Example 26 Using N-acetylglucosaminidase

Compound (C27) was obtained in the same manner as in Example 6 except of using Compound (C26) obtained in Example 26 in place of Compound (C5) in Example 6.

Compound (C27) is an asparagine-linked oligosaccharide corresponding to Compound (1) wherein $R^1$=formula (2), R=OH, R'=OH, R''=F and $R^2$=formula (5).

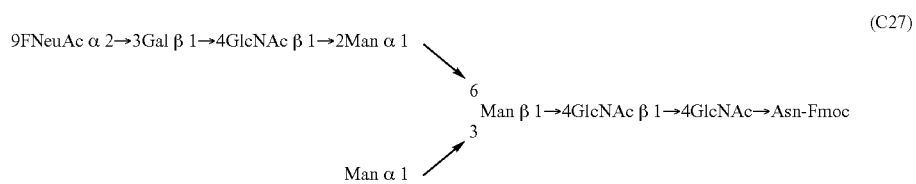
(C27)

Example 28

Hydrolysis of Compound of Example 27 Using Mannosidase

Compound (C28) was obtained in the same manner as in Example 7 except of using Compound (C27) obtained in Example 27 in place of Compound (C6) in Example 7.

Compound (C28) is an asparagine-linked oligosaccharide corresponding to Compound (1) wherein $R^1$=formula (2), R=OH, R'=OH, R''=F and $R^2$=H.

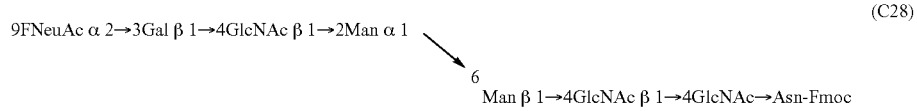

(C28)

Example 29

Preparation of Asparagine-Linked di7"-deoxy-7"-fluoro-sialo(2,6)oligosaccharide Wherein the Amino Group of the Asparagine was Protected with Fmoc Group (C29-1), and Two Kinds of Asparagine-Linked mono7"-deoxy-7"-fluoro-sialo(2,6)oligosaccharide Wherein the Amino Group of the Asparagine was Protected with Fmoc Group (C29-2 and C29-3)

Asparagine-linked di7"-deoxy-7"-fluoro-sialo(2,6)oligosaccharide wherein the amino group of the asparagine was protected with Fmoc group, and two kinds of asparagine-linked mono7"-deoxy-7"-fluoro-sialo(2,6)oligosaccharide wherein the amino group of the asparagine was protected with Fmoc group shown below were obtained in the same manner as in Example 1 except of using CMP-7"-deoxy-7"-fluoro-sialic acid obtained in Reference Example 7, α2,6-transferase which was commercially available and derived from a rat liver as a sialic acid transferase, and pH 6.0 of cacodylic acid buffer. Shown below are chemical formulae of (C29-1) to (C29-3).

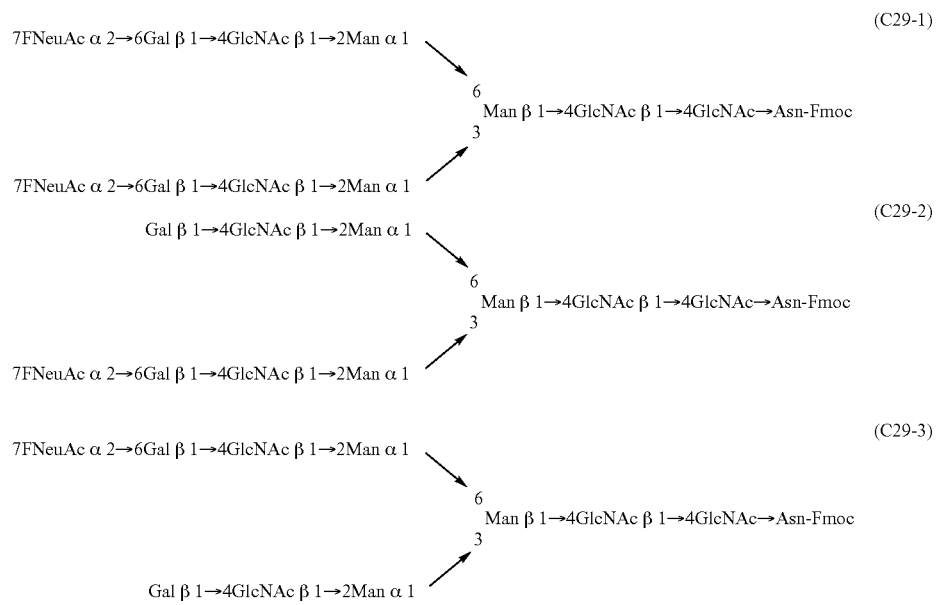

Example 30

Hydrolysis of Compound of Example 29 Using Galactosidase

Compound (C30) was obtained in the same manner as in Example 2 except of using Compound (C29-2) obtained in Example 29 in place of Compound (C1-2) in Example 2. Shown below is chemical formula of (C30).

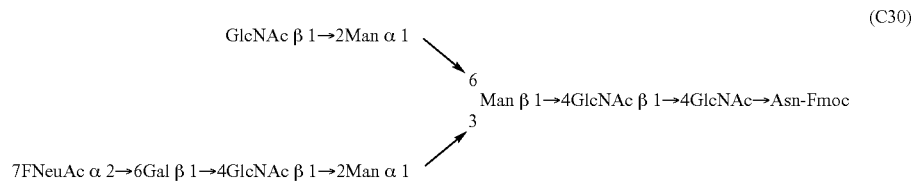

Example 31

Hydrolysis of Compound of Example 30 Using N-acetylglucosaminidase

Compound (C31) was obtained in the same manner as in Example 3 except of using Compound (C30) obtained in Example 30 in place of Compound (C2) in Example 3. Shown below is chemical formula of (C31).

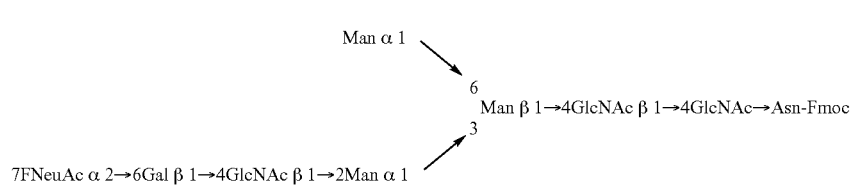

(C31)

Example 32

Hydrolysis of Compound of Example 31 Using Mannosidase

Compound (C32) was obtained in the same manner as in Example 4 except of using Compound (C31) obtained in Example 31 in place of Compound (C3) in Example 4. Shown below is chemical formula of (C32).

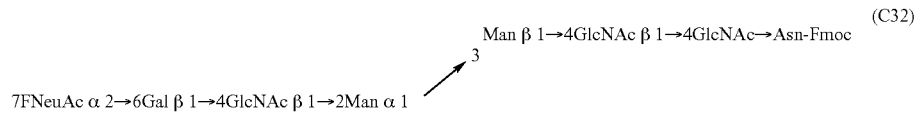

(C32)

Example 33

Hydrolysis of Compound of Example 29 Using Galactosidase

Compound (C33) was obtained in the same manner as in Example 5 except of using Compound (C29-3) obtained in Example 29 in place of Compound (C1-3) in Example 5. Shown below is chemical formula of (C33).

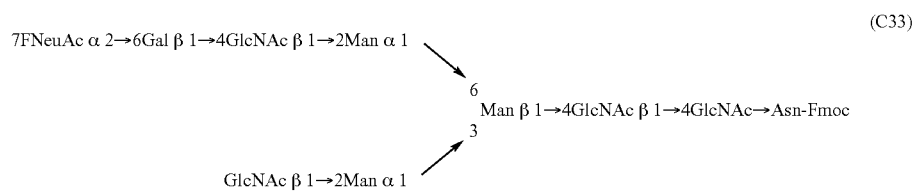

(C33)

Example 34

Hydrolysis of Compound of Example 33 Using N-acetylglucosaminidase

Compound (C34) was obtained in the same manner as in Example 6 except of using Compound (C33) obtained in Example 33 in place of Compound (C5) in Example 6. Shown below is chemical formula of (C34).

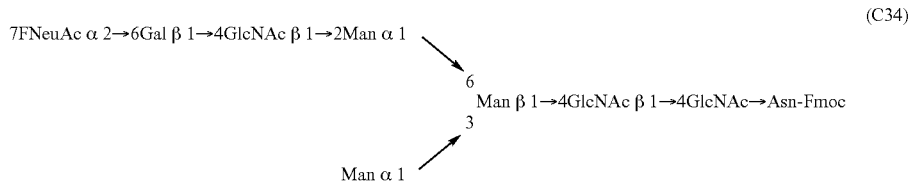
(C34)
Example 35
Hydrolysis of Compound of Example 34 Using Mannosidase
Compound (C35) was obtained in the same manner as in Example 7 except of using Compound (C34) obtained in Example 34 in place of Compound (C6) in Example 7. Shown below is chemical formula of (C35).
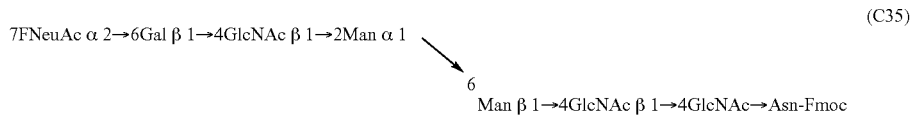
(C35)
Examples 36 to 49
In similar manners the following asparagine-linked oligosaccharide derivatives were obtained.
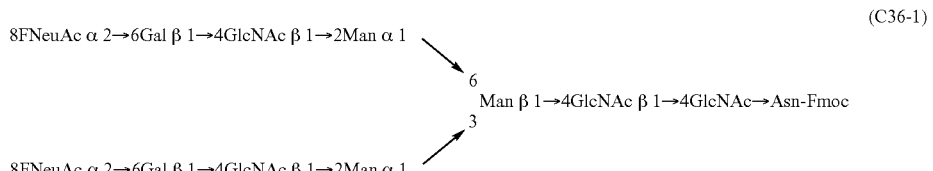
(C36-1)
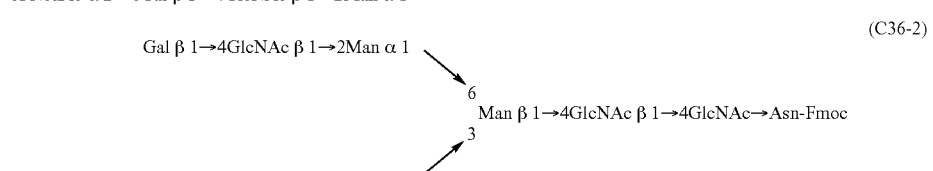
(C36-2)
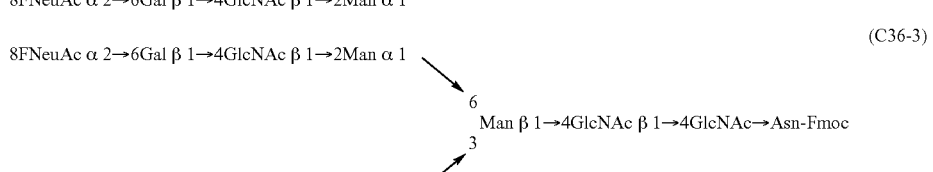
(C36-3)
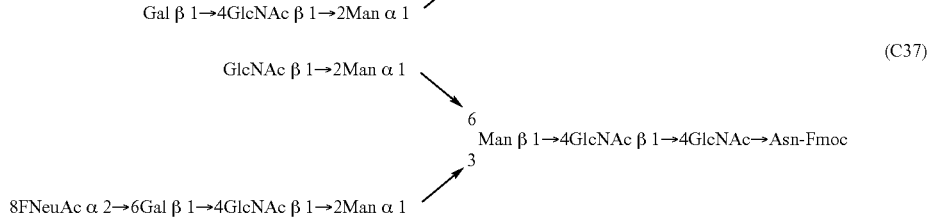
(C37)

-continued
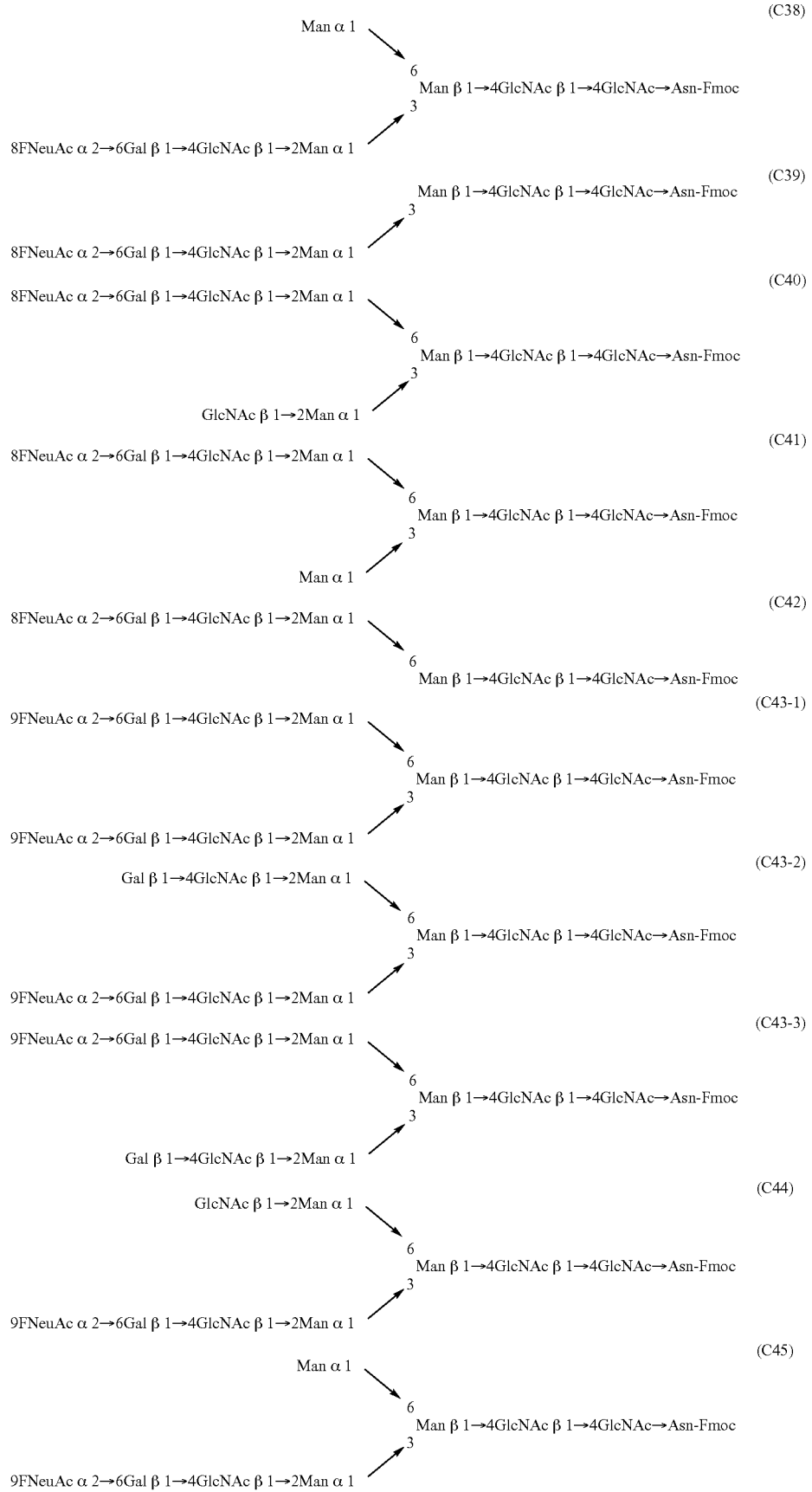

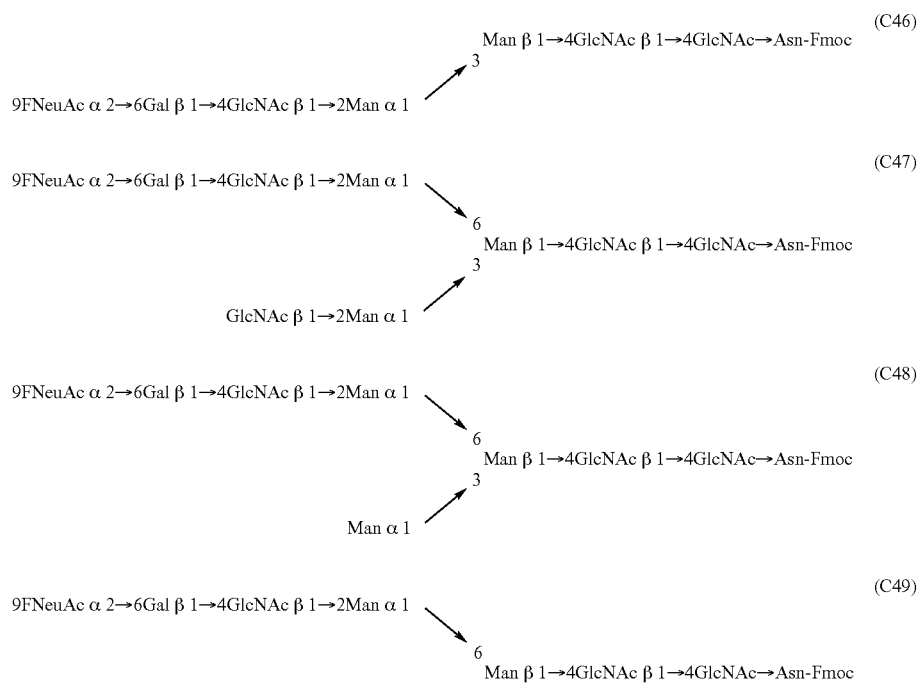

As a representative example, shown below is NMR data of 8Fα 2,6-undeca-saccharides-Asn-Fmoc (C36-1).

$^1$H NMR (400 MHz, D$_2$O, 30° C., HOD=4.81)

δ 8.01 (d, 2H, J=7.4, Fmoc), 7.80 (d, 2H, J=7.4, Fmoc), 7.59 (dd, 2H, J=7.4, Fmoc), 7.52 (bdd, 2H, J=7.4, Fmoc), 5.22 (s, 1H, Man4-H1), 5.08 (d, 1H, J=9.4, GlcNAc1-H1), 5.05 (s, 1H, Man4'-H-1), 4.85-4.95 (m, 1H), 4.55-4.75 (m), 4.53 (d, 1H, J=7.9), 4.43 (m, 1H), 4.35 (bs, 2H, Man3-H2), 4.28 (bs, 1H, Man4-H2), 4.10-4.25 (m, 2H), 2.75-2.85 (m, 1H, Asn-βCH), 2.63-2.70 (dd, 2H, Ja=3.9, Jb=12.0, NeuAc7,7'-H3eq), 2.55-2.65 (m, 1H, Asn-βCH), 2.16, 2.11, 2.08 (eachs, 15H, Acx5), 1.84 (s, 3H, Ac), 1.74 (dd, 1H, Ja=12.3, Jb=12.2, NeuAc7-H3ax).

Example 50

Deprotection of Fmoc Group of Asparagine-Linked Oligosaccharide Derivatives

All of the asparagine-linked oligosaccharide derivatives were subjected to the deprotection of the Fmoc group in accordance with the following procedures. First, 240 μL of N,N-dimethylformamide and 160 μL of morpholine were added per 1 μmol of the Fmoc form of the sugar chain asparagine, and the resulting mixture was subjected to reaction at room temperature under argon atmosphere. The termination of the reaction was confirmed by TLC (eluent: 1M ammonium acetate:isopropanol=8:5), and thereafter the mixture was cooled with ice water. To this mixture was added diethyl ether in an amount of 10 times that of the reaction solution, with stirring the mixture for 15 minutes, and thereafter the precipitates formed were filtered. The residue obtained was dissolved in water, and evaporated at 35° C. Further, a procedure of adding 3 mL of toluene thereto and evaporating the mixture was repeated three times. The residue was purified by reverse phase column chromatography (Cosmosil 75C$_{18}$-OPN, 15×100 mm, eluent: water) to obtain corresponding asparagine-linked oligosaccharides.

Example 51

Removal of Asparagine Residue of Asparagine-Linked Oligosaccharide

Asparagine residue was removed by reacting asparagine-linked oligosaccharide obtained in Example 50 with anhydrous hydrazine and then acetylating to prepare corresponding oligosaccharides.

Examples 52 to 69

Each of the asparagine-linked Fmoc-oligosaccharides prepared in Reference Examples 2, 3 and 8 to 13 and Examples 1 to 7 was dissolved, in an amount of 2 nmoles, in about 10 ml of Tris hydrochloric acid buffer. To the solution were added 200 nmoles of GDP-fucose and 0.5 mU of Fucosyltransferase V (human recombinant), and the mixture was allowed to stand at 37° C. for about 2 hours for reaction. The reaction mixture was diluted with 20 ml of ultrapure water and thereafter subjected to capillary electrophoresis (fused silica capillary, 50 mm i.d., 60 cm, buffer: Tris-borate, 8.3 in pH, 100 mM heptane sulfonate, applied voltage 27 kV, temp. 25° C., 214 mm) for separation to obtain the desired product.

Starting materials and products in each of examples are shown below.

TABLE 1
| Example 52 |
|---|
Starting material:
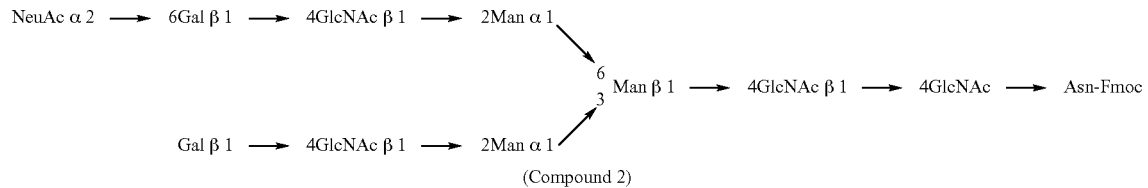
(Compound 2)
Product:
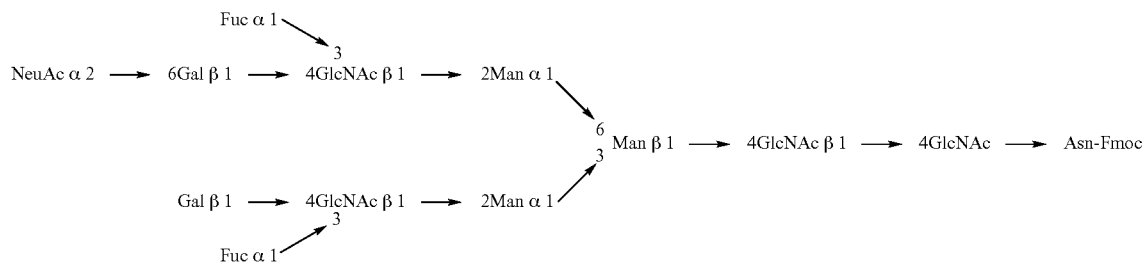
| Example 53 |
|---|
Starting material:
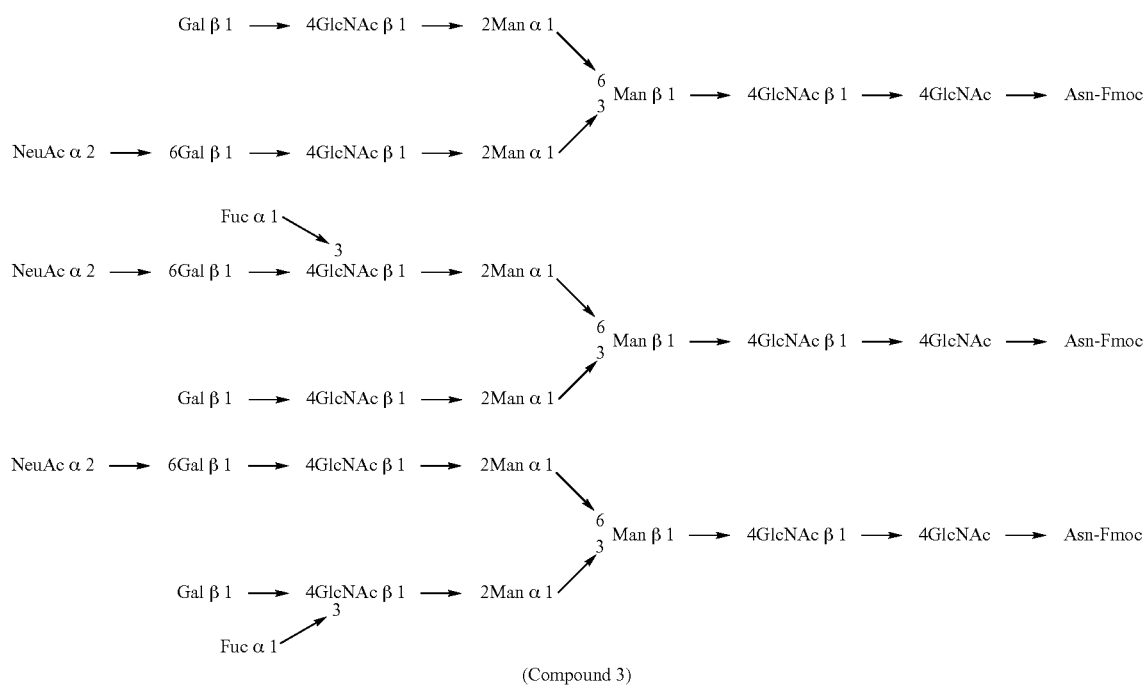
(Compound 3)

TABLE 1-continued
Product:
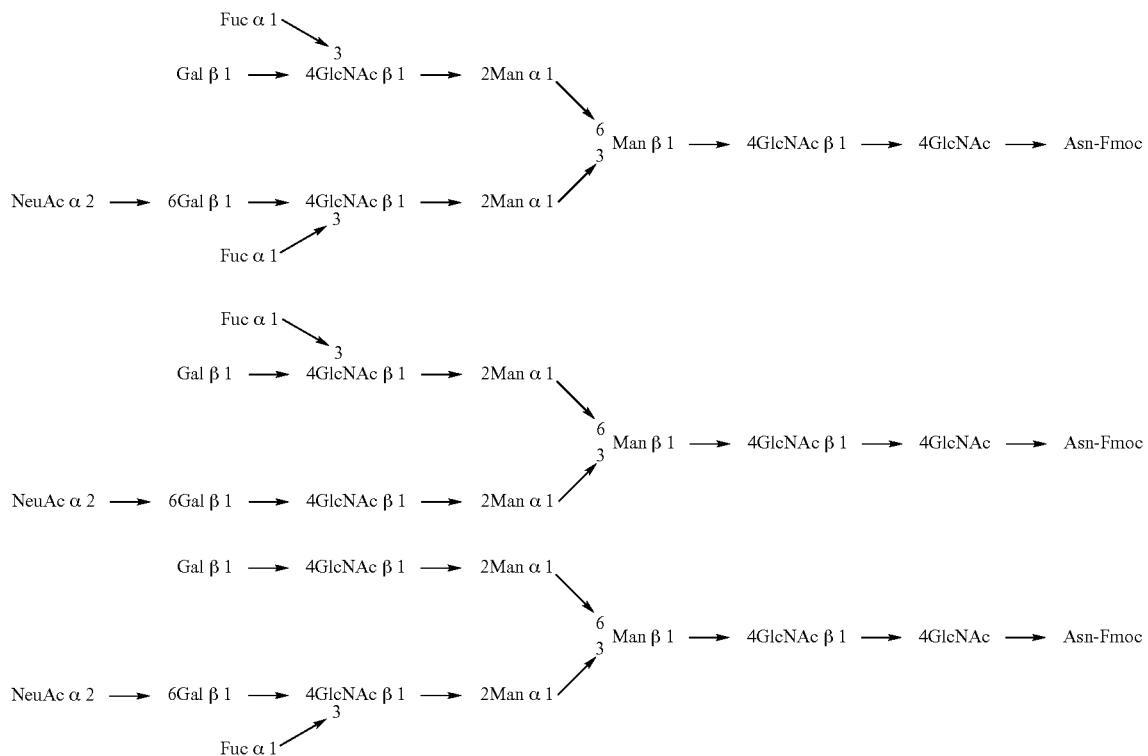
TABLE 2
Example 54
Starting material:
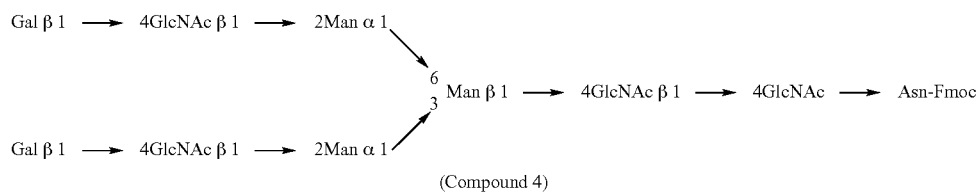
(Compound 4)

TABLE 2-continued
Product:
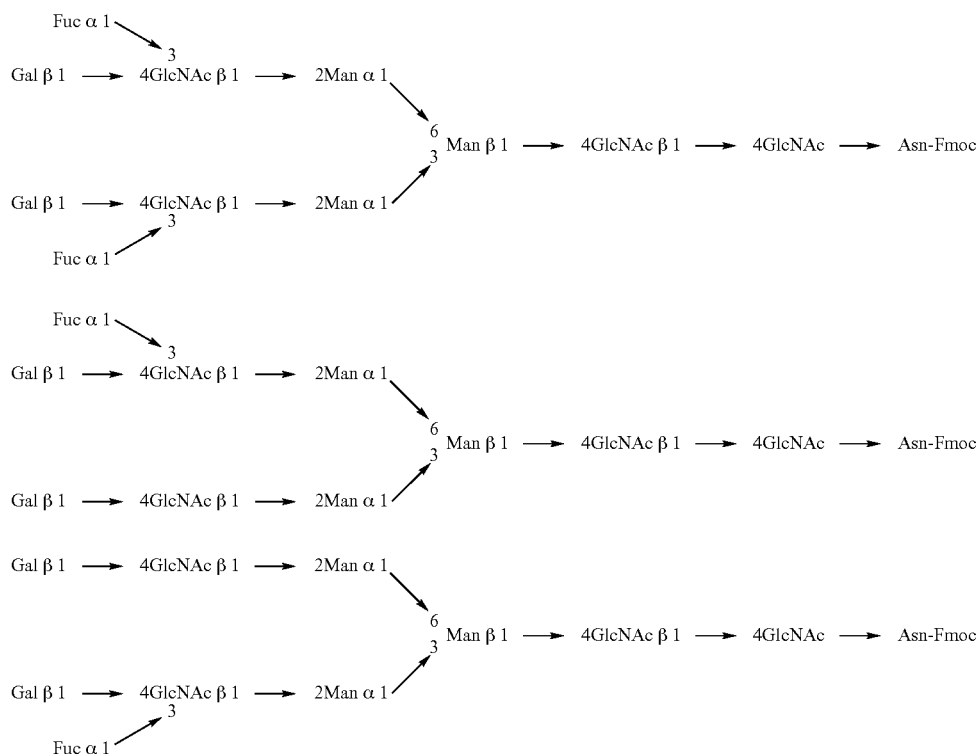
Example 55
Starting material:
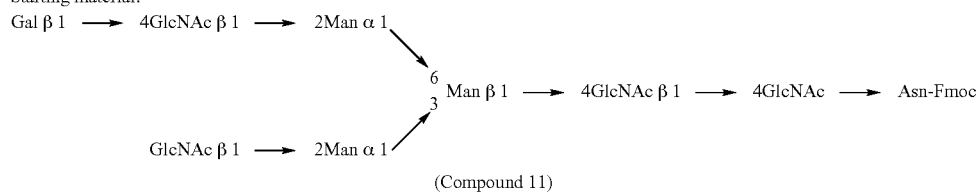
(Compound 11)
Product:
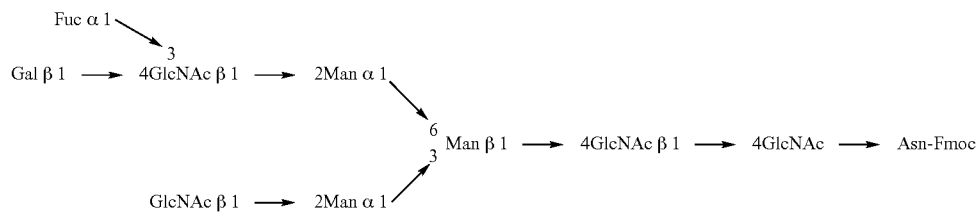
Example 56
Starting material:
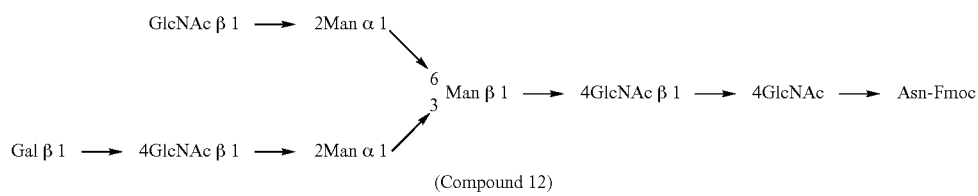
(Compound 12)

TABLE 2-continued
Product:
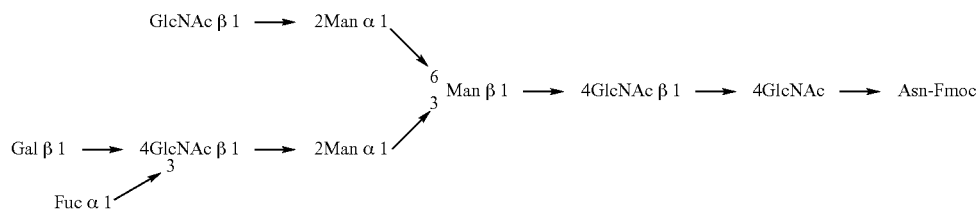
Example 57
Starting material:
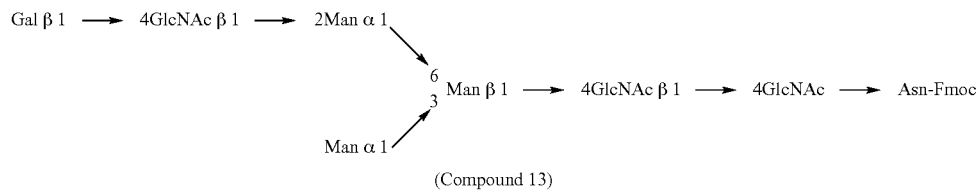
(Compound 13)
Product:
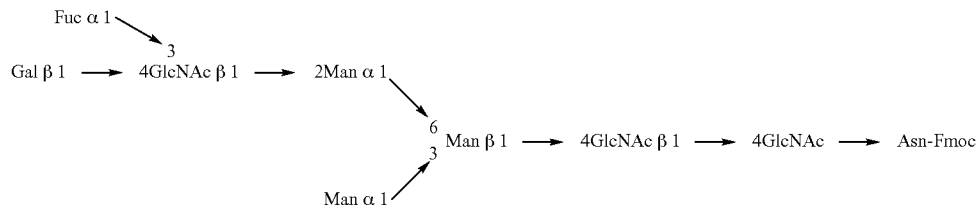
Example 58
Starting material:
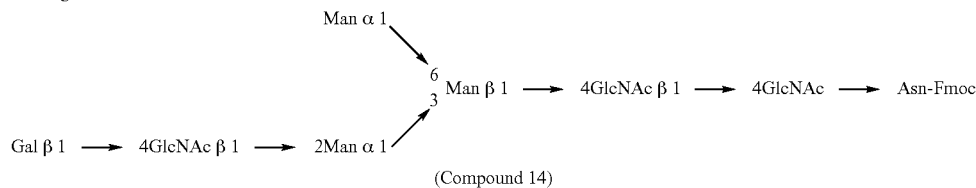
(Compound 14)
Product:
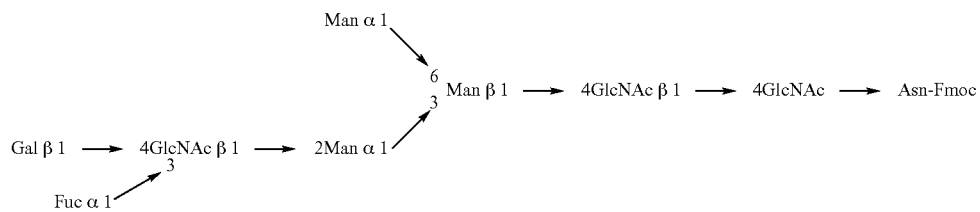
Example 59
Starting material:
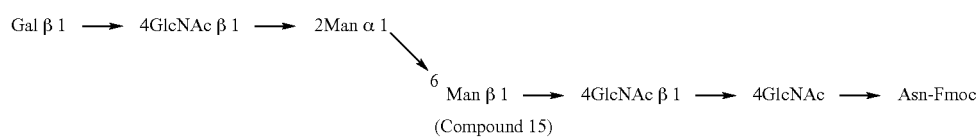
(Compound 15)

TABLE 2-continued
Product:
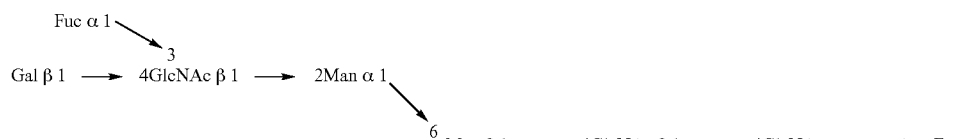
Example 60
Starting material:
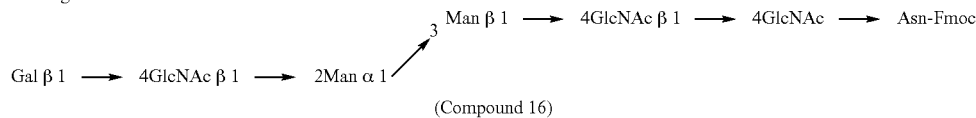
(Compound 16)
Product:
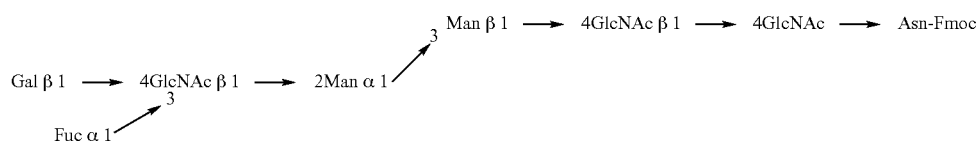
TABLE 3
Example 61
Starting material:
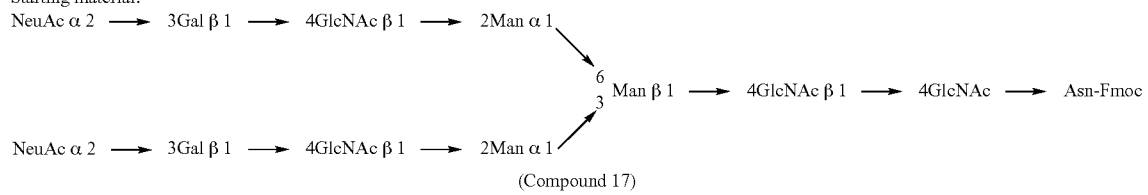
(Compound 17)
Product:
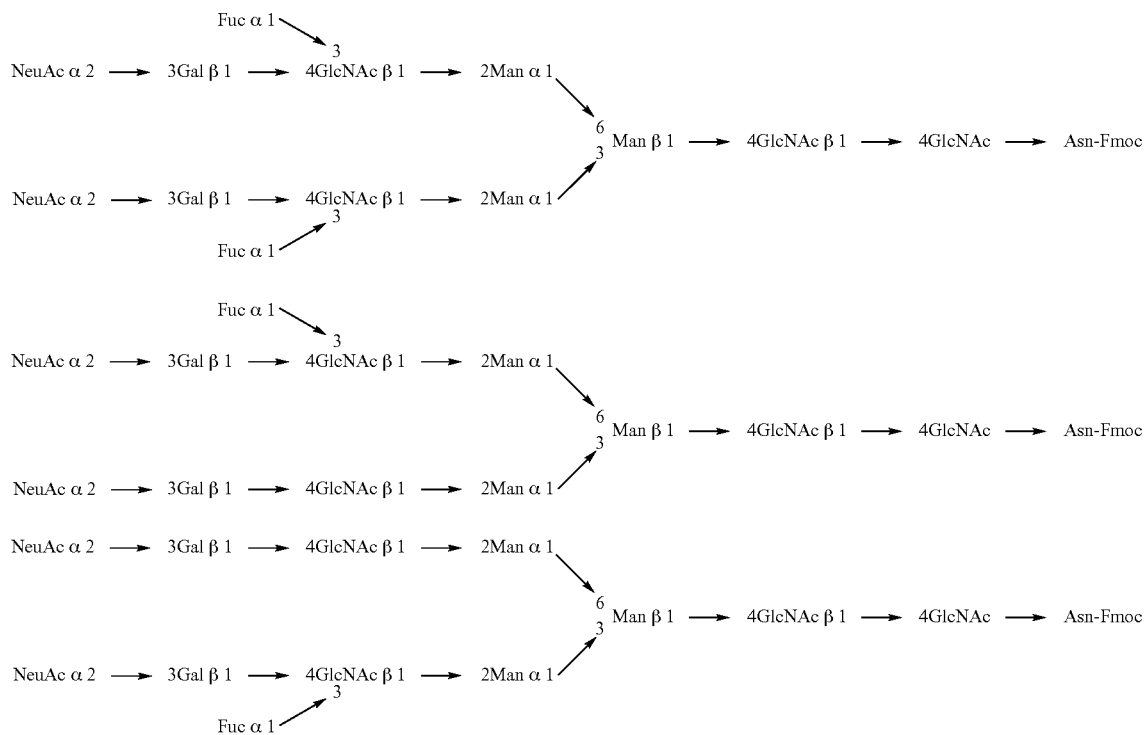

TABLE 3-continued
Example 62
Starting material:
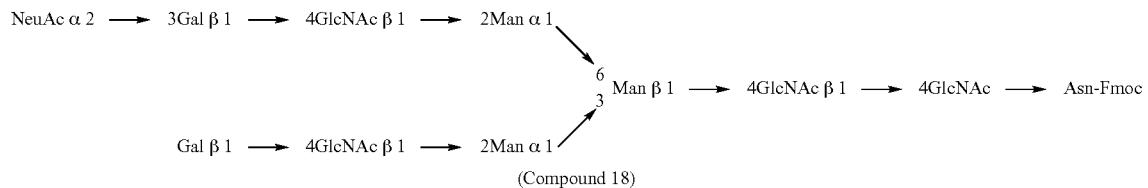
(Compound 18)
Product:
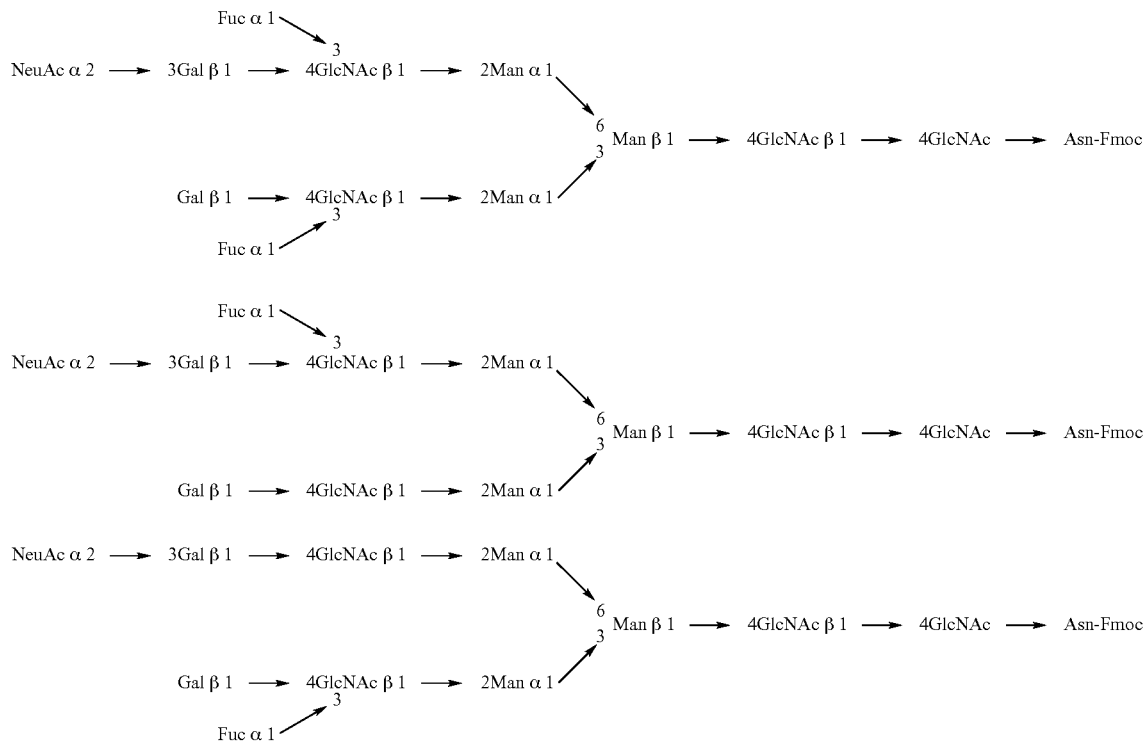
TABLE 4
Example 63
Starting material:
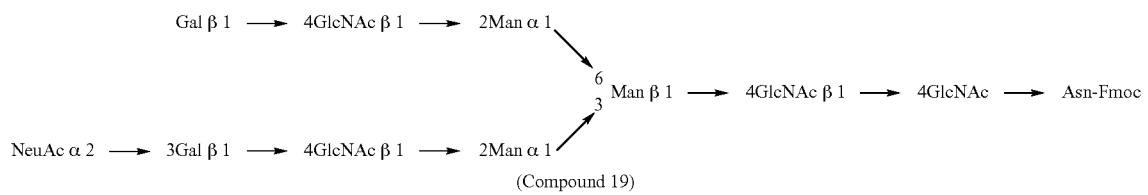
(Compound 19)

TABLE 4-continued
Product:
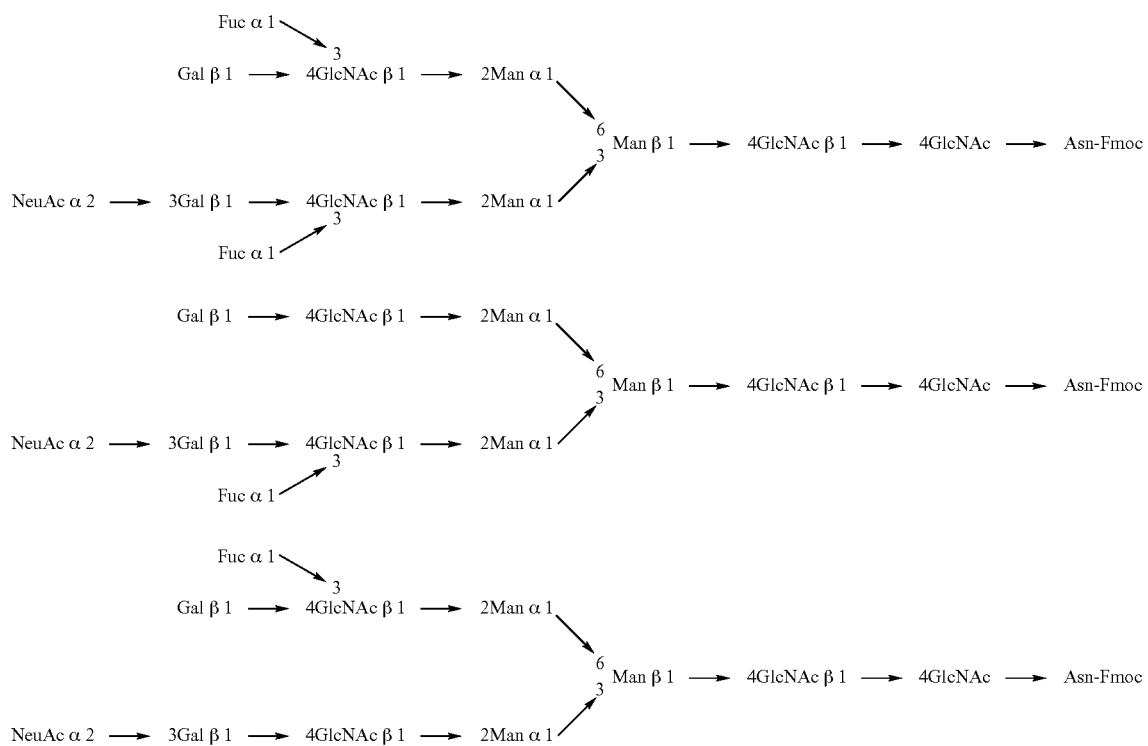
Example 64
Starting material:
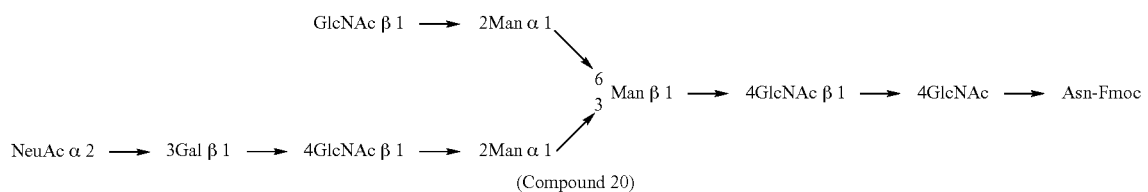
(Compound 20)
Product:
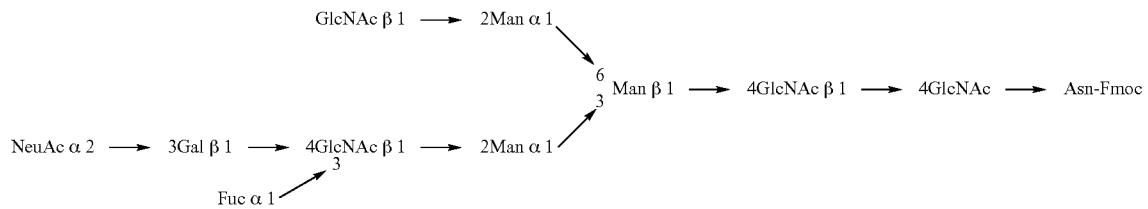
Example 65
Starting material:
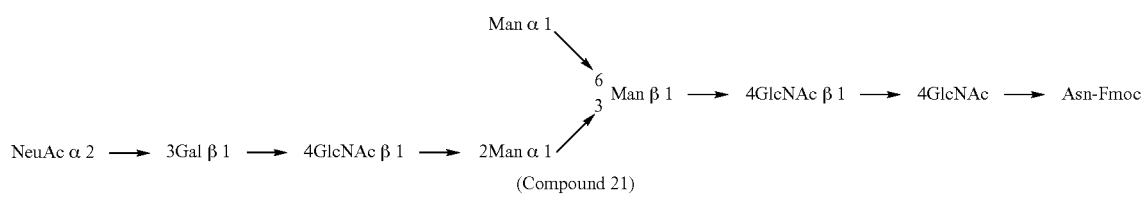
(Compound 21)

TABLE 4-continued
Product:
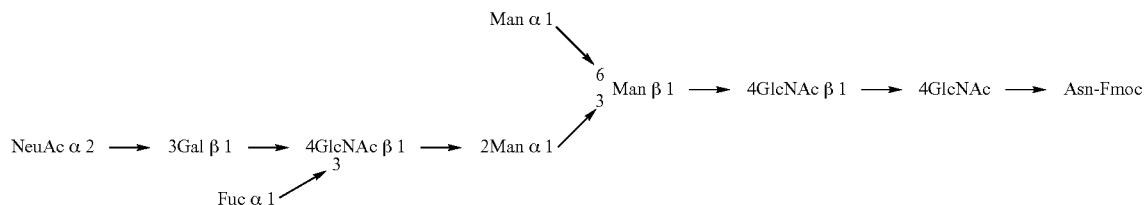
Example 66
Starting material:
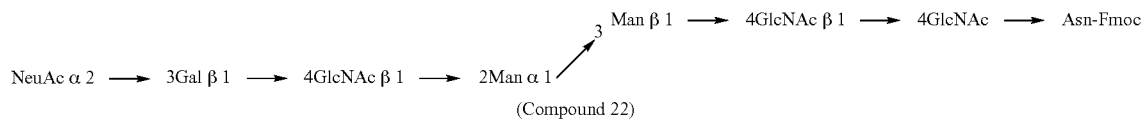
(Compound 22)
Product:
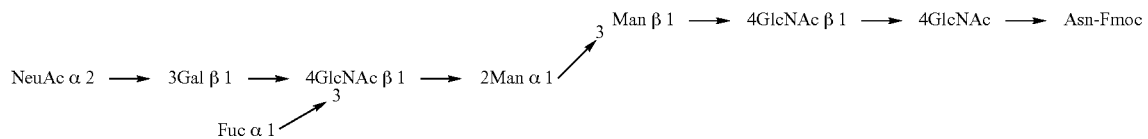
Example 67
Starting material:
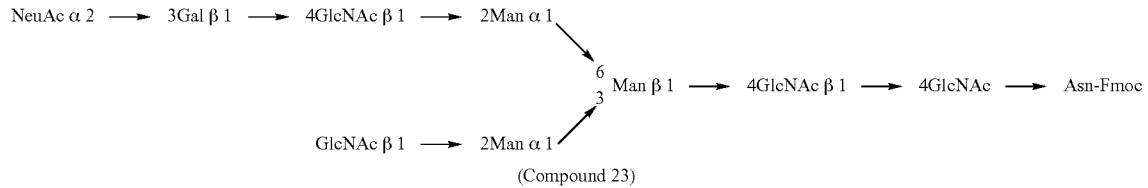
(Compound 23)
Product:
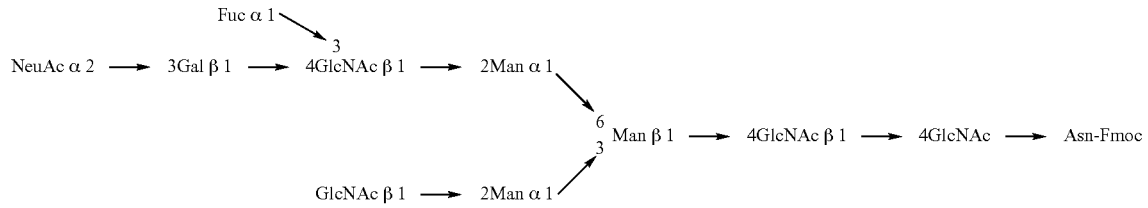
Example 68
Starting material:
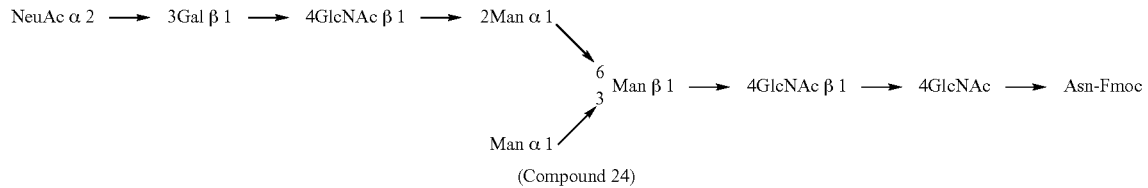
(Compound 24)

TABLE 4-continued

Product:

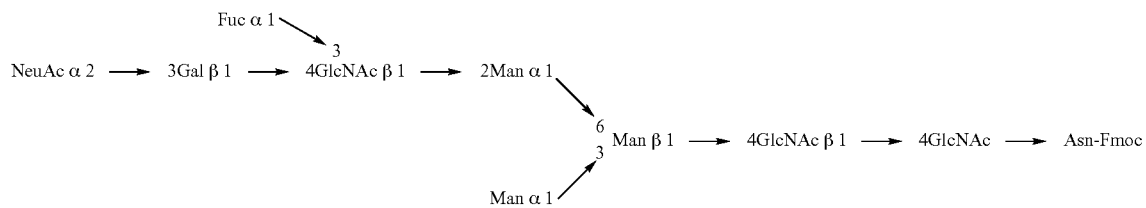

Example 69

Starting material:

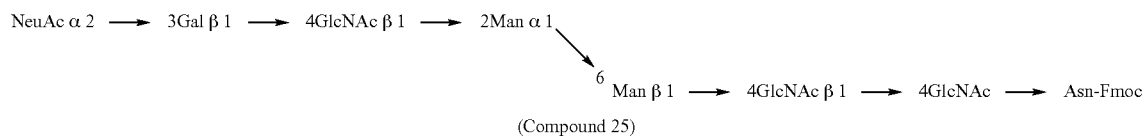
(Compound 25)

Product:

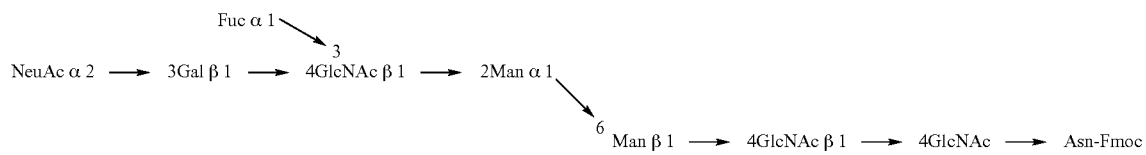

The invention claimed is:

1. An asparagine-linked α2,3-oligosaccharide derivative having undeca- to hepta-saccharides containing fluorine and represented by the formula (1) given below (1)

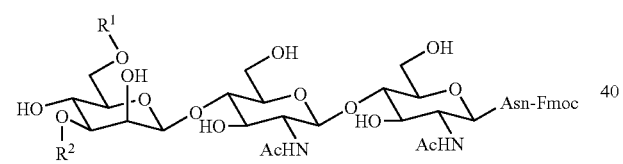

wherein $R^1$ and $R^2$ are each a hydrogen atom or one of the groups represented by the formulae (2) to (5) given below and may be the same or different, provided that one of $R^1$ and $R^2$ should always be the group of the formula (2)

(2)

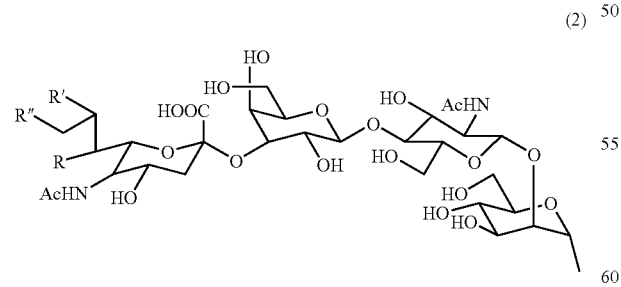

wherein R, R' and R" are in the following combinations:
(a) R=F, R'=OH, R"=OH;
(b) R=OH, R'=F, R"=OH;
(c) R=OH, R'=OH, R"=F; or
(d) R=OH, R'=OH, R"=OH;

(3)

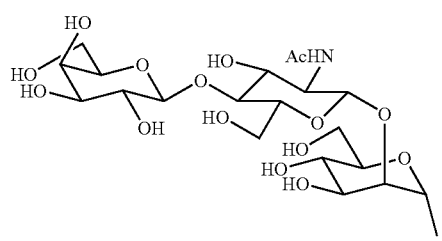

(4)

(5)

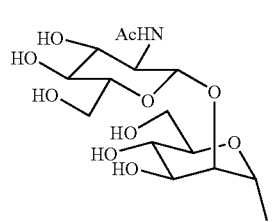

2. An asparagine-linked α2,6-oligosaccharide derivative having undeca- to hepta-saccharides, containing fluorine and represented by the formula (6) given below (6)

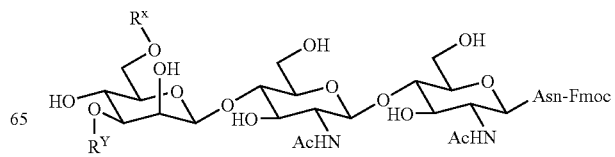

wherein $R^X$ and $R^Y$ are each a hydrogen atom, a group represented by the formula (7) given below or one of the groups represented by the formulae (3) to (5) given below, provided that one of $R^X$ and $R^Y$ should always be a group of the formula (7)

(3)

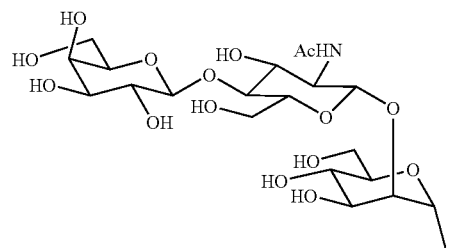

(4)

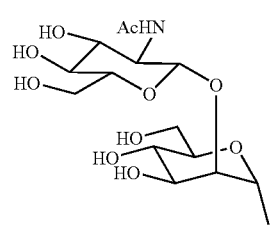

(5)

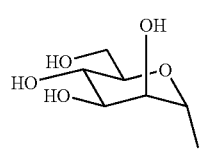

(7)

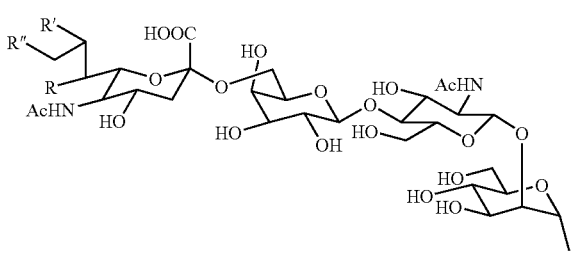

wherein R, R' and R" are in the following combinations:
(a) R=F, R'=OH, R"=OH;
(b) R=OH, R'=F, R"=OH; or
(c) R=OH, R'=OH, R"=F.

3. An asparagine-linked α2,3-oligosaccharide having undeca- to hepta-saccharides containing fluorine and represented by the formula (8) given below (8)

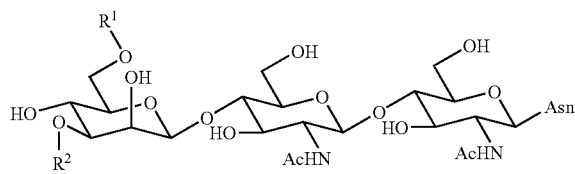

wherein $R^1$ and $R^2$ are each a hydrogen atom or one of the groups represented by the formulae (2) to (5) given below and may be the same or different, provided that one of $R^1$ and $R^2$ should always be the group of the formula (2)

(2)

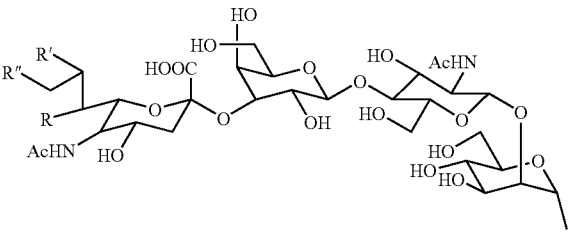

wherein R, R' and R" are in the following combinations:
(a) R=F, R'=OH, R"=OH;
(b) R=OH, R'=F, R"=OH;
(c) R=OH, R'=OH, R"=F; or
(d) R=OH, R'=OH, R"=OH;

(3)

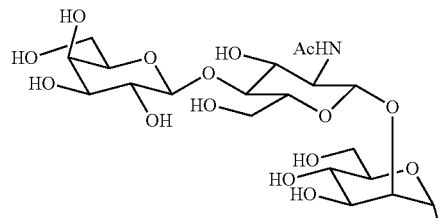

(4)

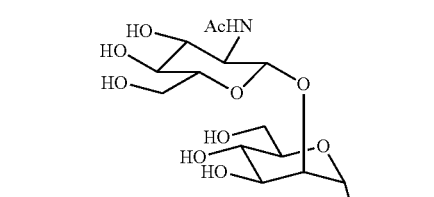

(5)

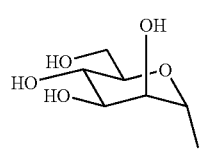

4. An asparagine-linked α2,6-oligosaccharide having undeca- to hepta-saccharides, containing fluorine and represented by the formula (9) given below (9)

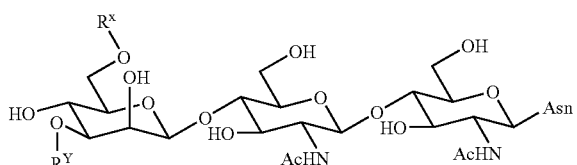

wherein $R^X$ and $R^Y$ are each a hydrogen atom, a group represented by the formula (7) given below or one of the groups represented by the formulae (3) to (5) given below, provided that one of $R^X$ and $R^Y$ should always be a group of the formula (7)

(3)

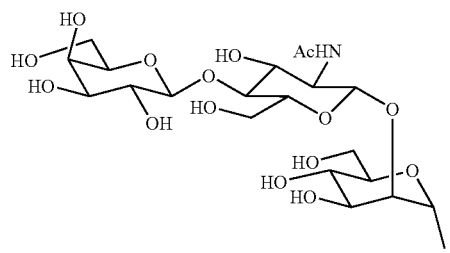

(4)

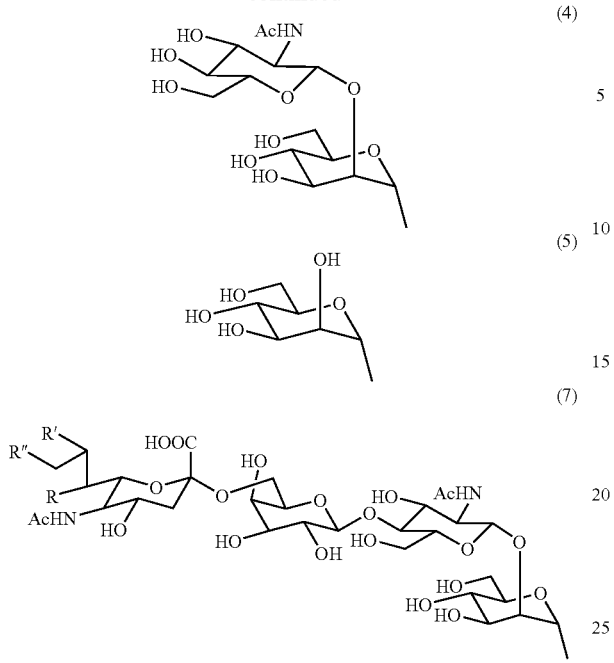

(5)

(7)

wherein R, R' and R" are in the following combinations:
(a) R=F, R'=OH, R"=OH;
(b) R=OH, R'=F, R"=OH; or
(c) R=OH, R'=OH, R"=F.

5. An α2,3-oligosaccharide having undeca- to hepta-saccharides containing fluorine and represented by the formula (10) given below (10)

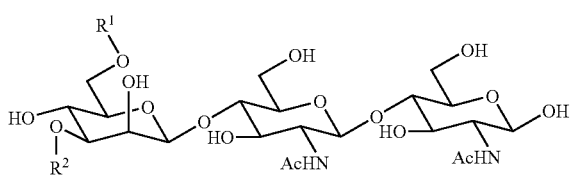

wherein $R^1$ and $R^2$ are each a hydrogen atom or one of the groups represented by the formulae (2) to (5) given below and may be the same or different, provided that one of $R^1$ and $R^2$ should always be the group of the formula (2)

(2)

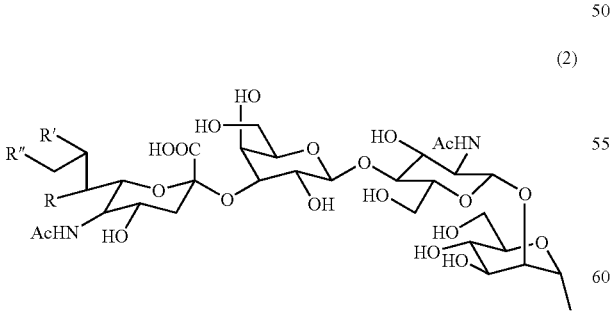

wherein R, R' and R" are in the following combinations:
(a) R=F, R'=OH, R"=OH;
(b) R=OH, R'=F, R"=OH;
(c) R=OH, R'=OH, R"=F; or
(d) R=OH, R'=OH, R"=OH;

(3)

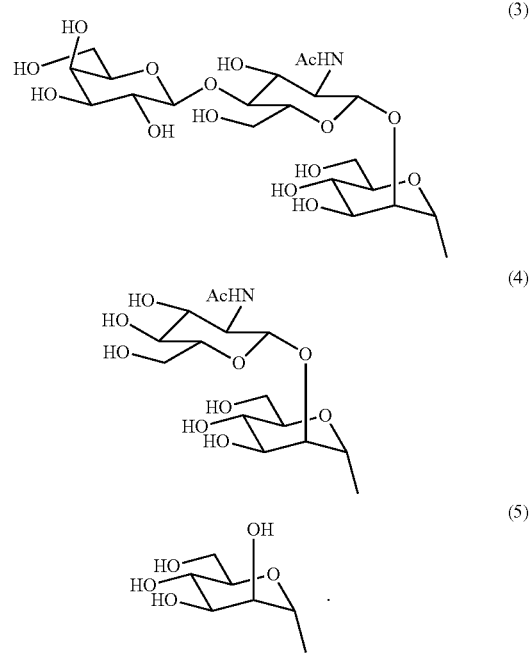

(4)

(5)

6. An α2,6-oligosaccharide having undeca- to hepta-saccharides, containing fluorine and represented by the formula (11) given below (11)

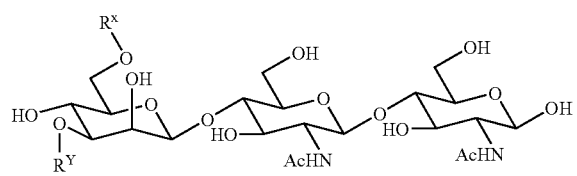

wherein $R^X$ and $R^Y$ are each a hydrogen atom, a group represented by the formula (7) given below or one of the groups represented by the formulae (3) to (5) given below, provided that one of $R^X$ and $R^Y$ should always be a group of the formula (7)

(3)

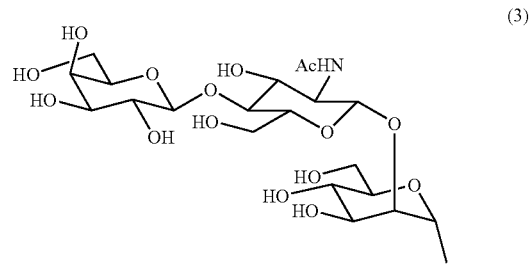

(4)

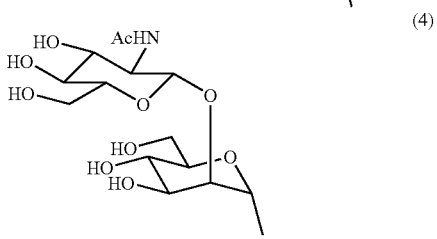

-continued (5)

(7)

wherein R, R' and R" are in the following combinations:
(a) R=F, R'=OH, R"=OH;
(b) R=OH, R'=F, R"=OH; or
(c) R=OH, R'=OH, R"=F.

7. A process for preparing an asparagine-linked α2,3-disialooligosaccharide derivative having undecasaccharide and represented by the formula (12) given below, the process comprising:
transferring sialic acid or a sialic acid derivative to an asparagine-linked oligosaccharide protected with a lipophilic protective group using a sialic acid transferase; and
subjecting the resulting asparagine-linked oligosaccharide protected with a lipophilic protective group to chromatography for separation (12)

wherein R¹ and R² are each a group represented by the formula (2)

(2)

wherein R, R' and R" are in the following combinations:
(a) R=F, R'=OH, R"=OH;
(b) R=OH, R'=F, R"=OH;
(c) R=OH, R'=OH, R"=F; or
(d) R=OH, R'=OH, R"=OH.

8. A process for preparing an asparagine-linked α2,3-monosialooligosaccharide derivative having decasaccharide, containing fluorine and represented by the formula (13) given below, the process comprising:

transferring sialic acid or a sialic acid derivative to an asparagine-linked oligosaccharide protected with a lipophilic protective group using a sialic acid transferase; and
subjecting the resulting asparagine-linked oligosaccharide protected with a lipophilic protective group to chromatography for separation (13)

wherein one of R¹ and R² is a group represented by the formula (2), and the other thereof is a group represented by the formula (3)

(2)

wherein R, R' and R" are in the following combinations:
(a) R=F, R'=OH, R"=OH;
(b) R=OH, R'=F, R"=OH;
(c) R=OH, R'=OH, R"=F; or
(d) R=OH, R'=OH, R"=OH;

(3)

9. A process for preparing an asparagine-linked α2,6-disialooligosaccharide derivative having undecasaccharide, containing fluorine and represented by the formula (17) given below, the process comprising:
transferring sialic acid or a sialic acid derivative to an asparagine-linked oligosaccharide protected with a lipophilic protective group using a sialic acid transferase; and
subjecting the resulting asparagine-linked oligosaccharide protected with a lipophilic protective group to chromatography for separation (17)

wherein $R^X$ and $R^Y$ are each a group represented by the formula (7)

(7)

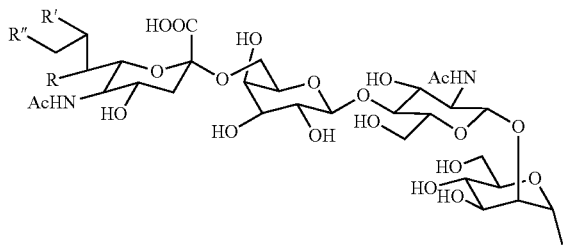

wherein R, R' and R" are in the following combinations:
(a) R=F, R'=OH, R"=OH;
(b) R=OH, R'=F, R"=OH; or
(c) R=OH, R'=OH, R"=F.

10. A process for preparing an asparagine-linked α2,6-monosialooligosaccharide derivative having decasaccharide, containing fluorine and represented by the formula (18) given below, the process comprising:
transferring sialic acid or a sialic acid derivative to an asparagine-linked oligosaccharide protected with a lipophilic protective group using a sialic acid transferase; and
subjecting the resulting asparagine-linked oligosaccharide protected with a lipophilic protective group to chromatography for separation (18)

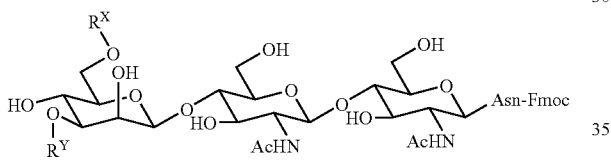

wherein one of $R^X$ and $R^Y$ is a group represented by the formula (7), and the other thereof is a group represented by the formula (3)

(7)

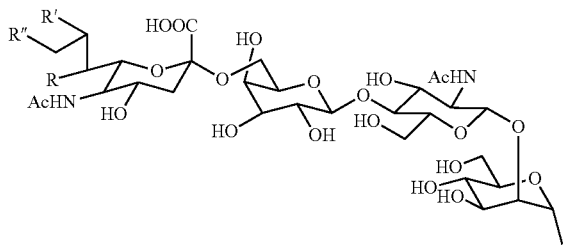

wherein R, R' and R" are in the following combinations:
(a) R=F, R'=OH, R"=OH;
(b) R=OH, R'=F, R"=OH; or
(c) R=OH, R'=OH, R"=F;

(3)

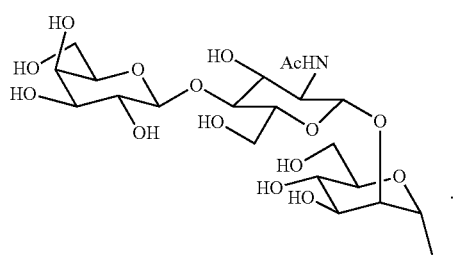

11. A process for preparing an asparagine-linked α2,3-oligosaccharide having undeca- to hepta-saccharides, containing fluorine and represented by the formula (8)

(8)

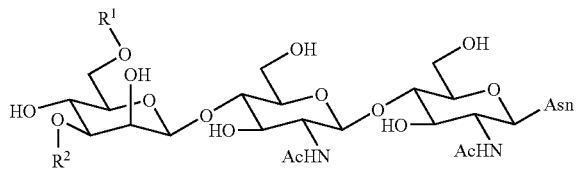

the process comprising removing the protective group from an asparagine-linked α2,3-oligosaccharide derivative having undeca- to hepta-saccharides and represented by the formula (1)

(1)

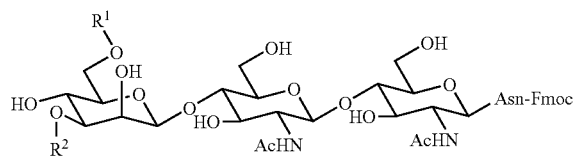

wherein $R^1$ and $R^2$ are each a hydrogen atom or one of the groups represented by the formulae (2) to (5) given below and may be the same or different, provided that one of $R^1$ and $R^2$ should always be the group of the formula (2)

(2)

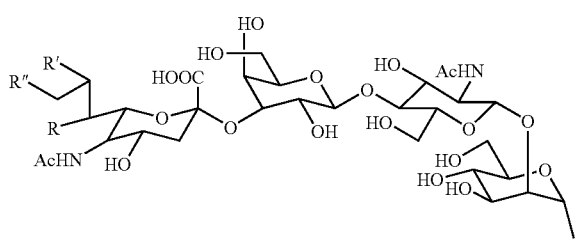

wherein R, R' and R" are in the following combinations:
(a) R=F, R'=OH, R"=OH;
(b) R=OH, R'=F, R"=OH;
(c) R=OH, R'=OH, R"=F; or
(d) R=OH, R'=OH, R"=OH;

(3)

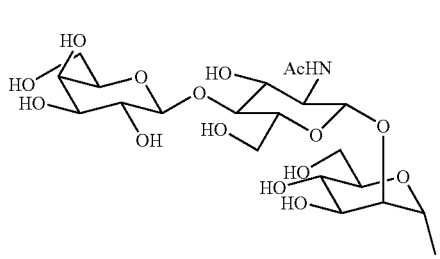

-continued

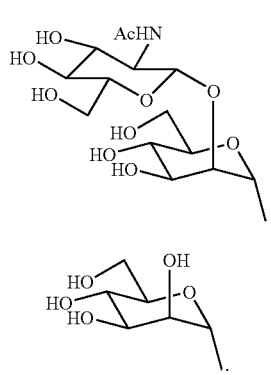
(4)

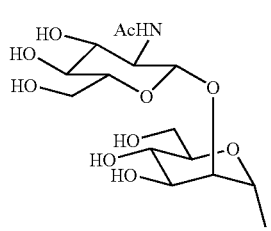
(5)

12. A process for preparing an asparagine-linked α2,6-oligosaccharide having undeca- to hepta-saccharides, containing fluorine and represented by the formula (9)

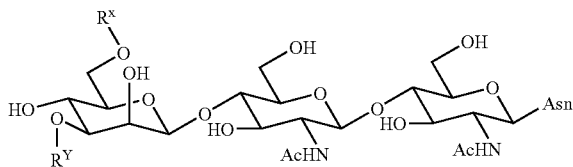
(9)

the process comprising removing the protective group from an asparagine-linked α2,6-oligosaccharide derivative having undeca- to hepta-saccharides and represented by the formula (6)

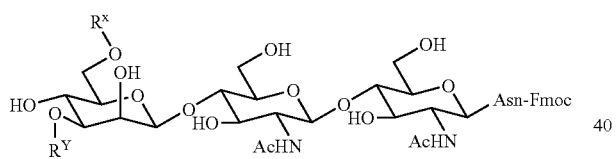
(6)

wherein $R^X$ and $R^Y$ are each a hydrogen atom, a group represented by the formula (7) given below or one of the groups represented by the formulae (3) to (5) given below, provided that one of $R^X$ and $R^Y$ should always be a group of the formula (7)

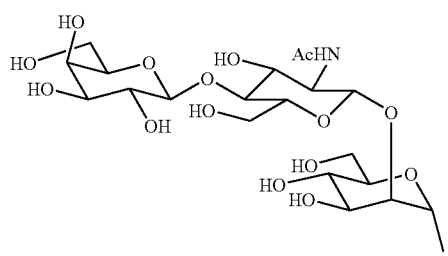
(3)

(4)

-continued

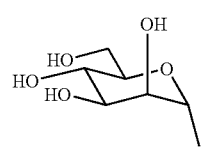
(5)

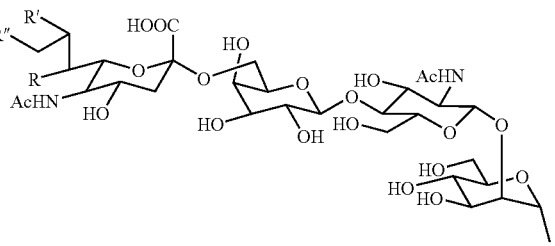
(7)

wherein R, R' and R" are in the following combinations:
(a) R=F, R'=OH, R"=OH;
(b) R=OH, R'=F, R"=OH; or
(c) R=OH, R'=OH, R"=F.

13. A process for preparing an α2,3-oligosaccharide having undeca- to hepta-saccharides, containing fluorine and represented by the formula (10)

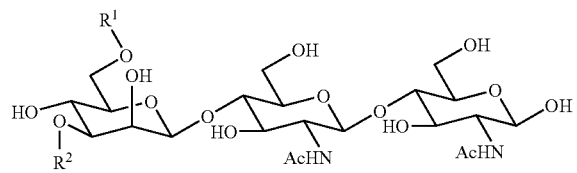
(10)

the process comprising removing the asparagine residue from an asparagine-linked α2,3-oligosaccharide having undeca- to hepta-saccharides and represented by the formula (8)

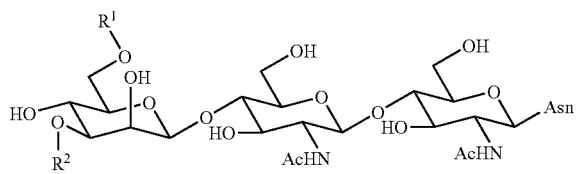
(8)

wherein $R^1$ and $R^2$ are each a hydrogen atom or one of the groups represented by the formulae (2) to (5) given below and may be the same or different, provided that one of $R^1$ and $R^2$ should always be the group of the formula (2)

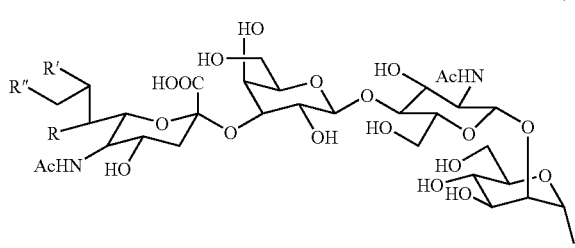
(2)

wherein R, R' and R" are in the following combinations:
(a) R=F, R'=OH, R"=OH;
(b) R=OH, R'=F, R"=OH;
(c) R=OH, R'=OH, R"=F; or
(d) R=OH, R'=OH, R"=OH;

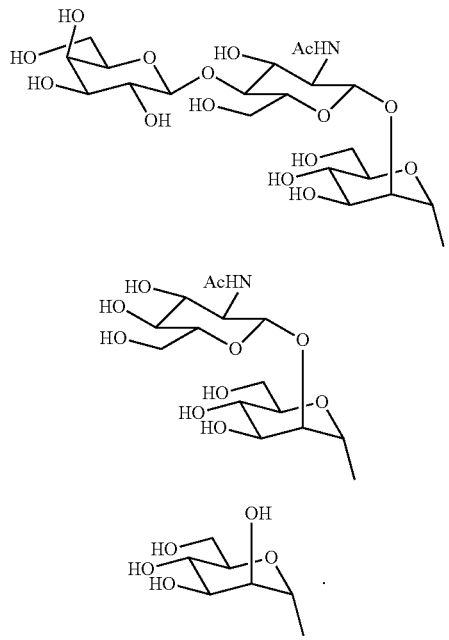

14. A process for preparing an α2,6-oligosaccharide having undeca- to hepta-saccharides, containing flourine and represented by the formula (11)

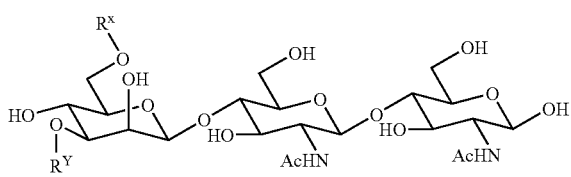

the process comprising removing the asparagine residue from an asparagine-linked α2,6-oligosaccharide having undeca- to hepta-saccharides and represented by the formula (9)

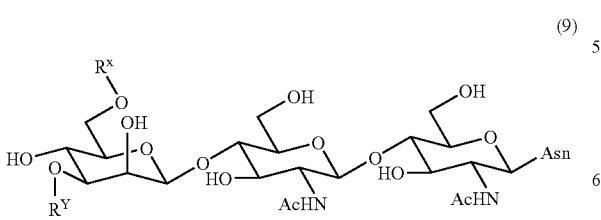

wherein $R^X$ and $R^Y$ are each a hydrogen atom, a group represented by the formula (7) given below or one of the groups represented by the formulae (3) to (5) given below, provided that one of $R^X$ and $R^Y$ should always be a group of the formula (7)

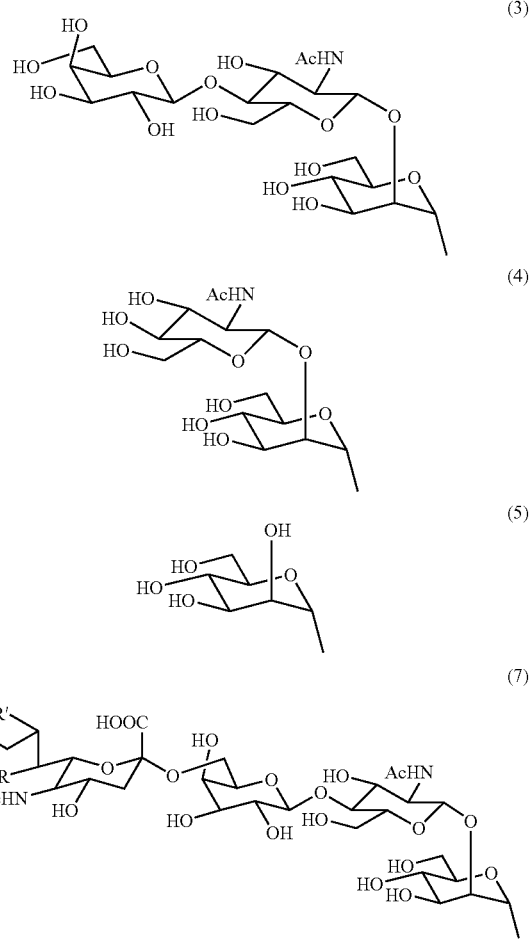

wherein R, R' and R" are in the following combinations:
(a) R=F, R'=OH, R"=OH;
(b) R=OH, R'=F, R"=OH; or
(c) R=OH, R'=OH, R"=F.

15. An asparagine-linked oligosaccharide derivative containing at least one fucose in N-acetylglucosamine on the nonreducing terminal side of the asparagine-linked α2,3-oligosaccharide derivative having undeca- to hepta-saccharides containing fluorine and represented by the formula (1) given below

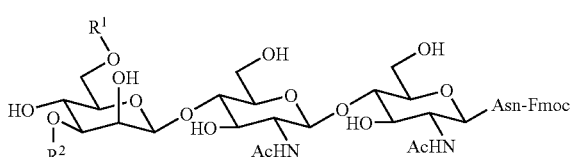

wherein $R^1$ and $R^2$ are each a hydrogen atom or one of the groups represented by the formulae (2) to (5) given below and may be the same or different, provided that one of $R^1$ and $R^2$ should always be the group of the formula (2)

(2)

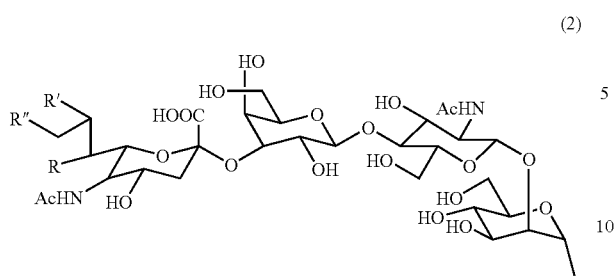

wherein R, R' and R" are in the following combinations:
(a) R=F, R'=OH, R"=OH;
(b) R=OH, R'=F, R"=OH;
(c) R=OH, R'=OH, R"=F; or
(d) R=OH, R'=OH, R"=OH;

(3)
(4)
(5)

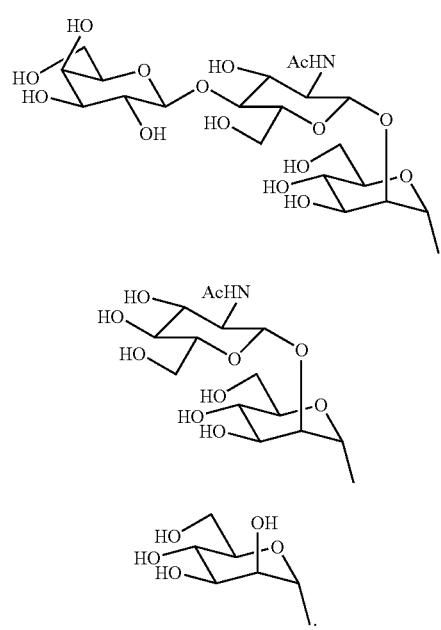

16. An asparagine-linked oligosaccharide derivative containing at least one fucose in N-acetylglucosamine on the nonreducing terminal side of the asparagine-linked α2,6-oligosaccharide derivative having undeca- to hepta-saccharides containing fluorine and represented by the formula (6) given below (6)

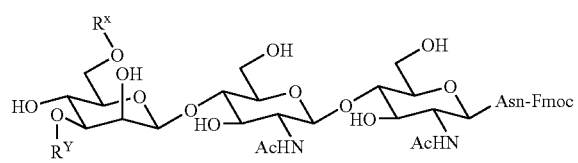

wherein $R^X$ and $R^Y$ are each a hydrogen atom, a group represented by the formula (7) given below or one of the groups represented by the formulae (3) to (5) given below, provided that one of $R^X$ and $R^Y$ should always be a group of the formula (7)

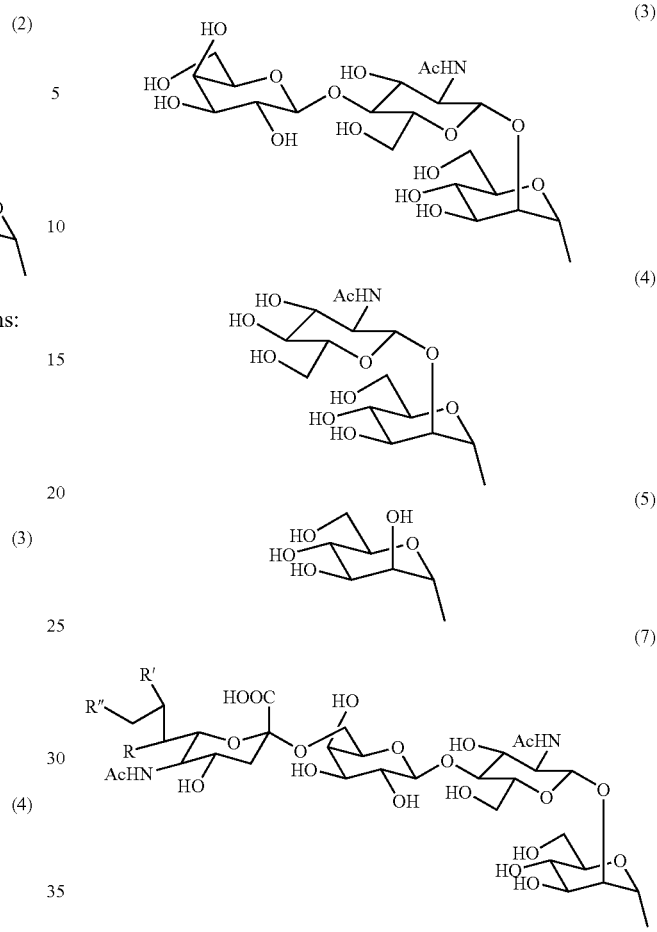

wherein R, R' and R" are in the following combinations:
(a) R=F, R'=OH, R"=OH;
(b) R=OH, R'=F, R"=OH; or
(c) R=OH, R'=OH, R"=F.

17. A process for preparing an asparagine-linked oligosaccharide derivative containing at least one fucose in N-acetylglucosamine on the nonreducing terminal side of an asparagine-linked oligosaccharide containing fluorine wherein the asparagine has amino group protected with a lipophilic protective group and represented by the formula (1) given below, the process comprising:

transferring fucose to the asparagine-linked oligosaccharide wherein the asparagine has the protected amino group with a lipophilic protective group using a fucose transferase; and subjecting the resulting asparagine-linked oligosaccharide protected with the lipophilic protective group to chromatography for separation (1)

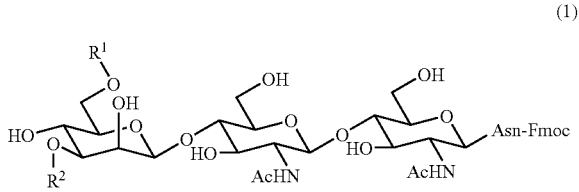

wherein $R^1$ and $R^2$ are each a hydrogen atom or one of the groups represented by the formulae (2) to (5) given below and may be the same or different, provided that one of $R^1$ and $R^2$ should always be the group of the formula (2)

(2)

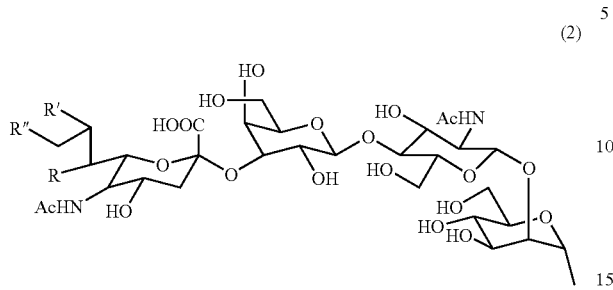

wherein R, R' and R" are in the following combinations:
(a) R=F, R'=OH, R"=OH;
(b) R=OH, R'=F, R"=OH;
(c) R=OH, R'=OH, R"=F; or
(d) R=OH, R'=OH, R"=OH;

(3)

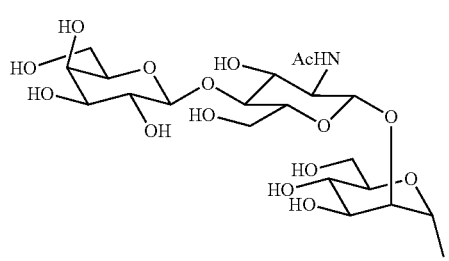

(4)

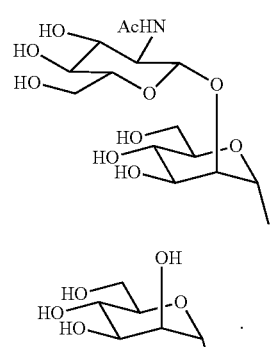

(5)

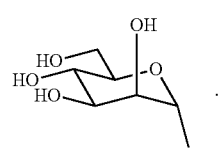

18. A process for preparing an asparagine-linked oligosaccharide derivative containing at least one fucose in N-acetylglucosamine on the nonreducing terminal side of an asparagine-linked oligosaccharide containing fluorine wherein the asparagine has amino group protected with a lipophilic protective group and represented by the formula (6) given below, the process comprising:
transferring fucose to the asparagine-linked oligosaccharide wherein the asparagine has the protected amino group with a lipophilic protective group using a fucose transferase; and
subjecting the resulting asparagine-linked oligosaccharide protected with the lipophilic protective group to chromatography for separation (6)

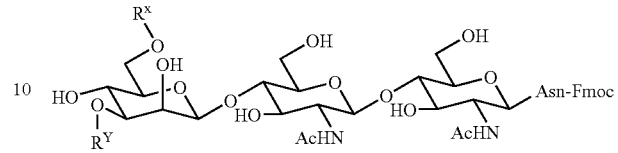

wherein $R^X$ and $R^Y$ are each a hydrogen atom, a group represented by the formula (7) or one of the groups represented by the formulae (3) to (5) given below, provided that one of $R^X$ and $R^Y$ should always be a group of the formula (7)

(3)

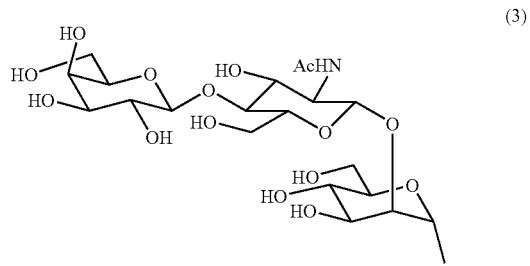

(4)

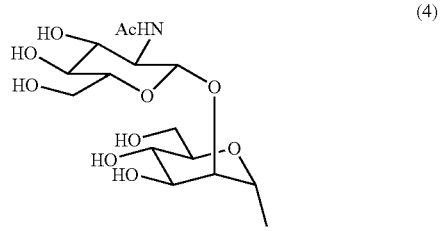

(5)

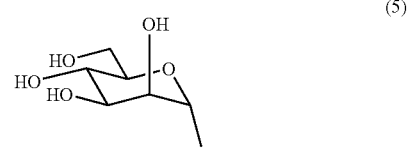

(7)

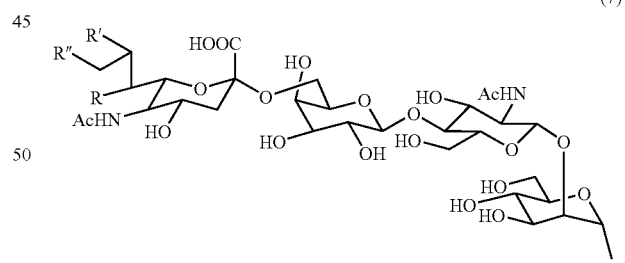

wherein R, R' and R" are in the following combinations:
(a) R=F, R'=OH, R"=OH;
(b) R=OH, R'=F, R"=OH; or
(c) R=OH, R'=OH, R"=F.

* * * * *

UNITED STATES PATENT AND TRADEMARK OFFICE
CERTIFICATE OF CORRECTION

PATENT NO. : 8,158,763 B2
APPLICATION NO. : 11/976527
DATED : April 17, 2012
INVENTOR(S) : Kajihara et al.

It is certified that error appears in the above-identified patent and that said Letters Patent is hereby corrected as shown below:

In the Patent:
Column 16, Line 7: Please correct "two kinds of a 2,6-"
  to read -- two kinds of α 2,6- --
Line 15: Please correct "(D₂O, 30%)" to read -- (D₂O, 30°C) --

Column 31, Line 7: Please correct "120.18 Hz," to read -- 12.18 Hz --

Column 32, Reference Example 15, Lines 1-10: Please correct structure

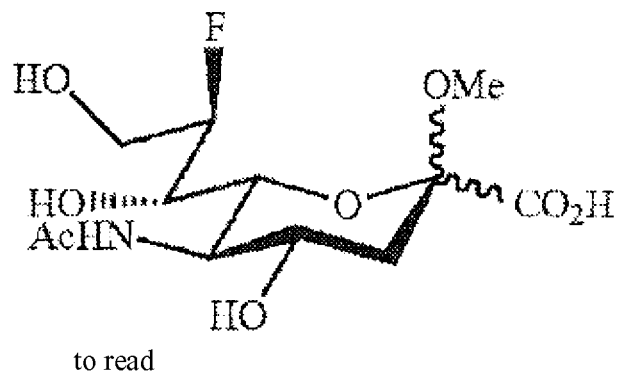

to read

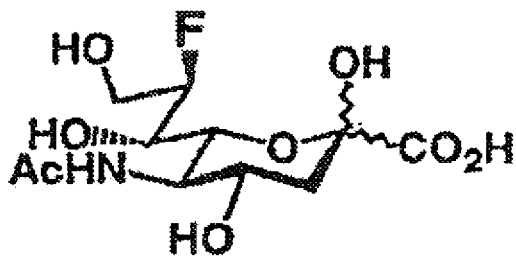

Signed and Sealed this
Eighteenth Day of September, 2012

David J. Kappos
Director of the United States Patent and Trademark Office

Column 32, Reference Example 16, Lines 49-54: Please correct structure
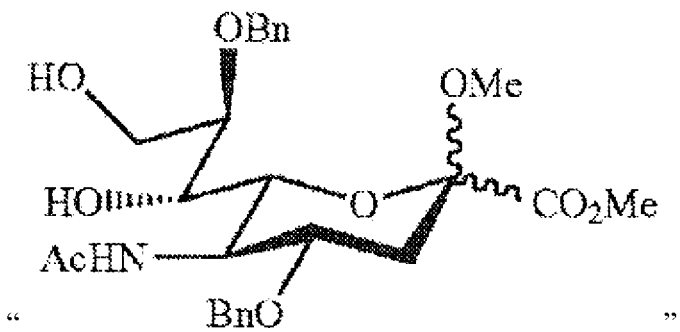
to read
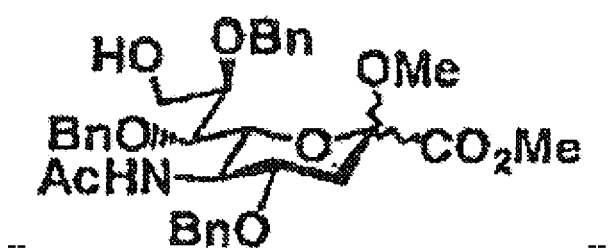
Columns 67 and 68: Please replace the portion of Table 1 that appears in Columns 67 and 68 as follows:
Table 1
Example 52.
Starting material:
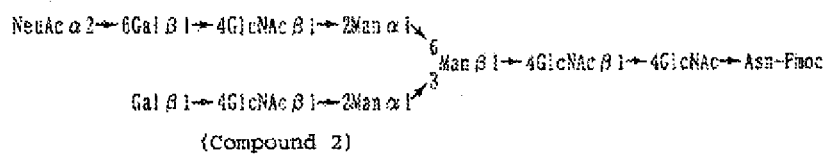
(Compound 2)
Product:
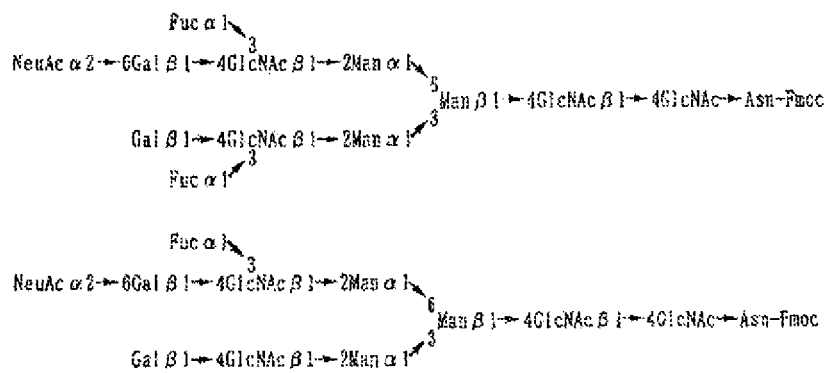
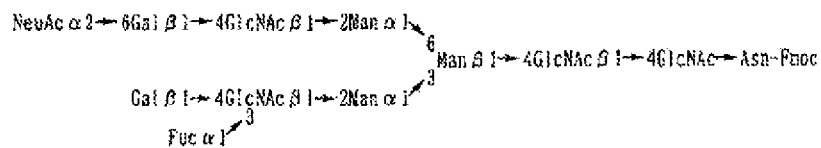
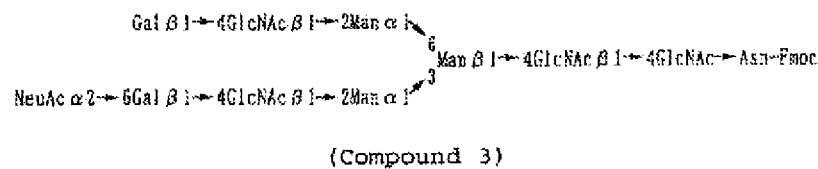
Example 53
Starting material:
NeuAc α2→6Gal β1→4GlcNAc β1→2Man α1
Gal β1→4GlcNAc β1→2Man α1
(shown as compound structure)
(Compound 3)